(12) United States Patent
Goldenberg et al.

(10) Patent No.: US 7,560,110 B2
(45) Date of Patent: *Jul. 14, 2009

(54) PRODUCTION AND USE OF NOVEL PEPTIDE-BASED AGENTS WITH BISPECIFIC ANTIBODIES

(75) Inventors: David M. Goldenberg, Mendham, NJ (US); Hans J. Hansen, Picayune, MS (US); William J. McBride, Boonton, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 263 days.

This patent is subject to a terminal disclaimer.

(21) Appl. No.: 11/198,846

(22) Filed: Aug. 8, 2005

(65) Prior Publication Data
US 2006/0034759 A1  Feb. 16, 2006

Related U.S. Application Data

(60) Division of application No. 10/150,654, filed on May 17, 2002, now Pat. No. 7,138,103, which is a continuation-in-part of application No. 09/823,746, filed on Apr. 3, 2001, now Pat. No. 6,962,702, and a continuation-in-part of application No. 09/382,186, filed on Aug. 23, 1999, now Pat. No. 7,052,872, each which is a continuation-in-part of application No. 09/337,756, filed on Jun. 22, 1999, now Pat. No. 7,074,405.

(60) Provisional application No. 60/104,156, filed on Oct. 14, 1998, provisional application No. 60/090,142, filed on Jun. 22, 1998.

(51) Int. Cl.
*A61K 39/395* (2006.01)

(52) U.S. Cl. ............... 424/133.1; 424/1.69; 424/9.3; 424/9.4; 424/9.41; 424/9.5; 424/9.51; 424/9.52; 424/9.6; 424/9.61; 424/136.1

(58) Field of Classification Search ........ None
See application file for complete search history.

(56) References Cited

U.S. PATENT DOCUMENTS

| | | | |
|---|---|---|---|
| 4,468,457 A | 8/1984 | Goldenberg et al. |
| 4,735,210 A | 4/1988 | Goldenberg |
| 4,737,453 A | 4/1988 | Primus |
| 4,792,521 A | 12/1988 | Shochat |
| 4,818,709 A | 4/1989 | Primus |
| 4,863,713 A | 9/1989 | Goodwin et al. |
| 4,971,792 A | 11/1990 | Steplewski et al. |
| 5,078,998 A | 1/1992 | Bevan et al. |
| 5,101,827 A | 4/1992 | Goldenberg |
| 5,128,119 A | 7/1992 | Griffiths |
| 5,183,756 A | 2/1993 | Schlom |
| 5,225,541 A | 7/1993 | Hackett et al. |
| 5,274,076 A | 12/1993 | Barbet et al. |
| 5,328,679 A | 7/1994 | Hansen et al. |
| 5,469,854 A | 11/1995 | Unger et al. |
| 5,502,037 A | 3/1996 | Kondratyer |
| 5,503,987 A | 4/1996 | Wagner |
| 5,534,254 A | 7/1996 | Huston |
| 5,591,828 A | 1/1997 | Bosslet et al. |
| 5,683,694 A | 11/1997 | Bagshawe et al. |
| 5,693,762 A | 12/1997 | Queen et al. |
| 5,697,902 A | 12/1997 | Goldenberg |
| 5,716,595 A | 2/1998 | Goldenberg |
| 5,746,996 A | 5/1998 | Govindan et al. |
| 5,753,206 A | 5/1998 | McBride et al. |
| 5,772,981 A | 6/1998 | Govindan et al. |
| 5,776,093 A | 7/1998 | Goldenberg |
| 5,776,094 A | 7/1998 | Goldenberg |
| 5,776,095 A | 7/1998 | Goldenberg |
| 5,837,242 A | 11/1998 | Holliger et al. |
| 5,837,243 A | 11/1998 | Deo et al. |
| 5,851,527 A | 12/1998 | Hansen et al. |
| 5,959,083 A | 9/1999 | Bosslet et al. |
| 6,010,680 A | 1/2000 | Govindan et al. |
| 6,077,499 A | 6/2000 | Griffiths |
| 6,096,289 A | 8/2000 | Goldenberg |

(Continued)

FOREIGN PATENT DOCUMENTS

EP  0263046  4/1988

(Continued)

OTHER PUBLICATIONS

Cruse et al, Illustrated Dictionary of Immunology, CRC Press, 1995, p. 117.*

(Continued)

*Primary Examiner*—David A Saunders
(74) *Attorney, Agent, or Firm*—Richard A. Nakashima

(57) ABSTRACT

The present invention relates to a bi-specific antibody or antibody fragment having at least one arm that specifically binds a targeted tissue and at least one other arm that specifically binds a targetable construct. The targetable construct comprises a carrier portion which comprises or bears at least one epitope recognizable by at least one arm of said bi-specific antibody or antibody fragment. The targetable construct further comprises one or more therapeutic or diagnostic agents or enzymes. The invention provides constructs and methods for producing the bi-specific antibodies or antibody fragments, as well as methods for using them.

78 Claims, 7 Drawing Sheets

U.S. PATENT DOCUMENTS

| | | | |
|---|---|---|---|
| 6,121,424 A | 9/2000 | Whitlow et al. | |
| 6,126,916 A | 10/2000 | McBride | |
| 6,187,284 B1 | 2/2001 | Griffiths | |
| 6,540,980 B1 * | 4/2003 | Blumenthal et al. | 424/9.34 |
| 6,962,702 B2 | 11/2005 | Hansen | |
| 7,074,405 B1 | 7/2006 | Hansen | |
| 7,138,103 B2 * | 11/2006 | Goldenberg et al. | 424/1.69 |
| 2002/0006379 A1 | 1/2002 | Hansen et al. | |

FOREIGN PATENT DOCUMENTS

| | | |
|---|---|---|
| EP | 0511011 A | 10/1992 |
| EP | 0517024 A2 | 12/1992 |
| EP | 0623675 | 11/1994 |
| IE | 921782 | 12/1992 |
| JP | 03173900 A | 7/1991 |
| WO | WO 9604313 | 2/1996 |
| WO | WO 97/41898 | 11/1997 |
| WO | WO 9808875 | 3/1998 |
| WO | WO 99/66951 A2 | 12/1999 |
| WO | WO 00/34317 | 6/2000 |

OTHER PUBLICATIONS

Paganelli et al, Nuclear Medicine Communications, 12, 211-234, 1991.*

Paul, Fundamental Immunology, Third Edition, Raven Press, 1993, pp. 292-295.*

Arano, Yasushi, et al., "Reassessment of Diethylenetriaminepentaacetic Acid (DTPA) as a Chelating Agent for Indium-111 Labeling of Polypeptides Using a Newly Synthesized Monoreactive DTPA Derivative," J. Med. Chem. vol. 39, pp. 3451-3460, 1996.

Barmas, A., et al., "Two-Step Strategies for the Diagnosis and Treatment of Cancer with Bioconjugates" Antibody, Immunoconjugates, Radiopharm., vol. 5, No. 4, pp. 385-395, 1992.

Bos, Ebo S., et al., "in Vitro Evaluation of DNA-DNA Hybridization as a Two-Step Approach in Radioimmunotherapy of Cancer," Cancer Research, vol. 54, pp. 3479-3486, 1994.

Gautherot, et al.; "Radioimmunotherapy of LS174T Colon carcinoma in Nude Mice Using an Iodine-131-Labeled Bivalent Hapten Combined with an Anti-CEA X Anti-lindium-DTPA Bispecific Antibody," J. Nucl. Med., vol. 38, pp. 7, 1997.

Greenwood, F. C., et al., "The Preparation of 131I-Labelled Human Growth Hormone of High Specific Radioactivity," The Biochemical Journal, vol. 89, pp. 114-123; 1963.

Kaneko, T., "New Hydrazone Derivative of Adriamycin and Their Immunoconjugates—a Correlation between Acid Stability and Cytotoxicity," J. Bioconjugate Chem., vol. 2, No. 3., pp. 133-141, 1991.

Losman, M. J., et al., "Generation and Monitoring of Cell Lines Producing Humanized Antibodies," Clin. Cancer Research, vol. 5, (10 Suppl.) pp. 3101s-3105s, 1999.

Penefsky, Harvey S., "A Centrifuged-Column Procedure for the Measurement of Ligand Binding by Beef Heart F," Methods in Enzymology, Part G, vol. 56, pp. 527-530, 1979.

Wang, Shing-Ming, et al., "Specific Activiation of Glucuronide Prodrugs by Antibody-targeted Enzyme Conjugates for Cancer Therapy," Cancer Res., vol. 52, pp. 4484-4491, 1992.

De Jonge, Jan, et al., "Production and Characterization of Bispecific Single-Chain Antibody Fragments," Molecular Immunology, vol. 32, No. 17/18, pp. 1405-1412, 1995.

Boden, V., et al., "Preliiminary Study of the Metal Binding Site of an Anti-DTPA-lindium Antibody by Equilibrium Binding Immunoassays and Immobilized Metal Ion Affiinity Chromatogrphy," Bioconjugate Chem., vol. 6, pp. 373-379, 1995.

Gold et al., Cancer Research, 50 6405-6409, 1990.

Van Spriel, et al., "Immunotherapeutic Perspective for Bispecific antibodies" Immunology Today. 21, 391-396, 2000.

Kontermann, Roland E., "Intracellular and Cell Surface Displayed single-chain Diabodies" Journal of Immunological Methods 226 (1999) 179-188.

Dubel, S., "Reconstitution of human pancreatic RNase from two separate fragments fused to different single chain antibody fragments: on the way to binary immunotoxins" Tumor Targeting (1999) 4, 37-46 XP009010728.

Hayden, M., "Single-chain mono- and bispecific antibody derivatives with novel biological properties and antitumour activity from a COS cell transient expression system" Therapeutic Immunology, 1994, 1, 3-15.

Yang "A Genetically Engineered Single-Chain FV/TNF Molecule Possesses the Anti-Tumor Immunoreactivity of FV as well as the Cytotoxic Activity of Tumor Necrosis Factor" Molecular Immunology vol. 32, No. 12, pp. 873-881, 1995 XP 000653177.

Karacay, et al., "Experimental Pretargeting Studies of Cancer with a Humanized anti-CEA x Murine anti-{In-DTPA] Bispecific Antibody Construct and a 99mTc-/188Re-Labeled Peptide" Bioconjugate Chem. 2000, 11, 842-854 pp. 842-854 XP-02230983.

Karacay, H., et al. "Pretargeting Studies with a Murine Anti-Colon-Specific Antigen-P (CSAp) X Chimeric Anti-[Indium-DTPA] Bispecific Antibody and Technetium-99m-Labeled Peptide" Cancer Biotherapy and Radiopharmaceuticals, vol. 15, No. 4, 2000, p. 412, XP008065412.

Communication from the European Patent Office, Jul. 10, 2006, supplementary partial European search report for EP 02725464 (6 pages).

McGuinness at al. Phage diabody repertoires for selection of large numbers of bispecific antibody fragments, Nature Biotechnology. 14:1149-1154 (1996).

Alt et al. "Novel tetravalent and bispecific lgG-like antibody molecules combining single chain diabodies with the immunoglobulin gamma-1 or CH3 region," FEBBS LETT 454: 90-94 (1999).

Olafsen et al., "1gM secretory tailpiece drives multimerisation of bivalent scFv fragments in eukaryotic Cells," Immunotechnology, 4(2):141-153 (1998).

Kipriyanov et al. "Bispecific tandem diabody for tumor therapy with improved antigen binding and pharmacokinetics," J. Mol. Biol., 293(1):41-56 (1999).

Karacay et al. "Studies on a humanized anti-CEA x murine anti-(In-DTPA) bispecific antibody construct for radioimmunotherapy of CEA-positive tumors," Proceedings of the American Association for Cancer Research Annual Meeting, vol. 40, p. 644, (Mar. 1999).

Karacay et al., "Pretargeting studies with a humanized anti-CEAX murine anti-(In- DTPA) bispecific antibody construct and Tc-99m/ Re-188 labeled peptide," Journal of Nuclear Medicine, vol. 40, No. 5 Suppl., p. 225 (May 1999).

Gautherot et al "Delivery of therapeutic doses of radiojodine using bispecific antibody—targeted bivalent haptens," Journal of Nuclear Medicine, vol. 39 (11), pp. 1937-1943 (Nov. 1998).

Bodere et al. "Phase I/II total of two-step radioimmunotherapy in medullary thyroid cancer (MTC) using bispecific anti-CEA/anti-DTPA—in antibody and iodine-131-labeled bivalent hapten," Journal of Nuclear Medicine, vol. 39, No. 5 Suppl, p. 246 (May 1998).

Bardies et al Bispecific antibody and iodine-131-labeled bivalent hapten dosimetry in patients with medullary thyroid or small-cell lung cancer,~ Journal of Nuclear Medicine, vol. 37, pp. 1853-1859 (Nov. 1996).

Kraeber-Booere et al. Bispecific antibody and bivalent hapten radloimmunotherapy in CEA producing medullary thyroid cancer xenograft, Journal of Nuclear Medicine, vol. 40 (1), pp. 198-204 (Jan. 1999).

Hosono et al. "Biodistribution and dosimetric study in medullary thyroid cancer xenograft using bispecific antibody and iodine-125-labeled bivalent hapten." Journal of Nuclear Medicine, vol. 39 (9), pp. 1608-1613 (Sep. 1998).

Kranenborg et al. Two-step radio-immunotargeting of renal-cell carcinoma xenografts in nude mice with anti-renal-cell-carcinoma X anti-DTPA bispecific monoclonal antibodies, International Journal of Cancer, vol. 75.(1), pp. 74-80 (Jan. 5, 1998).

Gautherot Therapy for colon carcinoma xenografts with bispecific antibody—targeted, iodine-131-labeled bivalent hapten, Cancer, vol. 80, No. Suppl. 12, pp. 2618-2623 (Dec. 15, 1997).

Bosslet et al., "Generation of bispecific monoclonal antibodies for two phase radioimmunotherapy," British Journal of Cancer, vol. 63/5, pp. 681-686 (1991).

Manetti et al., "Intracellular uptake and catabolism of anti-igM antibodies and bi-specific antibody-targeted hapten by B-lymphoma cells," Int. J. Cancer, vol. 63(2), pp. 250-256 (1995).

Barbet et al. Radioimmunotherapy of LS174T colon carcinoma in nude mice using an iodine-131-labeled bivalent hapten combined with an anti-CEAX anti-indium- DTPA bispecific antibody, Tumor Biology, vol. 18, No. Suppl. 2, p. 31 (Sep. 1997).

Hawkins et al. "Delivery of Radionuclides to Pretargeted Monoclonal, Antibodies Using Dihydrofolate Reductase and Methotrexagte in an Affinity System," Cancer Research, vol. 53, pp. 2368-2373, May 1993.

Goodwin et al. "Pre-Targeted Immunoscintigraphy of Murine Tumors with Indium-111-Labeled Bifunctional Haptens," J. Nucl., Med., vol. 29, pp. 226-234. 1998.

Stickney et al. Bifunctional Antibody: A Binary Radiopharmaceutical Delivery System for Imaging Colorectal Carcinoma, Cancer Research, vol. 51, pp. 6650-6655, Dec. 15, 1991.

Gautherot et al. "Therapy for Colon Carcinoma Xenografts with Bispecific Antobody-Targeted, Iodine-131-Labeled Bivalent Hapten." Cancer Supplement, vol. 80, pp. 2618-2623, 1997.

Barbet et al. Radioimmunodetection of Medullary Thyroid Carcinoma Using Indium-III Bivalent Hapten and Anti-CEA X Anti-DTPA-Indium, The Journal of Nuclear Medicine. vol. 39, No. 7, Jul. 1998.

Kranenborg at al. "Development and Characterization of Anti-Renal Cell Carcinoma x Antichetate Bispecific Monoclonal Antibodies for Two-Phase Targeting of Renal Cell Carcinoma," Cancer Research Supplement vol. 55, pp. 5864s-5867s, Dec. 1, 1995.

Schuhmacher et al., "Multistep Tumor Targeting in Nude ice Using Bispecific Antibodies and a Gallium Chelate Suitable for Immunoscintigrapnhy with Positron Emission Tomography," Cancer Research, vol. 55, pp. 115-123, Jan. 1, 1995.

Sharkey et al., "Development of a Streptavidin-Anti-Carcinoembryonic Antigen Antibody, Radiolabeled Biotin Pretargeting Method for Radioimmunotherapy of Colorectal Cancer Studies in a Colon Cancer Xenograft Model,", Bioconjugate Chemical, vol. 8, No. 4, 1997.

PCT, Notification of Transmittal of the International Search Report or the Declaration for PCT/GB03/02110, mailed on Sep. 11, 2003.

Hillairet de Boisferon et al., "Enhanced Targeting Specificity to Tumor Cells by Simultaneous Recognition of Two Antigents", Bioconjugate Chem. 2000, 11, 452-460.

Pluckthun et al., "New protein engineering approaches to multivalent and bispecific antibody fragments", Immunotechnology 3 (1997) 83-105.

Pack et al., "Tetravalent Miniantibodies with High Avidity Assembling in *Escherichia coli*", J. Mol. Biol. (1995) 246, 28-34.

Sharkey et al., "A Universal Pretargeting System for Cancer Detection and Therapy Usnig Bispecific Antibody", Cancer Research 63, 354-363 (Jan. 15, 2003).

* cited by examiner

Figure 1. Schematic illustration of various Abs and bsAbs.
HMN14　　　734scFV　　　hMN14Fab-　　　hMN14-
　　　　　　　　　　　　　734scFv　　　　734scFv

Figure 2. SDS-PAGE analysis of purified hMN-14Fab-734scFv.
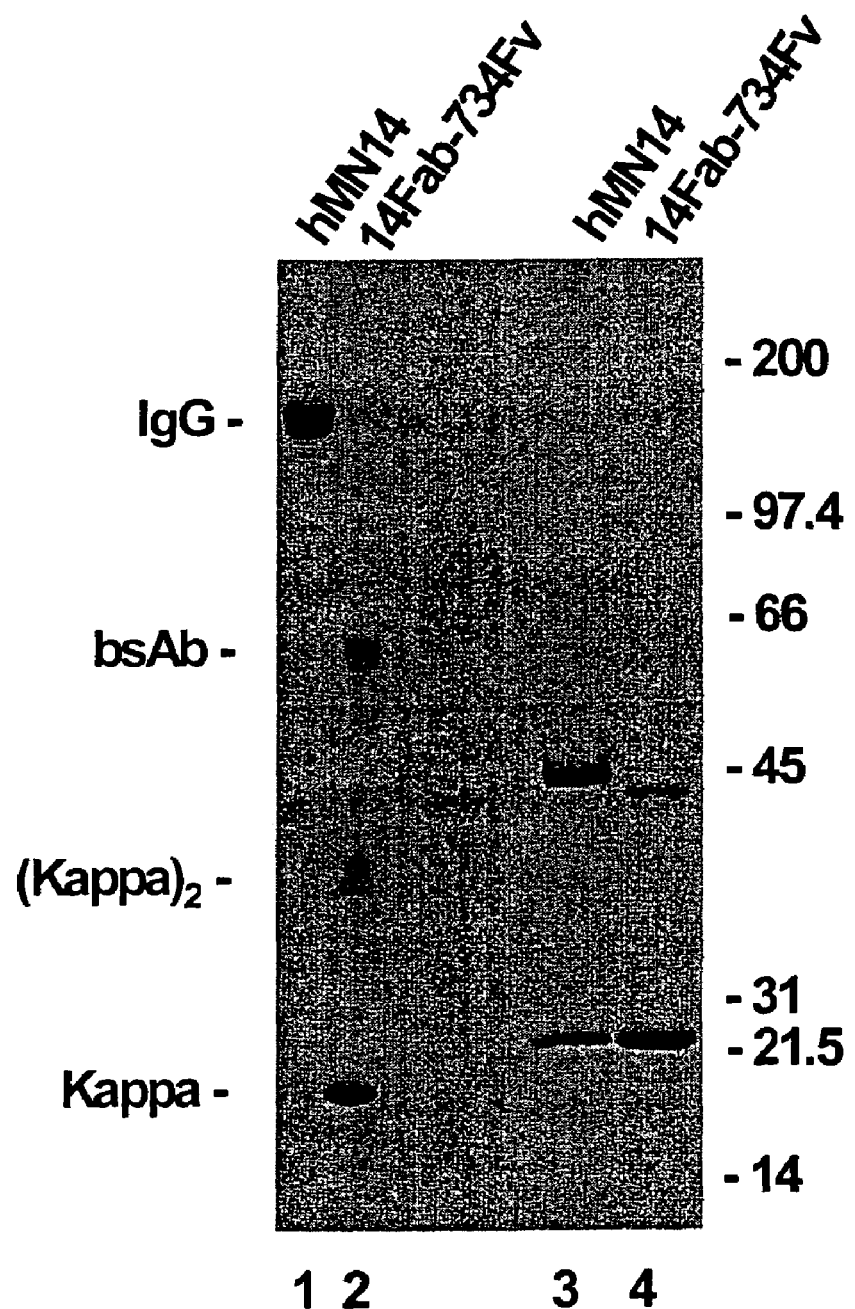

Figure 3. Schematic illustration of two bi-specific fusion proteins.
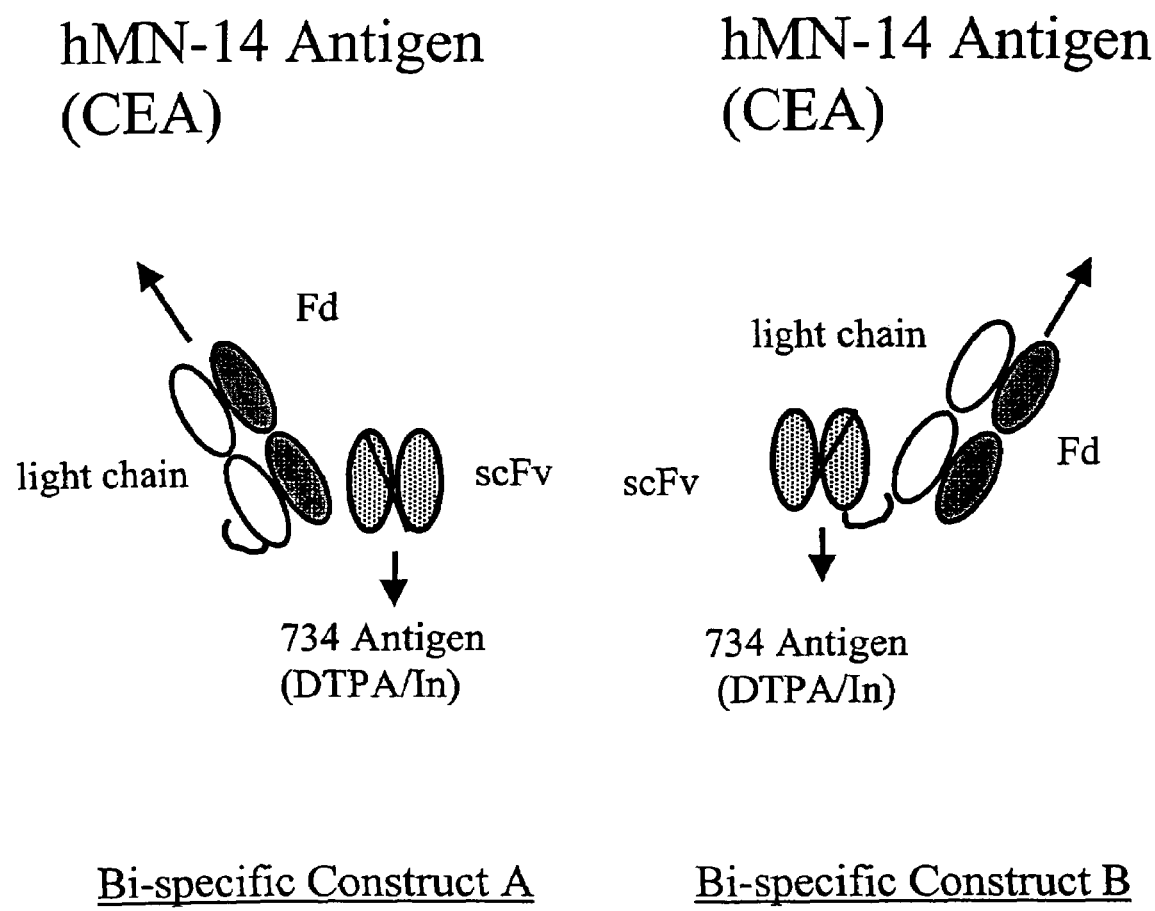

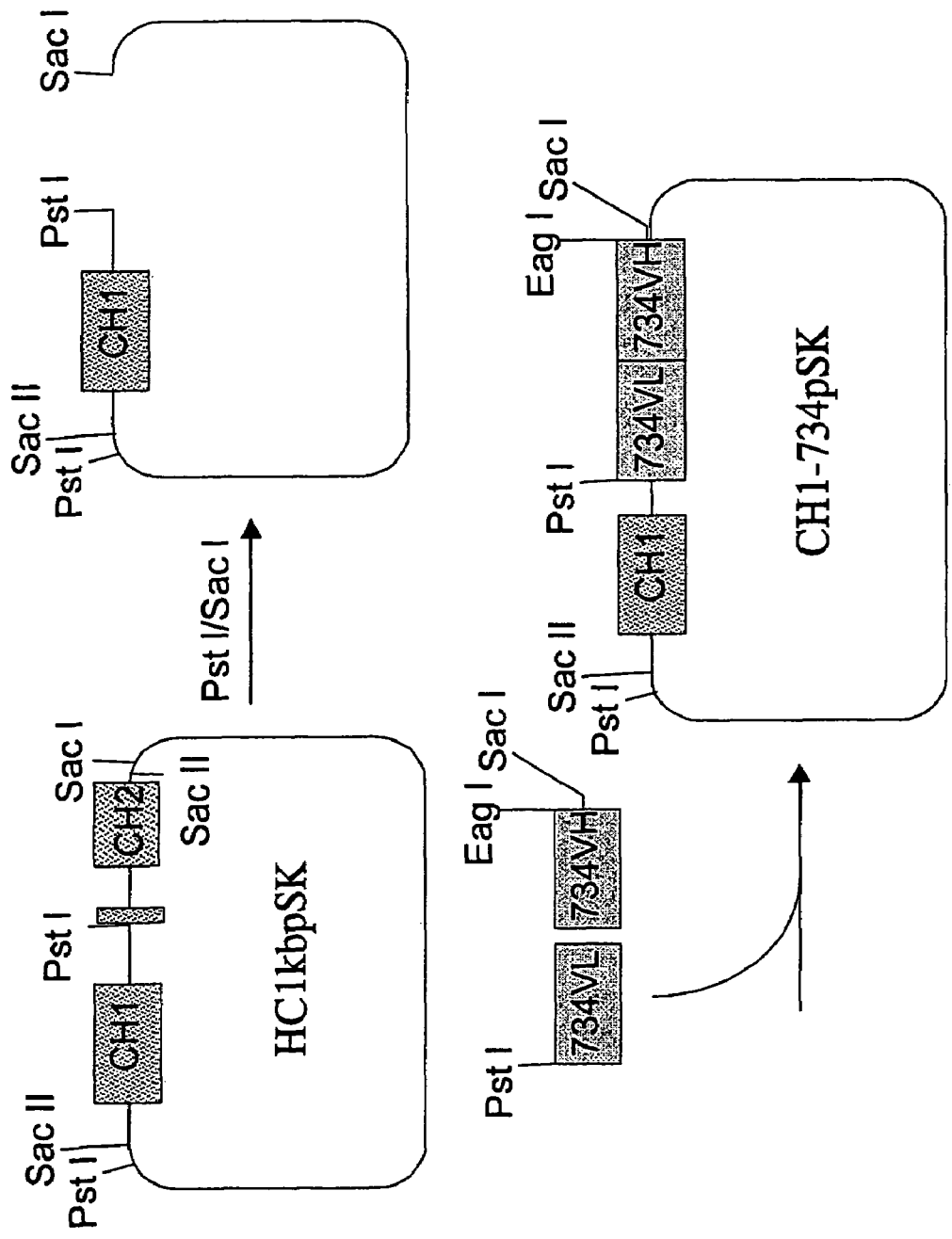
Figure 4. Schematic diagram illustrating production of a 14Fab-734scFv DNA construct.

Figure 5. Schematic diagram illustrating production of a hMN-14Fab-734scFv DNA construct.
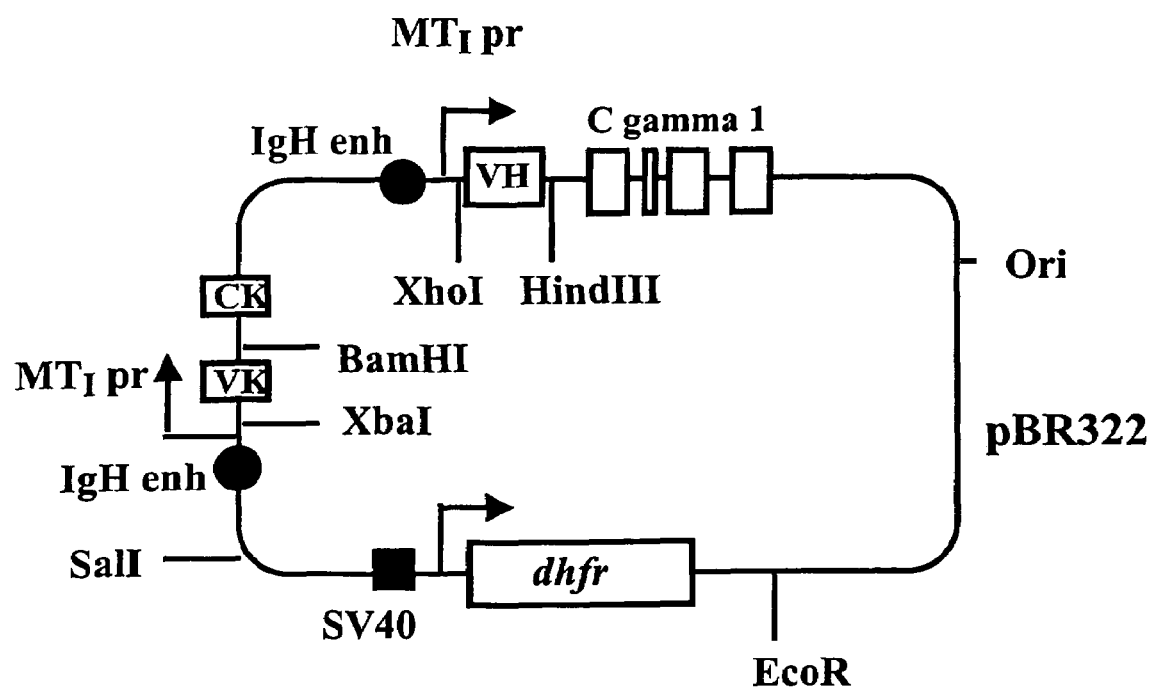
Plasmid Map of MN-14pdHL2

Figure 6: Binding properties of hMN-14 x m679 bsMAb with $^{111}$In-labeled IMP-241 divalent HSG-DOTA peptide.
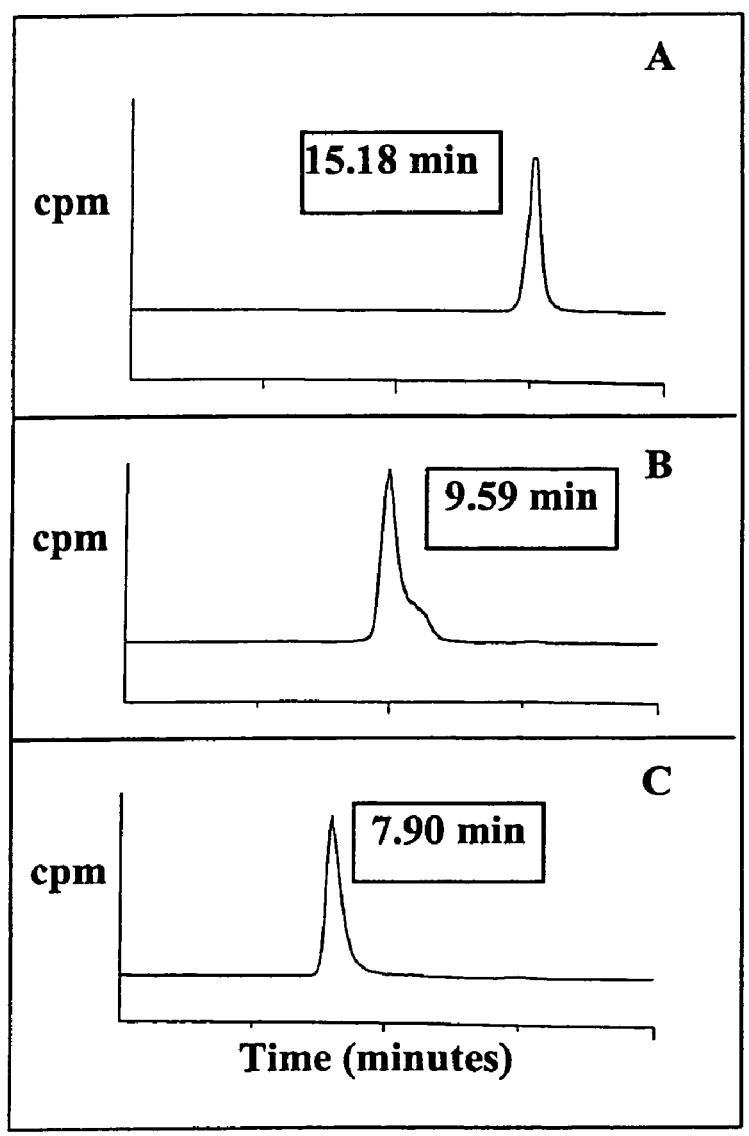

Figure 7: Clearance of $^{125}$I-mMu-9 x m679 F(ab')$_2$ bsMAb and $^{111}$In-IMP-241 in GW-39 tumor-bearing nude mice.
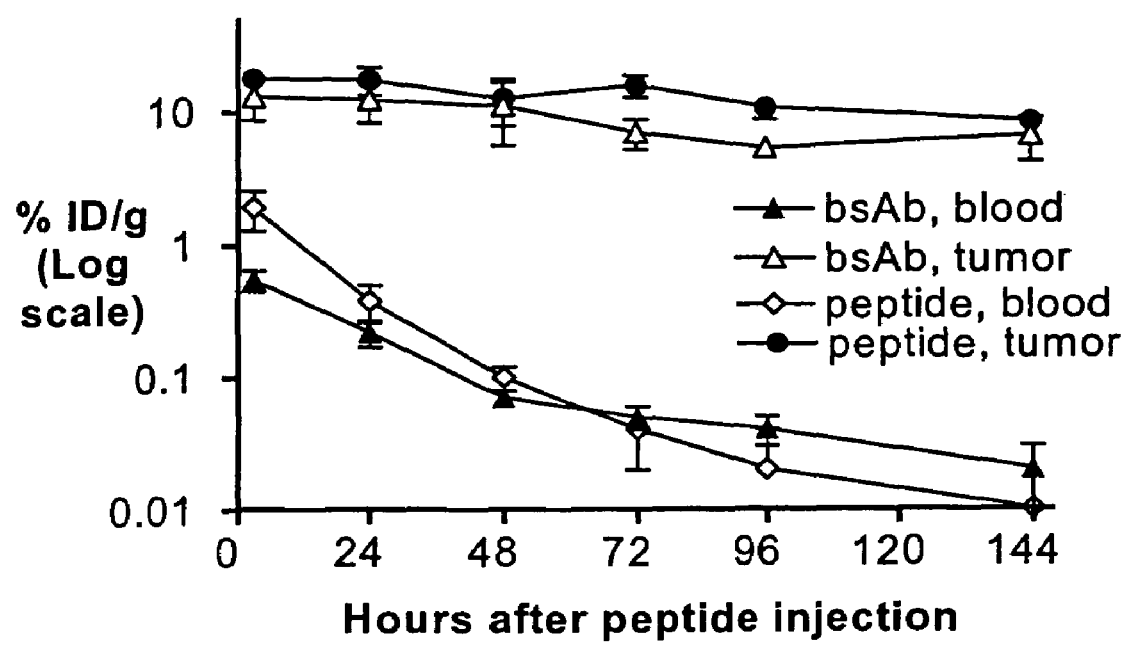

PRODUCTION AND USE OF NOVEL PEPTIDE-BASED AGENTS WITH BISPECIFIC ANTIBODIES

This application is a divisional of U.S. patent application Ser. No. 10/150,654, filed May 17, 2002 (now issued U.S. Pat. No. 7,138,103); which was a continuation-in-part of U.S. patent application Ser. No. 09/823,746, filed Apr. 3, 2001 (now issued U.S. Pat. No. 6,962,702); and a continuation-in-part of U.S. patent application Ser. No. 09/382,186, filed Aug. 23, 1999 (now issued U.S. Pat. No. 7,052,872); both Ser. Nos. 09/823,746 and 09/382,186 applications were continuations-in-part of U.S. patent application Ser. No. 09/337,756, filed Jun. 22, 1999 (now issued U.S. Pat. No. 7,074,405); which claimed priority to U.S. Provisional Application No. 60/104,156, filed Oct. 14, 1998 (now expired) and U.S. Provisional Application No. 60/090,142, filed Jun. 22, 1998 (now expired), the contents of each of which are incorporated herein by reference in their entirety.

BACKGROUND OF THE INVENTION

1. Field of the Invention.

The invention relates to immunological reagents for therapeutic use, for example, in radioimmunotherapy (RAIT), and diagnostic use, for example, in radioimmunodetection (RAID) and magnetic resonance imaging (MRI). In particular, the invention relates to bi-specific antibodies. (bsAb) and bi-specific antibody fragments (bsFab) which have at least one arm that specifically binds a targeted tissue and at least one other arm that specifically binds a targetable construct. Further, the invention relates to monoclonal antibodies that have been raised against specific immunogens, humanized and chimeric monoclonal bi-specific antibodies and antibody fragments having at least one arm that specifically binds a targeted tissue and at least one other arm that specifically binds a targetable construct, DNAs that encode such antibodies and antibody fragments, and vectors for expressing the DNAs. Earlier provisional patent applications, U.S. Ser. No. 60/090,142 and U.S. Ser. No. 60/104,156 disclose a part of what is now included in this invention and are incorporated herein by reference in their entireties.

2. Related Art

An approach to cancer therapy and diagnosis involves directing antibodies or antibody fragments to disease tissues, wherein the antibody or antibody fragment can target a diagnostic agent or therapeutic agent to the disease site. One approach to this methodology which has been under investigation, involves the use of bsAbs having at least one arm that specifically binds a targeted diseased tissue and at least one other arm that specifically binds a low molecular weight hapten. In this methodology, a bsAb is administered and allowed to localize to target, and to clear normal tissue. Some time later, a radiolabeled low molecular weight hapten is given, which being recognized by the second specificity of the bsAb, also localizes to the original target.

Although low MW haptens used in combination with bsAbs possess a large number of specific imaging and therapy uses, it is impractical to prepare individual bsAbs for each possible application. Further, the application of a bsAb/low MW hapten system has to contend with several other issues. First, the arm of the bsAb that binds to the low MW hapten must bind with high affinity, since a low MW hapten is designed to clear the living system rapidly, when not bound by bsAb. Second, the non-bsAb-bound low MW hapten actually needs to clear the living system rapidly to avoid non-target tissue uptake and retention. Third, the detection and/or therapy agent must remain associated with the low MW hapten throughout its application within the bsAb protocol employed.

Of interest with this approach are bsAbs that direct chelators and metal chelate complexes to cancers using Abs of appropriate dual specificity. The chelators and metal chelate complexes used are often radioactive, using radionuclides such as cobalt-57 (Goodwin et al., U.S. Pat. No. 4,863,713), indium-111 (Barbet et al., U.S. Pat. No. 5,256,395 and U.S. Pat. No. 5,274,076, Goodwin et al., *J. Nucl. Med.*, 33:1366-1372 (1992), and Kranenborg et al., *Cancer Res* (suppl.), 55:5864s-5867s (1995) and *Cancer* (suppl.) 80:2390-2397 (1997)) and gallium-68 (Boden et al., *Bioconjugate Chem.*, 6:373-379, (1995) and Schuhmacher et al., *Cancer Res.*, 55:115-123 (1995)) for radioimmuno-imaging. Because the Abs were raised against the chelators and metal chelate complexes, they have remarkable specificity for the complex against which they were originally raised. Indeed, the bsAbs of Boden et al. have specificity for single enantiomers of enantiomeric mixtures of chelators and metal-chelate complexes. This great specificity has proven to be a disadvantage in one respect, in that other nuclides such as yttrium-90 and bismuth-213 useful for radioimmunotherapy (RAIT), and gadolinium useful for MRI, cannot be readily substituted into available reagents for alternative uses. As a result iodine-131, a non-metal, has been adopted for RAIT purposes by using an I-131-labeled indium-metal-chelate complex in the second targeting step. A second disadvantage to this methodology requires that antibodies be raised against every agent desired for diagnostic or therapeutic use.

Pretargeting methodologies have received considerable attention for cancer imaging and therapy. Unlike direct targeting systems where an effector molecule (e.g., a radionuclide or a drug linked to a small carrier) is directly linked to the targeting agent, in pretargeting systems, the effector molecule is given some time after the targeting agent. This allows time for the targeting agent to localize in tumor lesions and, more importantly, clear from the body. Since most targeting agents have been antibody proteins, they tend to clear much more slowly from the body (usually days) than the smaller effector molecules (usually in minutes). In direct targeting systems involving therapeutic radionuclides, the body, and in particular the highly vulnerable red marrow, is exposed to the radiation all the while the targeting agent is slowly reaching its peak levels in the tumor and clearing from the body. In a pretargeting system, the radionuclide is usually bound to a small "effector" molecule, such as a chelate or peptide, which clears very quickly from the body, and thus exposure of normal tissues is minimized. Maximum tumor uptake of the radionuclide is also very rapid because the small molecule efficiently transverses the tumor vasculature and binds to the primary targeting agent. Its small size may also encourage a more uniform distribution in the tumor.

Pretargeting methods have used a number of different strategies, but most often involve an avidin/streptavidin-biotin recognition system or bi-specific antibodies that co-recognize a tumor antigen and the effector molecule. The avidin/streptavidin system is highly versatile and has been used in several configurations. Antibodies can be coupled with streptavidin or biotin, which is used as the primary targeting agent. This is followed sometime later by the effector molecule, which conjugated with biotin or with avidin/streptavidin, respectively. Another configuration relies on a 3-step approach first targeting a biotin-conjugated antibody, followed by a bridging with streptavidin/avidin, and then the biotin-conjugated effector is given. These systems can be easily converted for use with a variety of effector substances so long as the effector and the targeting agent can be coupled with biotin or streptavidin/avidin depending on the configuration used. With its versatility for use in many targeting situations and high binding affinity between avidin/streptavidin and biotin, this type of pretargeting has considerable advantages over other proposed systems. However, avidin and streptavidin are foreign proteins and therefore would be immunogenic, which would limit the number of times they could be given in a clinical application. In this respect, bsAbs have the advantage of being able to be engineered as a relatively non-immunogenic humanized protein. Although the binding affinity of a bsAb (typically $10^{-9}$ to $10^{-10}$ M) cannot compete with the extremely high affinity of the streptavidin/avidin-biotin affinity (~$10^{-15}$ M), both pretargeting systems are dependent on the binding affinity of the primary targeting agent, and therefore the higher affinity of the streptavidin/avidin-biotin systems may not offer a substantial advantage over a bsAb pretargeting system. However, most bsAbs have only one arm available for binding the primary target, whereas the streptavidin/avidin-biotin pretargeting systems have typically used a whole IgG with two arms for binding the target, which strengthens target binding. By using a divalent peptide, an affinity enhancement is achieved, which greatly improves the binding of the peptide to the target site compared to a monovalent peptide. Thus, both systems are likely to provide excellent targeting ratios with reasonable retention.

Pretargeting with a bsAb also requires one arm of the antibody to recognize an effector molecule. Most radionuclide targeting systems reported to date have relied on an antibody to a chelate-metal complex, such as antibodies directed indium-loaded DTPA or antibodies to other chelates. Since the antibody is generally highly selective for this particular chelate-metal complex, new bsAbs would need to be constructed with the particular effector antibody. This could be avoided if the antibody was not specific to the effector, but instead reacted with another substance. In this way, a variety of effectors could be made so long as they also contained the antibody recognition substance. We have continued to develop the pretargeting system originally described by Janevik-Ivanovska et al. that used an antibody directed against a histamine derivative, histamine-succinyl-glycl (HSG) as the recognition system on which a variety of effector substances could be prepared. Excellent pretargeting results have been reported using a radioiodinated and a rhenium-labeled divalent HSG-containing peptide. In this work, we have expanded this system to include peptides suitable for radiolabeling $^{90}$Y, $^{111}$In, and $^{177}$Lu, as well as an alternative $^{99m}$Tc-binding peptide.

Thus, there is a continuing need for immunological agents which can be directed to diseased tissue and can specifically bind to a subsequently administered targetable diagnostic or therapeutic conjugate, and a flexible system that accommodates different diagnostic and therapeutic agents without alteration to the bi-specific or multi-specific antibodies.

OBJECTS OF THE INVENTION

It is one object of the present invention to provide a multi-specific antibody or antibody fragment having at least one arm that specifically binds a targeted tissue and at least one other arm that specifically binds a targetable construct that can be modified for use in a wide variety of diagnostic and therapeutic applications.

Other objects of the invention are to provide pre-targeting methods of diagnosis and therapy using the combination of multi-specific antibody and targetable construct, methods of making the multi-specifics, and kits for use in such methods.

In accomplishing the foregoing object, the present inventors have discovered that it is advantageous to raise multi-specific Abs against a targetable construct that is capable of carrying one or more diagnostic or therapeutic agents. By utilizing this technique, the characteristics of the chelator, metal chelate complex, therapeutic agent or diagnostic agent can be varied to accommodate differing applications, without raising new multi-specific Abs for each new application. Further, by using this approach, two or more distinct chelators, metal chelate complexes, diagnostic agents or therapeutic agents can be used with the inventive multi-specific Ab.

SUMMARY OF THE INVENTION

The present invention relates to a multi-specific or bi-specific antibody or antibody fragment having at least one arm that specifically binds a targeted tissue and at least one other arm that specifically binds a targetable construct.

Provided is a compound of the formula X-Phe-Lys(HSG)-D-Tyr-Lys(HSG)-Lys(Y)-NH$_2$ (SEQ ID NO: 1), where the compound includes a hard acid cation chelator positioned at X or Y and a soft acid cation chelator positioned at remaining X or Y. The hard acid cation chelator may include a carboxylate or amine group, and may include such chelators as NOTA, DOTA, DTPA, and TETA. The soft acid cation chelator may include a thiol group, and may also include such chelators as Tscg-Cys and Tsca-Cys. A preferred embodiment of this compound is DOTA-Phe-Lys(HSG)-D-Tyr-Lys(HSG)-Lys(Tscg-Cys)-NH$_2$ (SEQ ID NO: 1) also known as IMP 245. Other embodiments may have a hard acid cation chelator and a soft acid cation chelator in switched positions as provided in (Tscg-Cys)-Phe-Lys(HSG)-D-Tyr-Lys(HSG)-Lys(DOTA)-NH$_2$ (SEQ ID NO: 1).

The compound may also include cations bound to the different chelating moeities. For example, hard acid cations may include Group IIa and Group IIIa metal cations, which commonly bind to hard acid chelators. Soft acid cations that may bind to the soft acid chelators can include the transition metals, lanthanides, actinides and/or Bi. Non exhaustive examples of such soft acid cations include Tc, Re, and Bi.

Also provided is a targetable construct including X-Phe-Lys(HSG)-D-Tyr-Lys(HSG)-Lys(Y)—NH—R (SEQ ID NO: 1). Again, a hard acid cation chelator is positioned at either X or Y, and a soft acid cation chelator is positioned at remaining X or Y. The targetable construct also includes a linker to conjugate the compound to a therapeutic or diagnostic agent or enzyme "R". The linker may have at least one amino acid for conjugating the R group to the compound. Examples of therapeutic agents include a drug, prodrug (e.g, epirubicin glucuronide, CPT-11, etoposide glucuronide, daunomicin glucuronide and doxorubicin glucuronide) or toxin (e.g., ricin, abrin, ribonuclease, DNase I, Staphylococcal enterotoxin-A, pokeweed antiviral protein, gelonin, diphtherin toxin, Pseudomonas exotoxin, and Pseudomonas endotoxin).

Other examples of therapeutic agents include doxorubicin, SN-38, etoposide, methotrexate, 6-mercaptopurine and/or etoposide phosphate. Diagnostic agents may include nuclides, one or more agents for photodynamic therapy (e.g, a photosensitizer such as benzoporphyrin monoacid ring A (BPD-MA), tin etiopurpurin (SnET2), sulfonated aluminum phthalocyanine (AlSPc) and lutetium texaphyrin (Lutex)), contrast agents and image enhancing agents for use in magnetic resonance imaging (MRI) and computed tomography (CT). Enzymes may also serve as the R group which may be capable of converting a prodrug to a drug at the target site; or capable of reconverting a detoxified drug intermediate to a toxic form to increase toxicity of said drug at a target site.

In one embodiment, the invention provides a method of treating, diagnosing and/or identifying diseased tissues in a patient, comprising:

(A) administering to the patient a bi-specific antibody or antibody fragment having at least one arm that specifically binds a targeted tissue and at least one other arm that specifically binds a targetable construct;

(B) optionally, administering to the patient a clearing composition, and allowing the composition to clear non-localized antibodies or antibody fragments from circulation;

(C) administering to the patient a first targetable construct which comprises a carrier portion which comprises or bears at least one epitope recognizable by the at least one other arm of the bi-specific antibody or antibody fragment, and one or more conjugated therapeutic or diagnostic agents, or enzymes; and (D) when the targetable construct comprises an enzyme, further administering to the patient
1) a prodrug, when the enzyme is capable of converting the prodrug to a drug at the target site; or
2) a drug which is capable of being detoxified in the patient to form an intermediate of lower toxicity, when the enzyme is capable of reconverting the detoxified intermediate to a toxic form, and, therefore, of increasing the toxicity of the drug at the target site, or
3) a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or
4) a second targetable construct which comprises a carrier portion which comprises or bears at least one epitope recognizable by the at least one other arm of the bi-specific antibody or antibody fragment, and a prodrug, when the enzyme is capable of converting the prodrug to a drug at the target site.

In another embodiment, the invention provides a kit useful for treating or identifying diseased tissues in a patient comprising:

(A) a bi-specific antibody or antibody fragment having at least one arm that specifically binds a targeted tissue and at least one other arm that specifically binds a targetable construct;

(B) a first targetable construct which comprises a carrier portion which comprises or bears at least one epitope recognizable by the at least one other arm of the bi-specific antibody or antibody fragment, and one or more conjugated therapeutic or diagnostic agents, or enzymes; and (C) optionally, a clearing composition useful for clearing non-localized antibodies and antibody fragments; and (D) optionally, when the first targetable construct comprises an enzyme,
1) a prodrug, when the enzyme is capable of converting the prodrug to a drug at the target site; or
2) a drug which is capable of being detoxified in the patient to form an intermediate of lower toxicity, when the enzyme is capable of reconverting the detoxified intermediate to a toxic form, and, therefore, of increasing the toxicity of the drug at the target site, or
3) a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or
4) a second targetable construct which comprises a carrier portion which comprises or bears at least one epitope recognizable by the at least one other arm of the bi-specific antibody or antibody fragment, and a prodrug, when the enzyme is capable of converting the prodrug to a drug at the target site.

Another embodiment of the invention is to provide DNA constructs which encode such antibodies or antibody fragments. Specifically, DNA constructs which produce the variable regions which provide the advantageous properties of reactivity to a targetable construct and reactivity to a disease tissue. In accordance with this aspect of the present invention, there is provided a recombinant DNA construct comprising an expression cassette capable of producing in a host cell a bi-specific antibody or antibody fragment having at least one arm that specifically binds a targeted tissue and at least one other arm that specifically binds a targetable construct, wherein the construct comprises, in the 5' to 3' direction of transcription, a transcriptional initiation regulatory region functional in the host cell, a translational initiation regulatory region functional in the host cell, a DNA sequence encoding the bi-specific antibody or antibody fragment, and a transcriptional and translational termination regulatory region functional in the host cell, wherein the bi-specific antibody or antibody fragment is under the control of the regulatory regions.

Another embodiment of the invention provides a method of preparing the antibodies or antibody fragments by recombinant technology. In accordance with this aspect of the present invention, there is provided a method of preparing a bi-specific antibody or antibody fragment having at least one arm that specifically binds a targeted tissue and at least one other arm that specifically binds a targetable construct, comprising:

(A) introducing the recombinant DNA construct described above into a host cell;

(B) growing the cell and isolating the antibody or antibody fragment.

In another embodiment of the present invention there is provided a method of preparing a bi-specific fusion protein having at least one arm that specifically binds to a targeted tissue and at least one other arm that is specifically binds to a targetable construct, comprising:

(1) (A) introducing into a host cell a recombinant DNA construct comprising an expression cassette capable of producing in the host cell a fragment of the bi-specific fusion protein, wherein the construct comprises, in the 5' to 3' direction of transcription, a transcriptional initiation regulatory region functional in the host cell, a translational initiation regulatory region functional in the host cell, a DNA sequence encoding a scFv linked to a light-chain antibody fragment, and a transcriptional and translational termination regulatory region functional in the host cell, wherein the fragment of the bi-specific fusion protein is under the control of the regulatory regions;

(B) co-introducing into the host cell a recombinant DNA construct comprising an expression cassette capable of producing in the host cell a Fd fragment which is complementary to the light-chain antibody fragment in (A) and which when associated with the light-chain antibody fragment forms a Fab fragment whose binding site is specific for the targeted tissue, wherein the construct comprises, in the 5' to 3' direction of transcription, a transcriptional initiation regulatory region functional in the host cell, a translational initiation regulatory region functional in the host cell, a DNA sequence encoding a Fd fragment, and a transcriptional and translational termination regulatory region functional in the host cell, wherein the Fd fragment is under the control of the regulatory regions;

(C) growing the cell and isolating the bi-specific fusion protein, or (2) (A) introducing into a first host cell a recombinant DNA construct comprising an expression cassette capable of producing in the first host cell a fragment of the bi-specific fusion protein, wherein the construct comprises, in the 5' to 3' direction of transcription, a transcriptional initiation regulatory region functional in the first host cell, a translational initiation regulatory region functional in the first host cell, a DNA sequence encoding a scFv linked to a light-chain antibody fragment, and a transcriptional and translational termination regulatory region functional in the first host cell, wherein the fragment of the bi-specific fusion protein is under the control of the regulatory regions;

(B) introducing into a second host cell a recombinant DNA construct comprising an expression cassette capable of producing in the second host cell a Fd fragment which is complementary to the light-chain antibody fragment in (2)(A) and which when associated with the light-chain antibody fragment forms a Fab fragment whose binding site is specific for the targeted tissue, wherein the construct comprises, in the 5' to 3' direction of transcription, a transcriptional initiation regulatory region functional in the second host cell, a translational initiation regulatory region functional in the second host cell, a DNA sequence encoding a Fd fragment, and a transcriptional and translational termination regulatory region functional in the second host cell, wherein the Fd fragment is under the control of the regulatory regions;

(C) growing the first and second host cells;

(D) optionally isolating the bi-specific fusion protein fragment and the Fd fragment; and (E) combining the fragments to produce a bi-specific fusion protein and isolating the bi-specific fusion protein.

A variety of host cells can be used to prepare bi-specific antibodies or antibody fragments, including, but not limited to, mammalian cells, insect cells, plant cells and bacterial cells. In one embodiment, the method utilizes a mammalian zygote, and the introduction of the recombinant DNA construct produces a transgenic animal capable of producing a bi-specific antibody or antibody fragment.

The present invention seeks to provide inter alia a bi-specific antibody or antibody fragment having at least one arm that specifically binds a targeted tissue and at least one other arm that specifically binds a targetable construct that can be modified for use in a wide variety of diagnostic and therapeutic applications.

A further embodiment of the invention involves using the inventive antibody or antibody fragment in photodynamic therapy.

A further embodiment of-the invention involves using the inventive antibody or antibody fragment in radioimmunoimaging for positron-emission tomography (PET).

A further embodiment of the invention involves using the inventive antibody or antibody fragment in radioimmunoimaging for single-photon emission.

A further embodiment of the invention involves using the inventive antibody or antibody fragment in magnetic resonance imaging (MRI).

A further embodiment of the invention involves using the inventive antibody or antibody fragment in X-ray, computed tomography (CT) or ultrasound imaging.

A further embodiment of the invention involves using the inventive antibody or antibody fragment for intraoperative, endoscopic, or intravascular detection and/or therapy.

A further embodiment of the invention involves using the inventive antibody or antibody fragment in boron neutron capture therapy (BNCT).

A further embodiment of the invention involves using the inventive antibody or antibody fragment for diagnosing or treating diseased tissues (e.g., cancers, infections, inflammations, clots, atherosclerois, infarcts), normal tissues (e.g., spleen, parathyroid, thymus, bone marrow), ectopic tissues (e.g., endometriosis), and pathogens.

Further, the invention provides pre-targeting methods of diagnosis and therapy using the combination of bi-specific antibody and the following targetable constructs:

(a) DOTA-Phe-Lys(HSG)-D-Tyr-Lys(HSG)-$NH_2$ (SEQ ID NO: 3);

(b) DOTA-Phe-Lys(HSG)-Tyr-Lys(HSG)-$NH_2$ (SEQ ID NO: 2);

(c) Ac-Lys(HSG)-D-Tyr-Lys(HSG)-Lys(Tscg-Cys)-$NH_2$ (SEQ ID NO: 4);

(d) DOTA-Phe-Lys(HSG)-D-Tyr-Lys(HSG)-Lys(Tscg-Cys)-$NH_2$ (SEQ ID NO: 1);

(e) (Tscg-Cys)-Phe-Lys(HSG)-D-Tyr-Lys(HSG)-Lys(DOTA)-$NH_2$ (SEQ ID NO: 1);

(f)

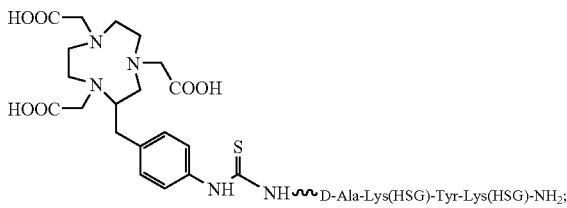

and (SEQ ID NO: 5)

(g)

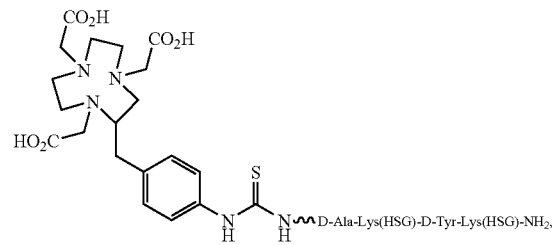

(SEQ ID NO: 6)

as well as methods of making the bi-specifics, and kits for use in such methods.

The present inventors have discovered that it is advantageous to raise bsAbs against a targetable construct that is capable of carrying one or more diagnostic or therapeutic agents. By utilizing this technique, the characteristics of the chelator, metal chelate complex, therapeutic agent or diagnostic agent can be varied to accommodate differing applications, without raising new bsAbs for each new application.

Further, by using this approach, two or more distinct chelators, metal chelate complexes or therapeutic agents can be used with the inventive bsAb.

The invention relates to a method of treating or identifying diseased tissues in a subject, comprising:

(A) administering to said subject a bi-specific antibody or antibody fragment having at least one arm that specifically binds a targeted tissue and at least one other arm that specifically binds a targetable construct comprising at least two HSG haptens;

(B) optionally, administering to said subject a clearing composition, and allowing said composition to clear non-localized antibodies or antibody fragments from circulation;

(C) administering to said subject a targetable construct which comprises a carrier portion which comprises or bears at least two HSG haptens and at least one chelator, and may comprise at least one diagnostic and/or therapeutic cation, and/or one or more chelated or chemically bound therapeutic or diagnostic agents, or enzymes; and (D) when said targetable construct comprises an enzyme, further administering to said subject 1) a prodrug, when said enzyme is capable of converting said prodrug to a drug at the target site; or
2) a drug which is capable of being detoxified in said subject to form an intermediate of lower toxicity, when said enzyme is capable of reconverting said detoxified intermediate to a toxic form, and, therefore, of increasing the toxicity of said drug at the target site, or
3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site.

The invention further relates to a method for detecting or treating target cells, tissues or pathogens in a mammal, comprising:

administering an effective amount of a bi-specific antibody or antibody fragment comprising at least one arm that specifically binds a targeted tissue and at least one other arm that specifically binds a targetable construct;

wherein said at least one arm is capable of binding to a complementary binding moiety on the target cells, tissues or pathogen or on a molecule produced by or associated therewith; and administering a targetable construct selected from the group consisting of (a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

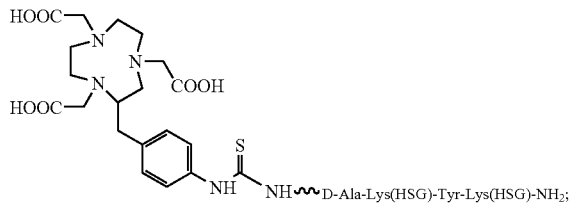

and
(SEQ ID NO: 5)
(g)

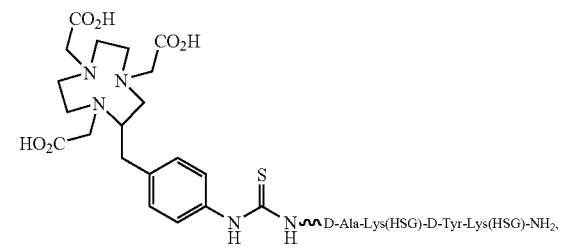

(SEQ ID NO: 6)

The invention further relates to a method of treating or identifying diseased tissues in a subject, comprising:

administering to said subject a bi-specific antibody or antibody fragment having at least one arm that specifically binds a targeted tissue and at least one other arm that specifically binds a targetable construct;

optionally, administering to said subject a clearing composition, and allowing said composition to clear non-localized antibodies or antibody fragments from circulation; and administering to said subject a targetable construct selected from the group consisting of:

(a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

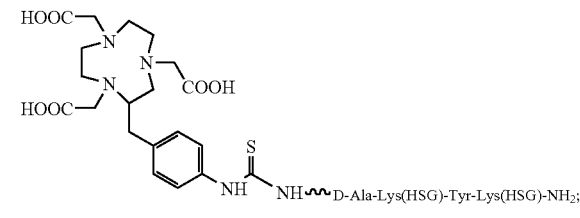

and
(SEQ ID NO: 5)
(g)

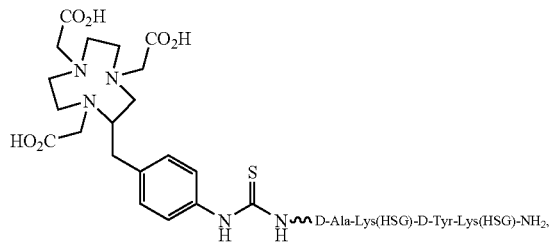

(SEQ ID NO: 6)

The invention further relates to a kit useful for treating or identifying diseased tissues in a subject comprising:

(A) a bi-specific antibody or antibody fragment having at least one arm that specifically binds a targeted tissue and at least one other arm that specifically binds a targetable construct, wherein said construct is selected from the group consisting of (a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

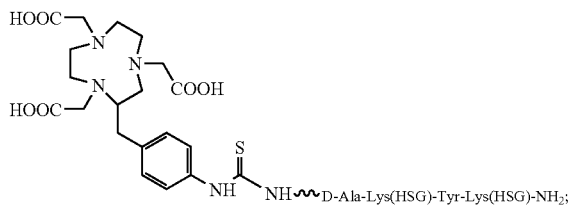

and
(SEQ ID NO: 5)
(g)

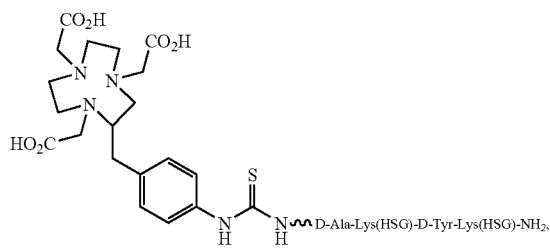

(SEQ ID NO: 6)

(B) a targetable construct which comprises a carrier portion which comprises or bears at least one epitope recognizable by said at least one other arm of said bi-specific antibody or antibody fragment, and one or more conjugated therapeutic or diagnostic agents, or enzymes; and (C) optionally, a clearing composition useful for clearing non-localized antibodies and antibody fragments; and (D) optionally, when said first targetable construct comprises an enzyme
1) a prodrug, when said enzyme is capable of converting said prodrug to a drug at the target site; or
2) a drug which is capable of being detoxified in said subject to form an intermediate of lower toxicity, when said enzyme is capable of reconverting said detoxified intermediate to a toxic form, and, therefore, of increasing the toxicity of said drug at the target site, or
3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site.

The invention further relates to a targetable construct selected from the group consisting of:

(a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

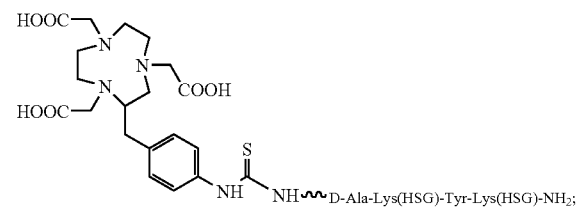

and
(SEQ ID NO: 5)
(g)

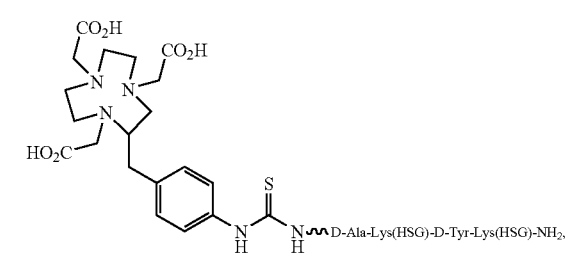

(SEQ ID NO: 6)

The invention further relates to a method of screening for a targetable construct comprising:

contacting said targetable construct with a bi-specific antibody or antibody fragment having at least one arm that specifically binds a targeted tissue and at least one other arm that specifically binds said targetable construct to give a mixture;

wherein said at least one arm is capable of binding to a complementary binding moiety on the target cells, tissues or pathogen or on a molecule produced by or associated therewith; and optionally incubating said mixture; and analyzing said mixture.

The invention further relates to a method for imaging normal tissue in a mammal, comprising:

administering an effective amount of a bi-specific antibody or antibody fragment comprising at least one arm that specifically binds a targeted tissue and at least one other arm that specifically binds a targetable construct;

wherein said at least one arm is capable of binding to a complementary binding moiety on the target cells, tissues or on a molecule produced by or associated therewith; and administering a targetable construct selected from the group consisting of (a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

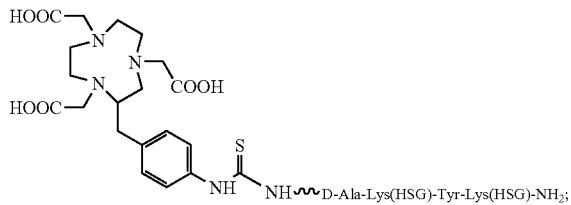

and (SEQ ID NO: 5)

(g)

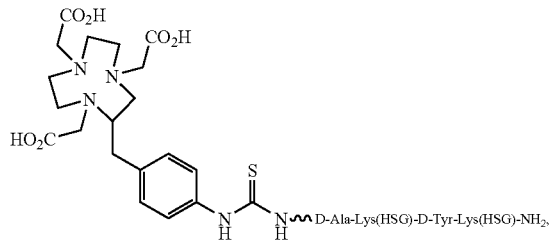

(SEQ ID NO: 6)

The invention further relates to a method of intraoperatively identifying or treating diseased tissues, in a subject, comprising:

administering an effective amount of a bi-specific antibody or antibody fragment comprising at least one arm that specifically binds a targeted tissue and at least one other arm that specifically binds a targetable construct;

wherein said at least one arm is capable of binding to a complementary binding moiety on the target cells, tissues or pathogen or on a molecule produced by or associated therewith; and administering a targetable construct selected from the group consisting of (a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

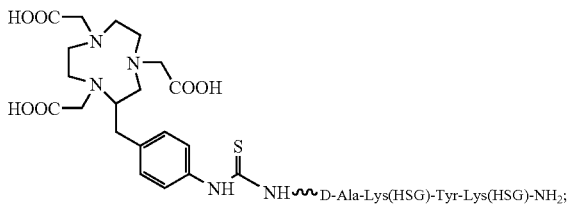

and (SEQ ID NO: 5)

(g)

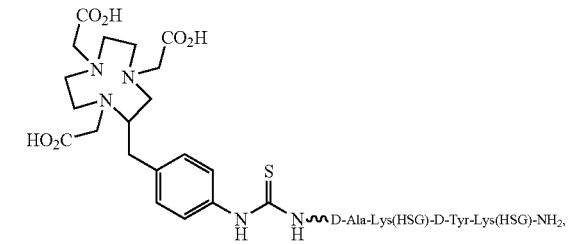

(SEQ ID NO: 6)

The invention further relates to a method for the endoscopic identification or treatment of diseased tissues, in a subject, comprising:

administering an effective amount of a bi-specific antibody or antibody fragment comprising at least one arm that specifically binds a targeted tissue and at least one other arm that specifically binds a targetable construct;

wherein said at least one arm is capable of binding to a complementary binding moiety on the target cells, tissues or pathogen or on a molecule produced by or associated therewith; and administering a targetable construct selected from the group consisting of (a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

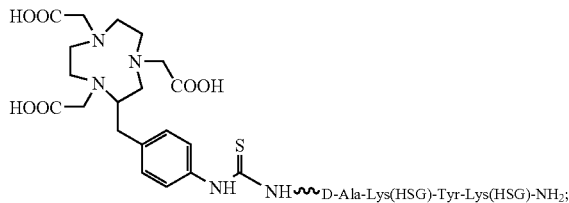

and
(SEQ ID NO: 5)
(g)

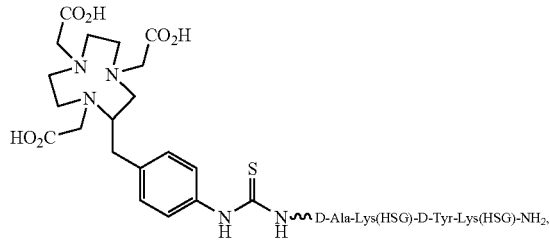

(SEQ ID NO: 6)

The invention further relates to a method for the intravascular identification or treatment of diseased tissues, in a subject, comprising:

administering an effective amount of a bi-specific antibody or antibody fragment comprising at least one arm that specifically binds a targeted tissue and at least one other arm that specifically binds a targetable construct;

wherein said at least one arm is capable of binding to a complementary binding moiety on the target cells, tissues or pathogen or on a molecule produced by or associated therewith; and administering a targetable construct selected from the group consisting of (a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID NO: 1);

(f)

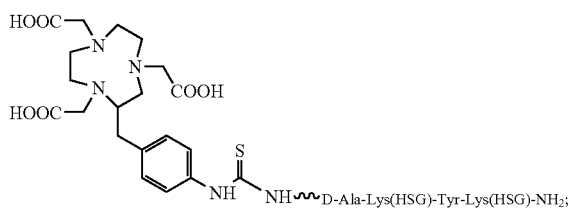

and
(SEQ ID NO: 5)
(g)

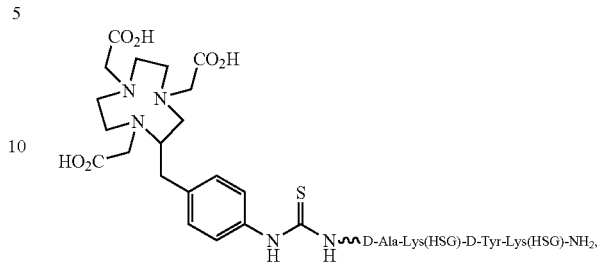

(SEQ ID NO: 6)

Additional aspects, features and advantages of the invention will be set forth in the description which follows, and in part will be obvious from the description, or may be learned by practice of the invention. The embodiments and advantages of the invention may be realized and obtained by means of the instrumentalities and combinations particularly pointed out in the appended claims.

BRIEF DESCRIPTION OF THE DRAWINGS

FIG. 1 schematically illustrates various Abs and bsAbs.

FIG. 2 provides SDS-PAGE analysis of purified hMN-14Fab-734scFv. 3 μg of hMN-14 IgG (lanes 1 and 3) or bsAb (lanes 2 and 4) was applied in each lane of a 4-20% polyacrylamide gel under non-reducing (lanes 1 and 2) and reducing (lanes 3 and 4) conditions.

FIG. 3 schematically illustrates two bi-specific fusion proteins.

FIG. 4 illustrates the production of a DNA construct useful for producing a hMN-14Fab-734scFv bi-specific fusion protein.

FIG. 5 illustrates the production of a DNA construct useful for producing a hMN-14Fab-734scFv bi-specific fusion protein.

FIG. 6 shows the binding properties of hMN-14×m679 bsMAb with $^{111}$In-labeled IMP-241 divalent HSG-DOTA peptide. Panel A: $^{111}$In-IMP-241 alone on SE-HPLC; Panel B: $^{111}$In-IMP-241 mixed with hMN-14×679 bsMAb; Panel C: $^{111}$In-IMP-241 added to a mixture containing hMN-14×m679 bsMAb with an excess of CEA. Chromatograms show the association of the $^{111}$In-IMP-241 with the bsMAb (B) and bsMAb/CEA complex (C).

FIG. 7 shows clearance of [125]I-mMu-9×m679 F(ab')$_2$ bsMAb and $^{111}$In-IMP-241 in GW-39 tumor-bearing nude mice. Mice were injected i.v. with the radiolabeled bsMAb and 48 h later the radiolabeled peptide was given i.v. Values represent the mean and standard deviations of the percent injected dose per gram (n=5 for each time interval).

DETAILED DESCRIPTION OF PREFERRED EMBODIMENTS

Unless otherwise specified, "a" or "an" means "one or more".

I. Overview

The present invention provides a bi-specific antibody (bsAb) or antibody fragment (bsFab) having at least one arm that is reactive against a targeted tissue and at least one other arm that is reactive against a targetable construct. Desirably, the targetable construct includes a peptide having at least 2 units of a recognizable hapten. Examples of recognizable haptens include, but are not limited to, histamine succinyl glycine (HSG) and fluorescein isothiocyanate. The targetable construct may be conjugated to a variety of agents useful for treating or identifying diseased tissue. Examples of conjugated agents include, but are not limited to, chelators, metal chelate complexes, drugs, toxins (e.g., ricin, abrin, ribonuclease (e.g., RNase), DNase I, *Staphylococcal* enterotoxin-A, pokeweed antiviral protein, gelonin, diphtherin toxin, *Pseudomonas* exotoxin, *Pseudomonas* endotoxin) and other effector molecules. Additionally, enzymes useful for activating a prodrug or increasing the target-specific toxicity of a drug can be conjugated to the targetable construct. Thus, the use of bsAb which are reactive to a targetable construct allows a variety of therapeutic and diagnostic applications to be performed without raising new bsAb for each application.

Bi-specific antibody (bsAb) pretargeting represents a potentially non-immunogenic, highly selective alternative for diagnostic and therapeutic applications. The bsAb pretargeting system described herein represents an additional significant advantage over other pretargeting systems in that it potentially can be developed for use with a variety of different imaging or therapeutic agents. The flexibility of this system is based on use of an antibody directed against histamine-succinyl-glycl (HSG) and the development of peptides containing the HSG residue. HSG-containing peptides were synthesized with either DOTA for the chelation of $^{111}$In, $^{90}$Y, or $^{177}$Lu or a technetium/rhenium chelate. For pretargeting, these peptides were used in combination with bi-specific antibodies using the anti-HSG Fab' chemically stabilized with the Fab' of either an anti-carcinoembryonic antigen (CEA) or an anti-colon-specific antigen-p (CSAp) antibody to provide tumor targeting capability for tumors expressing these antigens. However, other antigen targets may include diverse tumor-associated antigens known in the art, such as against CD19, CD20, CD21, CD22, CD23, CD30, CD74, CD 80, HLA-DR, Ia, MUC 1, MUC 2, MUC 3, MUC 4, EGFR, HER 2/neu, PAM-4, BrE3, TAG-72 (B72.3, CC49), EGP-1 (e.g., RS7), EGP-2 (e.g., 17-1A and other Ep-CAM targets), Le(y) (e.g., B3), A3, KS-1, S100, IL-2, T101, necrosis antigens, folate receptors, angiogenesis markers (e.g., VEGF), tenascin, PSMA, PSA, tumor-associated cytokines, MAGE and/or fragments thereof. Tissue-specific antibodies (e.g., against bone marrow cells, such as CD34, CD74, etc., parathyroglobulin antibodies, etc.) as well as antibodies against non-malignant diseased tissues, such as fibrin of clots, macrophage antigens of atherosclerotic plaques (e.g., CD74 antibodies), and also specific pathogen antibodies (e.g., against bacteria, viruses, and parasites) are well known in the art.

The peptides can be radiolabeled to a high specific activity in a facile manner that avoids the need for purification. In vivo studies in tumor bearing nude mice showed the radiolabeled peptides cleared rapidly from the body with minimal retention in tumor or normal tissues. When administered 1 to 2 days after a pretargeting dose of the bsAbs, tumor uptake of the radiolabeled peptides increased from 28 to 175-fold with tumor/nontumor ratios exceeded 2:1 to 8:1 within just 3 hour of the peptide injection, which represented a marked improvement over that seen with a $^{99m}$Tc-anti-CEA Fab' at this same time. The anti-CSAp×anti-HSG F(ab')$_2$ bsAb had the highest and longest retention in the tumor, and when used in combination with the $^{111}$In-labeled peptide, radiation dose estimates for therapeutic radionuclides, such as $^{90}$Y and $^{177}$Lu, suggested that as much 12,000 cGy could be delivered to tumors with the kidneys receiving 1500 cGy, but all other tissues receiving 500 cGy. Thus, this pretargeting system is highly flexible, being capable of using a wide array of compounds of diagnostic imaging and therapeutic interest, and by achieving excellent tumor uptake and targeting ratios, is highly promising for use in these applications.

Additionally, encompassed is a method for detecting and/or treating target cells, tissues or pathogens in a mammal, comprising administering an effective amount of a bi-specific antibody or antibody fragment comprising at least one arm that specifically binds a targeted tissue and at least one other arm that specifically binds a targetable construct. As used herein, the term "pathogen" includes, but is not limited to fungi (e.g., Microsporum, Trichophyton, Epidermophyton, *Sporothrix schenckii, Cryptococcus neoformans, Coccidioides immitis, Histoplasma Capsulatum, Blastomyces dermatitidis, Candida albicans*), viruses (e.g., human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus), parasites, bacteria (e.g., *Anthrax bacillus, Streptococcus agalactiae, Legionella pneumophilia, Streptococcus pyogenes, Escherichia coli, Neisseria gonorrhoeae, Neisseria meningitidis, Pneumococcus, Hemophilis influenzae* B, *Treponema pallidum*, Lyme disease spirochetes, *Pseudomonas aeruginosa, Mycobacterium leprae, Brucella abortus, Mycobacterium tuberculosis* and *Tetanus toxin*), mycoplasma (e.g., *Mycoplasma arthritidis, M. hyorhinis, M. orale, M. arginini, Acholeplasma laidlawii, M. salivarum*, and *M. pneumoniae*) and protozoans (e.g., *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides corti*). See U.S. Pat. No. 5,332,567.

Also provided herein are antibodies and antibody fragments. The antibody fragments are antigen binding portions of an antibody, such as F(ab')$_2$, F(ab)$_2$, Fab', Fab, and the like. The antibody fragments bind to the same antigen that is recognized by the intact antibody. For example, an anti-CD22 monoclonal antibody fragment binds to an epitope of CD22.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the "hypervariable region." Three of these so-called "hypervariable" regions or "complementarity-determining regions" (CDR) are found in each variable region of the light or heavy chain. Each CDR is flanked by relatively conserved framework regions (FR). The FR are thought to maintain the structural integrity of the variable region. The CDRs of a light chain and the CDRs of a corresponding heavy chain form the antigen-binding site. The "hypervariability" of the CDRs accounts for the diversity of specificity of antibodies.

As used herein, the term "subject" refers to any animal (i.e., vertebrates and invertebrates) including, but not limited to humans and other primates, rodents (e.g., mice, rats, and guinea pigs), lagamorphs (e.g., rabbits), bovines (e.g, cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

II. Constructs Targetable to Antibodies

The targetable construct can be of diverse structure, but is selected not only to diminish the elicitation of immune responses, but also for rapid in vivo clearance when used within the bsAb targeting method. Hydrophobic agents are best at eliciting strong immune responses, whereas hydrophilic agents are preferred for rapid in vivo clearance, thus, a balance between hydrophobic and hydrophilic needs to be established. This is accomplished, in part, by relying on the use of hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may be used.

The targetable construct may include a peptide backbone having as few as two amino-acid residues, with preferably two to ten amino acid residues, and may be coupled to other moieties such as chelating agents. The targetable construct should be a low molecular weight construct, preferably having a molecular weight of less than 50,000 daltons, and advantageously less than about 20,000 daltons, 10,000 daltons or 5,000 daltons, including any metal ions that may be bound to the chelating agents. For instance, the known peptide DTPA-Tyr-Lys(DTPA)-OH (wherein DTPA is diethylenetriaminepentaacetic acid) has been used to generate antibodies against the indium-DTPA portion of the molecule. However, by use of the non-indium-containing molecule, and appropriate screening steps, new Abs against the tyrosyl-lysine dipeptide can be made. More usually, the antigenic peptide of the targetable construct will have four or more residues, such as the peptide DOTA-Phe-Lys(HSG)-Tyr-Lys(HSG)-$NH_2$ (SEQ ID NO: 2), wherein DOTA is 1,4,7,10-tetraazacyclododecanetetraacetic acid and HSG is the histamine succinyl glycyl group of the formula:

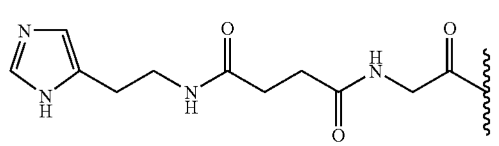

The non-metal-containing peptide may be used as an immunogen, with resultant Abs screened for reactivity against the Phe-Lys-Tyr-Lys (SEQ ID NO: 2) backbone.

The haptens of the targetable construct also provide an immunogenic recognition moiety, for example, a chemical hapten. Using a chemical hapten, preferably the HSG hapten, high specificity of the construct for the antibody is exhibited. This occurs because antibodies raised to the HSG hapten are known and can be easily incorporated into the appropriate bsAb. Thus, binding of the haptens to the peptide backbone would result in a targetable construct that is specific for the bsAb or bsFab.

The invention also contemplates the incorporation of unnatural amino acids, e.g., D-amino acids, into the peptide backbone structure to ensure that, when used with the final bsAb/construct system, the arm of the bsAb which recognizes the targetable construct is completely specific. The invention further contemplates other backbone structures such as those constructed from non-natural amino acids and peptoids.

The peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts *Protective Groups in Organic Synthesis,* 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity.

III. Chelate Moieties

The presence of hydrophilic chelate moieties on the targetable construct helps to ensure rapid in vivo clearance. In addition to hydrophilicity, chelators are chosen for their metal-binding properties, and may be changed at will since, at least for those targetable constructs whose bsAb epitope is part of the peptide or is a non-chelate chemical hapten, recognition of the metal-chelate complex is no longer an issue.

Particularly useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$Bi, and $^{225}$Ac for radio-imaging and RAIT. The same chelators, when complexed with non-radioactive metals such as Mn, Fe and Gd for use with MRI, when used along with the bsAbs of the invention. Macrocyclic chelators such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelators may be used with numerous radiometals, and are also useful as certain cold metal complexes for bsAb-directed immunophototherapy. Also, more than one type of chelator may be conjugated to the targetable construct to bind multiple metal ions, e.g., cold ions, diagnostic radionuclides and/or therapeutic radionuclides.

Particularly useful diagnostic radionuclides that can be bound to the chelating agents of the targetable construct include, but are not limited to, $^{111}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$Br, $^{75}$Br, $^{76}$Br, $^{82m}$Rb, $^{83}$Sr, or other gamma-, beta-, or positron-emitters. Preferably, the diagnostic radionuclides include a decay energy in the range of 25 to 10,000 keV, more preferably in the range of 25 to 4,000 keV, and even more preferably in the range of 20 to 1,000 keV, and still more preferably in the range of 70 to 700 keV. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV.

Particularly useful therapeutic radionuclides that can be bound to the chelating agents of the targetable construct include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$i, $^{32}$P, $^{33}$P, $^{47}$Sc, $^{111}$Ag, $^{67}$Ga, $^{142}$Pr, $^{153}$Sm, $^{161}$Tb, $^{66}$Dy, $^{166}$Ho, $^{86}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 25 to 10,000 keV. Decay energies of useful beta-particle-emitting nuclides are preferably 25-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-9,000 keV, more preferably 3,000-8,000 keV, and most preferably 4,000-7,000 keV.

Chelators such as those disclosed in U.S. Pat. No. 5,753, 206, especially thiosemi-carbazonylglyoxylcysteine(Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a hard acid chelator like DTPA for In(III) cations, and a soft acid chelator (e.g, thiol-containing chelator such as Tscg-Cys) for Tc cations. Because antibodies to a di-DTPA hapten are known (Barbet '395, supra) and are readily coupled to a targeting antibody to form a bsAb, it is possible to use a peptide hapten with cold di-DTPA chelator and another chelator for binding a radioisotope, in a pretargeting protocol, for targeting the radioisotope. One example of such a peptide is Ac-Lys(DTPA)-Tyr-Lys(DTPA)-Lys(Tscg-Cys)-NH$_2$ (SEQ ID NO: 7). This peptide can be preloaded with In(III) and then labeled with 99-m-Tc cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the linker, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker for eventual capture by a pretargeted bsAb.

Preferred chelators include NOTA, DOTA and Tscg and combinations thereof. These chelators have been incorporated into a chelator-peptide conjugate motif as exemplified in the following constructs:

(a) DOTA-Phe-Lys(HSG)-D-Tyr-Lys(HSG)-NH$_2$ (SEQ ID NO: 3);

(b) DOTA-Phe-Lys(HSG)-Tyr-Lys(HSG)-NH$_2$ (SEQ ID NO: 2);

(c) Ac-Lys(HSG)-D-Tyr-Lys(HSG)-Lys(Tscg-Cys)-NH$_2$ (SEQ ID NO: 4);

(d) DOTA-Phe-Lys(HSG)-D-Tyr-Lys(HSG)-Lys(Tscg-Cys)-NH$_2$ (SEQ ID NO: 1);

(e) (Tscg-Cys)-Phe-Lys(HSG)-D-Tyr-Lys(HSG)-Lys(DOTA)-NH$_2$ (SEQ ID-NO: 1);

(f)

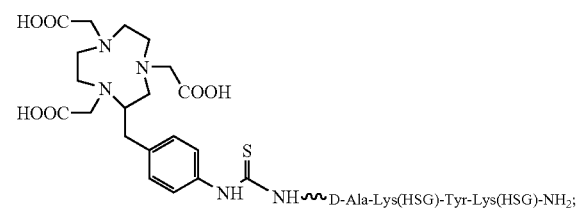

and
(SEQ ID NO: 5)
(g)

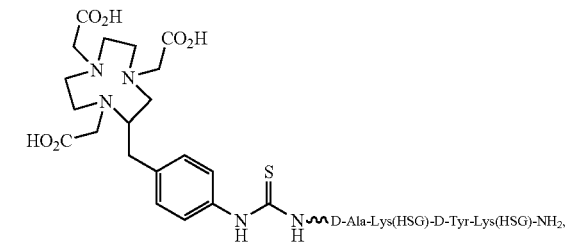

(SEQ ID NO: 6)

The chelator-peptide conjugates (f) and (g), above, has been shown to bind $^{68}$Ga and is thus useful in positron emission tomography (PET) applications.

Chelators are coupled to the peptides of the targetable construct using standard chemistries, some of which are discussed more fully in the working examples below. Briefly, the synthesis of the peptide Ac-Lys(HSG)-D-Tyr-Lys(HSG)-Lys (Tscg-Cys)-NH$_2$ (SEQ ID NO: 4) was accomplished by first attaching Aloc-Lys(Fmoc)-OH to a Rink amide resin on the peptide synthesizer. The protecting group abbreviations "Aloc" and "Fmoc" used herein refer to the groups allyloxycarbonyl and fluorenylmethyloxy carbonyl. The Fmoc-Cys (Trt)-OH and TscG were then added to the side chain of the lysine using standard Fmoc automated synthesis protocols to form the following peptide: Aloc-Lys(Tscg-Cys(Trt))-rink resin. The Aloc group was then removed. The peptide synthesis was then continued on the synthesizer to make the following peptide: Lys(Aloc)-D-Tyr-Lys(Aloc)-Lys(Tscg-Cys(Trt))-rink resin (SEQ ID NO: 4). Following N-terminus acylation, and removal of the side chain Aloc protecting groups. The resulting peptide was then treated with activated N-trityl-HSG-OH until the resin gave a negative test for amines using the Kaiser test. See Karacay et al. *Bioconjugate Chem.* 11:842-854 (2000). The synthesis of Ac-Lys(HSG)-D-Tyr-Lys(HSG)-Lys(Tscg-Cys)-$NH_2$ (SEQ ID NO: 4), as well as the syntheses of DOTA-Phe-Lys(HSG)-D-Tyr-Lys(HSG)-$NH_2$ (SEQ ID NO: 3); DOTA-Phe-Lys(HSG)-Tyr-Lys(HSG)-$NH_2$ (SEQ ID NO: 2); DOTA-Phe-Lys(HSG)-D-Tyr-Lys(HSG)-Lys(Tscg-Cys)-$NH_2$ (SEQ ID NO: 1), are described in greater detail below.

IV. General Methods for Preparation of Metal Chelates

Chelator-peptide conjugates may be stored for long periods as solids. They may be metered into unit doses for metal-binding reactions, and stored as unit doses either as solids, aqueous or-semi-aqueous solutions, frozen solutions or lyophilized preparations. They may be labeled by well-known procedures.

Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}InCl_3$, labeling with 99m-Tc(V) glucoheptonate or with Tc cations generated in situ with stannous chloride and Na99m-$TcO_4$ proceeds quantitatively on the soft acid chelator.

Other soft acid cations such as $^{186}Re$, $^{188}Re$, $^{213}Bi$ and divalent or trivalent cations of Mn, Co, Ni, Pb, Cu, Cd, Au, Fe, Ag (monovalent), Zn and Hg, especially $^{64}Cu$ and $^{67}Cu$, and the like, some of which are useful for radioimmunodetection or radioimmunotherapy, can be loaded onto the linker peptide by analogous methods. Re cations also can be generated in situ from perrhenate and stannous ions or a prereduced rhenium glucoheptonate or other transchelator can be used. Because reduction of perrhenate requires more stannous ion (typically above 200 µg/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the Tc-99m. One method for the preparation of ReO metal complexes of the Tscg-Cys-ligands is by reacting the peptide with $ReOCl_3(P(Ph_3)_2$ but it is also possible to use other reduced species such as ReO(ethylenediamine)$_2$.

V. Methods of Administration

It should be noted that much of the discussion presented hereinbelow focuses on the use of the inventive bi-specific antibodies and targetable constructs in the context of treating diseased tissue. The invention contemplates, however, the use of the inventive bi-specific antibodies and targetable constructs in treating and/or imaging normal tissue and organs using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, which are incorporated herein by reference. As used herein, the term "tissue" refers to tissues, including but not limited to, tissues from the ovary, thymus, parathyroid, bone marrow or spleen. An important use when targeting normal tissues is to identify and treat them when they are ectopic (i.e., displaced from their normal location), such as in endometriosis.

The administration of a bsAb and the targetable construct discussed above may be conducted by administering the bsAb at some time prior to administration of the therapeutic agent which is associated with the linker moiety. The doses and timing of the reagents can be readily devised by a skilled artisan, and are dependent on the specific nature of the reagents employed. If a bsAb-F(ab')$_2$ derivative is given first, then a waiting time of 1-6 days before administration of the targetable construct may be appropriate. If an IgG-Fab' bsAb conjugate is the primary targeting vector, then a longer waiting period before administration of the linker moiety may be indicated, in the range of 3-15 days. Alternatively, the bsAb and the targetable construct may be administered substantially at the same time in either a cocktail form or by administering one after the other.

A wide variety of diagnostic and therapeutic reagents can be advantageously conjugated to the targetable construct. Generally, diagnostic and therapeutic agents can include isotopes, drugs, toxins, cytokines, conjugates with cytokines, hormones, growth factors, conjugates, radionuclides, contrast agents, metals, cytotoxic drugs, and immune modulators. For example, gadolinium metal is used for magnetic resonance imaging and fluorochromes can be conjugated for photodynamic therapy. Moreover, contrast agents can be MRI contrast agents, such as gadolinium ions, lanthanum ions, manganese ions, iron, chromium, copper, cobalt, nickel, dysprosium, rhenium, europium, terbium, holmium, neodymium or other comparable label, CT contrast agents, and ultrasound contrast agents. Additional diagnostic agents can include fluorescent labeling compounds such as fluorescein isothiocyanate, rhodamine, phycoerytherin, phycocyanin, allophycocyanin, o-phthaldehyde and fluorescamine, chemiluminescent compounds including luminol, isoluminol, an aromatic acridinium ester, an imidazole, an acridinium salt and an oxalate ester, and bioluminescent compounds including luciferin, luciferase and aequorin. Radionuclides can also be used as diagnostic and/or therapeutic agents, including for example, $^{90}Y$, $^{111}In$, $^{131}I$, $^{99m}Tc$, $^{186}Re$, $^{188}Re$, $^{177}Lu$, $^{67}Cu$, $^{212}Bi$, $^{213}Bi$, and $^{211}At$.

Therapeutic agents also include, for example, chemotherapeutic drugs such as vinca alkaloids, anthracyclines, epidophyllotoxinw, taxanes, antimetabolites, alkylating agents, antibiotics, Cox-2 inhibitors, antimitotics, antiangiogenic and apoptotoic agents, particularly doxorubicin, methotrexate, taxol, CPT-11, camptothecans, and others from these and other classes of anticancer agents. Other useful therapeutic agents for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable therapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable therapeutic agents, such as experimental drugs, are known to those of skill in the art. Therapeutic agents may also include, without limitation, others drugs, prodrugs and/or toxins. The terms "drug," "prodrug," and "toxin" are defined throughout the specification. The terms "diagnostic agent" or "diagnosis" include, but are not limited to, detection agent, detection, or localization.

When the targetable construct includes a diagnostic agent, the bsAb is preferably administered prior to administration of the targetable construct with the diagnostic agent. After sufficient time has passed for the bsAb to target to the diseased tissue, the diagnostic agent is administered, by means of the targetable construct, so that imaging can be performed. Tumors can be detected in body cavities by means of directly or indirectly viewing various structures to which light of the appropriate wavelength is delivered and then collected, or even by special detectors, such as radiation probes or fluorescent detectors, and the like. Lesions at any body site can be viewed so long as nonionizing radiation can be delivered and recaptured from these structures. For example, PET which is a high resolution, non-invasive, imaging technique can be used with the inventive antibodies and targetable constructs for the visualization of human disease. In PET, 511 keV gamma photons produced during positron annihilation decay are detected. X-ray, computed tomography (CT), MRI and gamma imaging (e.g., Single Photon Emission Computed Tomography (SPECT)) may also be utilized through use of a diagnostic agent that functions with these modalities.

As discussed earlier, the targetable construct may include radioactive diagnostic agents that emit 25-10,000 keV gamma-, beta-, alpha- and auger-particles and/or positrons. Examples of such agents include, but are not limited to $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

The present bsAbs or bsFabs can be used in a method of photodynamic therapy (PDT) as discussed in U.S. Pat. Nos. 6,096,289; 4,331,647; 4,818,709; 4,348,376; 4,361,544; 4,444,744; 5,851,527. In PDT, a photosensitizer, e.g., a hematoporphyrin derivative such as dihematoporphyrin ether, is administered to a subject. Anti-tumor activity is initiated by the use of light, e.g., 630 nm. Alternate photosensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (AlSPc) and lutetium texaphyrin (Lutex).

Additionally, in PDT, a diagnostic agent may be injected, for example, systemically, and laser-induced fluorescence can be used by endoscopes including wireless capsule-sized endoscopes or cameras to detect sites of cancer which have accreted the light-activated agent. For example, this has been applied to fluorescence bronchoscopic disclosure of early lung tumors. Doiron et al. *Chest* 76:32 (1979). In another example, the antibodies and antibody fragments can be used in single photon emission. For example, a Tc-99m-labeled diagnostic agent can be administered to a subject following administration of the inventive antibodies or antibody fragments. The subject is then scanned with a gamma camera which produces single-photon emission computed tomographic images and defines the lesion or tumor site.

Therapeutically useful immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), *Photodynamic Therapy of Tumors and Other Diseases* (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. Ultrasound contrast material may also by used including dextran and liposomes, particularly gas-filled liposomes. In one embodiment, an immunomodulator, such as a cytokine, may also be conjugated to the targetable construct by a linker or through other methods known by those skilled in the art. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12 and IL-18), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, interferon-γ, TNF-α, and the like.

The targetable construct may also be conjugated to an enzyme capable of activating a drug/prodrug at the target site or improving the efficacy of a normal therapeutic by controlling the body's detoxification pathways. Following administration of the bsAb, an enzyme conjugated to the targetable construct having a low MW hapten is administered. After the enzyme is pretargeted to the target site by bsAb:targetable construct binding, a cytotoxic drug is injected that is known to act at the target site. The drug may be one which is detoxified by the mammal's ordinary detoxification processes to form an intermediate of lower toxicity. For example, the drug may be converted into the potentially less toxic glucuronide in the liver. The detoxified intermediate can then be reconverted to its more toxic form by the pretargeted enzyme at the target site, and this enhances cytotoxicity at the target site.

Alternatively, an administered prodrug can be converted to an active drug by the pretargeted enzyme. The pretargeted enzyme improves the efficacy of the treatment by recycling the detoxified drug. This approach can be adopted for use with any enzyme-drug pair. Alternatively, the targetable construct with enzyme can be mixed with the targeting bsAb prior to administration to the patient. After a sufficient time has passed for the bsAb:targetable construct-conjugate to localize to the target site and for unbound targetable construct to clear from circulation, a prodrug is administered. As discussed above, the prodrug is then converted to the drug in situ by the pre-targeted enzyme.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in U.S. Pat. No. 5,851,527, to Hansen.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase See, e.g., Arcamone *Cancer Res.* 45:5995 (1985). Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the present invention.

The prodrug CPT-11 (irinotecan) is converted in vivo by carboxylesterase to the active metabolite SN-38. One application of the invention, therefore, is to use a bsAb targeted against a tumor and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the invention. See, e.g., Potter et al., *Cancer Res.* 58:2646-2651 (1998) and Potter et al., *Cancer Res.* 58:3627-3632 (1998).

Etoposide is a widely used cancer drug that is detoxified to a major extent by formation of its glucuronide and is within the scope of the invention. See, e.g., Hande et al. *Cancer Res.* 48:1829-1834 (1988). Glucuronide conjugates can be prepared from cytotoxic drugs and can be injected as therapeutics for tumors pre-targeted with mAb-glucuronidase conjugates. See, e.g., Wang et al. *Cancer Res.* 52:4484-4491 (1992). Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al. *J. Med Chem.* 40:4013-4018 (1997). Other examples of prodrug/enzyme pairs that can be used within the present invention include, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

The enzyme capable of activating a prodrug at the target site or improving the efficacy of a normal therapeutic by controlling the body's detoxification pathways may alternatively be conjugated to the hapten. The enzyme-hapten conjugate is administered to the subject following administration of the pre-targeting bsAb and is directed to the target site. After the enzyme is localized at the target site, a cytotoxic drug is injected, which is known to act at the target site, or a prodrug form thereof which is converted to the drug in situ by the pretargeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processes. The pretargeted enzyme improves the efficacy of the treatment by recycling the detoxified drug. This approach can be adopted for use with any enzyme-drug pair.

In an alternative embodiment, the enzyme-hapten conjugate can be mixed with the targeting bsAb prior to administration to the patient. After a sufficient time has passed for the enzyme-hapten-bsAb conjugate to localize to the target site and for unbound conjugate to clear from circulation, a prodrug is administered. As discussed above, the prodrug is then converted to the drug in situ by the pre-targeted enzyme.

The invention further contemplates the use of the inventive bsAb and the diagnostic agent(s) in the context of Boron Neutron Capture Therapy (BNCT) protocols. BNCT is a binary system designed to deliver ionizing radiation to tumor cells by neutron irradiation of tumor-localized $^{10}$B atoms. BNCT is based on the nuclear reaction which occurs when a stable isotope, isotopically enriched $^{10}$B (present in 19.8% natural abundance), is irradiated with thermal neutrons to produce an alpha particle and a $^{7}$Li nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of $^{10}$B at tumor sites, while leaving non-target organs essentially boron-free. Compositions and methods for treating tumors in subjects using pre-targeting bsAb for BNCT are described in U.S. Pat. No. 6,228,362 and can easily be modified for the purposes of the present invention.

In another embodiment of the present invention, the peptide backbone of the targetable construct is conjugated to a prodrug. The pre-targeting bsAb is administered to the patient and allowed to localize to the target and substantially clear circulation. At an appropriate later time, a targetable construct comprising a prodrug, for example poly-glutamic acid (SN-38-ester)$_{10}$, is given, thereby localizing the prodrug specifically at the tumor target. It is known that tumors have increased amounts of enzymes released from intracellular sources due to the high rate of lysis of cells within and around tumors. A practitioner can capitalize on this fact by appropriately selecting prodrugs capable of being activated by these enzymes. For example, carboxylesterase activates the prodrug poly-glutamic acid (SN-38-ester)$_{10}$ by cleaving the ester bond of the poly-glutamic acid (SN-38-ester)$_{10}$ releasing large concentrations of free SN-38 at the tumor. Alternatively, the appropriate enzyme also can be targeted to the tumor site.

After cleavage from the targetable construct, the drug is internalized by the tumor cells. Alternatively, the drug can-be-internalized as part of an intact complex by virtue of cross-linking at the target. The targetable construct can induce internalization of tumor-bound bsAb and thereby improve the efficacy of the treatment by causing higher levels of the drug to be internalized.

A variety of peptide carriers are well-suited for conjugation to prodrugs, including polyamino acids, such as polylysine, polyglutamic (E) and aspartic acids (D), including D-amino acid analogs of the same, co-polymers, such as poly(Lys-Glu) {poly[KE]}, advantageously from 1:10 to 10:1. Copolymers based on amino acid mixtures such as poly(Lys-Ala-Glu-Tyr (SEQ ID NO: 8) (KAEY; 5:6:2:1) can also be employed. Smaller polymeric carriers of defined molecular weight can be produced by solid-phase peptide synthesis techniques, readily producing polypeptides of from 2-50 residues in chain length. A second advantage of this type of reagent, other than precise structural definition, is the ability to place single or any desired number of chemical handles at certain points in the chain. These can be used later for attachment of recognition and therapeutic haptens at chosen levels of each moiety.

Poly(ethylene) glycol [PEG] has desirable in vivo properties for a bi-specific antibody prodrug approach. Ester linkages between the hydroxyl group of SN-38 and both ends of a standard di-hydroxyl PEG can be introduced by insertion of diacids such as succinic acid between the SN-38 and PEG hydroxyl groups, to generate species such as SN-38-O—CO(CH2)$_2$CO—O-PEG-0-CO(CH2)$_2$CO—OSN-38. The di-SN-38-PEG produced can be considered as the shortest member of the class of SN-38-polymer prodrugs. The desirable in vivo properties of PEG derivatives and the limited loading capacity due to their dimeric functionality led to the preparation of PEG co-polymers having greater hapten-bearing capacity such as those described by Poiani et al. See, e.g., Poiani et al. *Bioconjugate Chem.*, 5:621-630, 1994. PEG derivatives are activated at both ends as their bis(succinimidyl)carbonate derivatives and co-polymerized with multifunctional diamines such as lysine. The product of such co-polymerization, containing (-Lys(COOH)-PEG-Lys(COOH)-PEG-)$_n$ repeat units wherein the lysyl carboxyl group is not involved in the polymerization process, can be used for attachment of SN-38 residues. The SN-38 residues are reacted with the free carboxyl groups to produce SN-38 esters of the (-Lys-(COOH)-PEG-Lys(COOH)-PEG-)$_n$ chain.

Other synthetic polymers that can be used to carry recognition haptens and prodrugs include N-(2-hydroxypropyl)methacrylamide (HMPA) copolymers, poly(styrene-co-maleic acid/anhydride) (SMA), poly(divinylether maleic anhydride) (DIVEMA), polyethyleneimine, ethoxylated polyethylene-imine, starburst dendrimers and poly(N-vinylpyrrolidone) (PVP). As an example, DIVEMA polymer comprised of multiple anhydride units is reacted with a limited amount of SN-38 to produce a desired substitution ratio of drug on the polymer backbone. Remaining anhydride groups are opened under aqueous conditions to produce free carboxylate groups. A limited number of the free carboxylate groups are activated using standard water-soluble peptide coupling agents, e.g. 1-ethyl-3-(3-dimethylaminopropyl)carbodiimide hydrochloride (EDC), and coupled to a recognition moiety bearing a free amino group. An example of the latter is histamine, to which antibodies have been raised in the past.

A variety of prodrugs can be conjugated to the targetable construct. The above exemplifications of polymer use are concerned with SN-38, the active metabolite of the prodrug CPT-11 (irinotecan). SN-38 has an aromatic hydroxyl group that was used in the above descriptions to produce aryl esters susceptible to esterase-type enzymes. Similarly the camptothecin analog topotecan, widely used in chemotherapy, has an available aromatic hydroxyl residue that can be used in a similar manner as described for SN-38, producing esterase-susceptible polymer-prodrugs.

Doxorubicin also contains aromatic hydroxyl groups that can be coupled to carboxylate-containing polymeric carriers using acid-catalyzed reactions similar to those described for the camptothecin family. Similarly, doxorubicin analogs like daunomycin, epirubicin and idarubicin can be coupled in the same manner. Doxorubicin and other drugs with amino 'chemical handles' active enough for chemical coupling to polymeric carriers can be effectively coupled to carrier molecules via these free amino groups in a number of ways. Polymers bearing free carboxylate groups can be activated in situ (EDC) and the activated polymers mixed with doxorubicin to directly attach the drug to the side-chains of the polymer via amide bonds. Amino-containing drugs can also be coupled to amino-pendant polymers by mixing commercially available and cleavable cross-linking agents, such as ethylene glycobis(succinimidylsuccinate) (EGS, Pierce Chemical Co., Rockford, Ill.) or bis-[2-(succinimido-oxycarbonyloxy) ethyl]sulfone (BSOCOES, Molecular Biosciences, Huntsville, Ala.), to cross-link the two amines as two amides after reaction with the bis(succinimidyl) ester groups. This is advantageous as these groups remain susceptible to enzymatic cleavage. For example, (doxorubicin-EGS)$_n$-polylysine remains susceptible to enzymatic cleavage of the diester groups in the EGS linking chain by enzymes such as esterases. Doxorubicin also can be conjugated to a variety of peptides, for example, HyBnK(DTPA)YK(DTPA)-NH$_2$, using established procedures (HyBn=p-H$_2$NNHC$_6$H$_4$CO$_2$H). See Kaneko et al., *J. Bioconjugate Chem.*, 2: 133-141, 1991.

In one preferred embodiment, the therapeutic conjugate comprises doxorubicin coupled to a carrier comprising amine residues and a chelating agent, such as DTPA, to form a DTPA-peptide-doxorubicin conjugate, wherein the DTPA forms the recognition moiety for a pretargeted bsAb. Preferably, the carrier comprises a tyrosyl-lysine dipeptide, e.g., Tyr-Lys(DTPA)-NH$_2$, and more preferably still it comprises Lys(DTPA)-Tyr-Lys(DTPA)-NH$_2$. Doxorubicin phenyl hydrazone conjugates to bis-DPTA containing peptides are particularly desirable in a therapeutic context.

Methotrexate also has an available amino group for coupling to activated carboxylate-containing polymers, in a similar manner to that described for doxorubicin. It also has two glutamyl carboxyl groups (alpha and gamma) that can be activated for coupling to amino-group containing polymers. The free carboxylate groups of methotrexate can be activated in situ (EDC) and the activated drug mixed with an amino-containing polymer to directly attach the drug to the side-chains of the polymer via amide bonds. Excess unreacted or cross-reacted drug is separated readily from the polymer-drug conjugate using size-exclusion or ion-exchange chromatography.

Maytansinoids and calicheamicins (such as esperamycin) contain mixed di- and tri-sulfide bonds that can be cleaved to generate species with a single thiol useful for chemical manipulation. The thiomaytensinoid or thioespera-mycin is first reacted with a cross-linking agent such as a maleimido-peptide that is susceptible to cleavage by peptidases. The C-terminus of the peptide is then activated and coupled to an amino-containing polymer such as polylysine.

In still other embodiments, the bi-specific antibody-directed delivery of therapeutics or prodrug polymers to in vivo targets can be combined with bi-specific antibody delivery of radionuclides, such that combination chemotherapy and radioimmunotherapy is achieved. Each therapy can be conjugated to the targetable construct and administered simultaneously, or the nuclide can be given as part of a first targetable construct and the drug given in a later step as part of a second targetable construct. In one simple embodiment, a peptide containing a single prodrug and a single nuclide is constructed. For example, the tripeptide Ac-Glu-Gly-Lys-NH$_2$ can be used as a carrier portion of a targetable construct, whereby SN-38 is attached to the gamma glutamyl carboxyl group as an aryl ester, while the chelate DOTA is attached to the epsilon amino group as an amide, to produce the complex Ac-Glu(SN-38)-Gly-Lys(DOTA)-NH$_2$. The DOTA chelate can then be radiolabeled with various metals for imaging and therapy purposes including In-11, Y-90, Sm-153, Lu-177 and Zr-89. As the metal-DOTA complex may represent the recognizable hapten on the targetable construct, the only requirement for the metal used as part of the DOTA complex is that the secondary recognition antibody also used recognizes that particular metal-DOTA complex at a sufficiently high affinity. Generally, this affinity (log $K_a$) is between 6-11. Polymeric peptides such as poly[Glu(SN-38)$_{10}$-Lys(Y-90-DOTA)$_2$] can be given as readily as the more chemically defined lower MW reagent above, and are indeed preferred. Also, triply substituted polymers can be used, such as poly[Glu(Sn-38)$_{10}$-Lys (Y-90-DOTA)$_n$(histamine-succinate)$_m$, where n and m are integers, such that the recognition agent is independent of the radioimmunotherapy agent. The prodrug is activated by carboxylesterases present at the tumor site or by carboxylesterases targeted to the site using a second targetable construct.

Alternatively, a combination therapy can be achieved by administering the chemotherapy and radioimmunotherapy agents in separate steps. For example, a patient expressing CEA-tumors is first administered bsAb with at least one arm which specifically binds CEA and at least one other arm which specifically binds the targetable construct whose hapten is a conjugate of yttrium-DOTA. Later the patient is treated with a targetable construct comprising a conjugate of yttrium-DOTA-beta-glucuronidase. After sufficient time for bsAb and enzyme localization and clearance, a second targetable construct, comprising Ac-Glu(SN-38)-Gly-Lys(Y-90-DOTA)-NH$_2$, is given. The second targetable construct localizes to the tumor by virtue of bsAb at the tumor that are not already bound to a first targetable construct. First targetable constructs which are localized to the target site act on the Ac-Glu(SN-38)-Gly-Lys(Y-90-DOTA)-NH$_2$ to liberate the free SN-38 drug. Localization of both the prodrug and its respective enzyme to the target site enhances the production of active drug by ensuring that the enzyme is not substrate limited. This embodiment constitutes a marked improvement of current prodrug methodologies currently practiced in the art.

Another advantage of administering the prodrug-polymer in a later step, after the nuclide has been delivered as part of a previously given targetable construct, is that the synergistic effects of radiation and drug therapy can be manipulated and, therefore, maximized. It is hypothesized that tumors become more 'leaky' after RAIT due to radiation damage. This can allow a polymer-prodrug to enter a tumor more completely and deeply. This results in improved chemotherapy.

Alternatively, the RAIT therapy agent can be attached to bsAb rather than to the targetable construct. For example, an anti-CEA x anti-DTPA bsAb conjugated to Y-90-DOTA is administered first to a patient with CEA-expressing tumors. In this instance, advantage is taken of the selectivity of certain anti-chelate mabs in that an anti-indium-DTPA antibody do not bind to a yttrium-DOTA chelate. After the Y-90-DOTA-anti-CEA×anti-indium-DTPA has maximized at the tumor and substantially cleared non-target tissue, a conjugate of indium-DTPA-glucuronidase is injected and localized specifically to the CEA tumor sites. The patient is then injected with a polymer-prodrug such as poly(Glu)(SN-38)$_{10}$. The latter is cleaved selectively at the tumor to active monomeric SN-38, successfully combining chemotherapy with the previously administered RAIT.

It should also be noted that a bi-specific antibody or antibody fragment can be used in the present method, with at least one binding site specific to an antigen at a target site and at least one other binding site specific to the enzyme component of the antibody-enzyme conjugate. Such an antibody can bind the enzyme prior to injection, thereby obviating the need to covalently conjugate the enzyme to the antibody, or it can be injected, and localized at the target site and, after non-targeted antibody has substantially cleared from the circulatory system of the mammal, enzyme can be injected in an amount and by a route which enables a sufficient amount of the enzyme to reach a localized antibody or antibody fragment and bind to it to form the antibody-enzyme conjugate in situ.

It should also be noted that the invention also contemplates the use of multivalent target binding proteins which have at least three different target binding sites as described in patent Appl. Ser. No. 60/220,782. Multivalent target binding proteins have been made by cross-linking several Fab-like fragments via chemical linkers. See U.S. Pat. Nos. 5,262,524; 5,091,542 and Landsdorp et al., *Euro. J. Immunol.* 16: 679-83 (1986). Multivalent target binding proteins also have been made by covalently linking several single chain Fv molecules (scFv) to form a single polypeptide. See U.S. Pat. No. 5,892, 020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al., *Protein Engineering* 10(4): 423-433 (1997).

A clearing agent may be used which is given between doses of the bsAb and the targetable construct. The present inventors have discovered that a clearing agent of novel mechanistic action may be used with the invention, namely a glycosylated anti-idiotypic Fab' fragment targeted against the disease targeting arm(s) of the bsAb. Anti-CEA (MN-14 Ab)×anti-peptide bsAb is given and allowed to accrete in disease targets to its maximum extent. To clear residual bsAb, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the therapeutic or diagnostic agent which is associated with the targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety.

In accordance with yet another aspect of the present invention, the present invention provides a kit suitable for treating or identifying diseased tissues in a patient, comprising a bi-specific antibody or antibody fragment having at least one arm that specifically binds a targeted tissue and at least one other arm that specifically binds a targetable construct, a first targetable construct which comprises a carrier portion which comprises or bears at least one epitope recognizable by the at least one other arm of the bi-specific antibody or antibody fragment, and one or more conjugated therapeutic or diagnostic agents, or enzymes, and, optionally, a clearing composition useful for clearing non-localized antibodies and antibody fragments. The kit may optionally contain a prodrug when the first targetable construct comprises an enzyme capable of converting the prodrug to a drug at the target site, an enzyme that is capable of reconverting a detoxified intermediate of a drug to a toxic form, and, therefore, of increasing the toxicity of the drug at the target site, or an enzyme capable of reconverting a prodrug which is activated in the patient through natural processes and is subject to detoxification by conversion to an intermediate of lower toxicity from the detoxified intermediate to a toxic form, and, therefore, of increasing the toxicity of the drug at the target site. A second targetable construct may also be used which comprises a carrier portion which comprises or bears at least one epitope recognizable by the at least one other arm of the bi-specific antibody or antibody fragment, and a prodrug, when the enzyme is capable of converting the prodrug to a drug at the target site. Instruments which facilitate identifying or treating diseased tissue also can be included in the kit. Examples include, but are not limited to application devices, such as syringes. Solutions required for utilizing the disclosed invention for identifying or treating diseased tissue also can be included in the kit.

The targetable construct may be administered intravenously, intraarterially, intraoperatively, endoscopically, intraperitoneally, intramuscularly, subcutaneously, intrapleurally, intrathecally, by perfusion through a regional catheter, or by direct intralesional injection, and can be by continuous infusion or by single or multiple boluses. or through other methods known to those skilled in the art for diagnosing (detecting) and treating diseased tissue. Further, the targetable construct may include agents for other methods of detecting and treating diseased tissue including, without limitation, conjugating dextran or liposome formulations to the targetable construct for use with ultrasound, or other contrast agents for use with other imaging modalities, such as X-ray, CT, PET, SPECT and ultrasound, as previously described.

VI. Methods for Raising Antibodies

Abs to peptide backbones and/or haptens are generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

The antibodies used in the present invention are specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744. See also U.S. Pat. No. 5,965,132, to Thorpe et al., U.S. Pat. No. 6,004,554, to Thorpe et al., U.S. Pat. No. 6,071,491, to Epstein et al., U.S. Pat. No. 6,017,514, to Epstein et al., U.S. Pat. No. 5,882,626, to Epstein et al., U.S. Pat. No. 5,019,368, to Epstein et al., and U.S. Pat. No. 6,342,221, to Thorpe et al., all of which are incorporated herein by reference.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as disclosed in U.S. Pat. Nos. 4,361, 644 and 4,444,744. Markers of tumor vasculature (e.g., VEGF), of tumor necrosis (Epstein patents), of membrane receptors (e.g., folate receptor, EGFR), of transmembrane antigens (e.g., PSMA), and of oncogene products can also serve as suitable tumor-associated targets for antibodies or antibody fragments. Markers of normal cell constituents which are expressed copiously on tumor cells, such as B-cell complex antigens (e.g., CD19, CD20, CD21, CD22, CD23, and HLA-DR on B-cell malignancies), as well as cytokines expressed by certain tumor cells (e.g., IL-2 receptor in T-cell malignancies) are also suitable targets for the antibodies and antibody fragments of this invention. Other well-known tumor associated antigens that can be targeted by the antibodies and antibody fragments of this invention include, but are not limited to, CEA, CSAp, TAG-72, MUC-1, MUC-2, MUC-3, MUC4, EGP-1, EGP-2, BrE3, PAM-4, KC-4, A3, KS-1, PSMA, PSA, tenascin, T101, S100, MAGE, HLA-DR, CD19, CD20, CD22, CD30, and CD74.

Another marker of interest is transmembrane activator and CAML-interactor (TACI). See Yu et al. *Nat. Immunol.* 1:252-256 (2000). Briefly, TACI is a marker for B-cell malignancies (e.g., lymphoma). Further it is known that TACI and B-cell maturation antigen (BCMA) are bound by the tumor necrosis factor homolog a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine inmunoglobulin variable domains are described, for example, by the publication of Orlandi et al., *Proc. Nat'l Acad. Sci. USA* 86: 3833 (1989), which is incorporated by reference in its entirety. Techniques for producing humanized Mabs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit.*

*Rev. Biotech.* 12: 437 (1992), and Singer et al., *J. Immun.* 150: 2844 (1993), each of which is hereby incorporated by reference.

Alternatively, fully human antibodies can be obtained from transgenic non-human animals. See, e.g., Mendez et al., *Nature Genetics*, 15: 146-156 (1997); U.S. Pat. No. 5,633,425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics*, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial inmunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for-producing a human immunoglobulin phage library can be obtained, for example, from STRATAGENE Cloning Systems (La Jolla, Calif.).

A similar strategy can be employed to obtain high-affinity scFv. See, e.g., Vaughn et al., *Nat. Biotechnol.*, 14: 309-314 (1996). An scFv library with a large repertoire can be constructed by isolating V-genes from non-immunized human donors using PCR primers corresponding to all known $V_H$, $V_\kappa$ and $V_\lambda$ gene families. Following amplification, the $V_\kappa$ and $V_\lambda$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., *Biotechnology*, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J. Cancer*, 78: 181-188 (1998); Osbourn et al., *Immunotechnology*, 2: 181-196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

The bsAbs can be prepared by techniques known in the art, for example, an anti-CEA tumor Ab and an anti-peptide Ab are both separately digested with pepsin to their respective F(ab')$_2$s. The anti-CEA-Ab-F(ab')$_2$ is reduced with cysteine to generate Fab' monomeric units which are further reacted with the cross-linker bis(maleimido) hexane to produce Fab'-maleimide moieties. The anti-peptide Ab-F(ab')$_2$ is reduced with cysteine and the purified, recovered anti-peptide Fab'-SH reacted with the anti-CEA-Fab'-maleimide to generate the Fab'×Fab' bi-specific Ab. Alternatively, the anti-peptide Fab'-SH fragment may be coupled with the anti-CEA F(ab')$_2$ to generate a F(ab')$_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce bi-specific antibodies and antibody fragments. For example, bi-specific antibodies and antibody fragments can be produced in the milk of transgenic livestock. See, e.g., Colman, A., *Biochem. Soc. Symp.*, 63: 141-147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bsAbs include engineered recombinant Abs which have additional cysteine residues so that they crosslink more strongly than the more common inmunoglobulin isotypes. See, e.g., FitzGerald et al., Protein Eng. 10(10): 1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., *Proc. Natl. Acad. Sci.*, 92: 7021-7025, 1995. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4\text{-}Ser_1)_3$ linker (SEQ ID NO: 9), and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into Chinese hamster ovary cells. Bi-specific fusion proteins are prepared in a similar manner. Bi-specific single-chain antibodies and bi-specific fusion proteins are included within the scope of the present invention.

Bi-specific fusion proteins linking two or more different single-chain antibodies or antibody fragments are produced in similar manner.

Recombinant methods can be used to produce a variety of fusion proteins. For example a fusion protein comprising a Fab fragment derived from a humanized monoclonal anti-CEA antibody and a scFv derived from a murine anti-diDTPA can be produced. A flexible linker, such as GGGS (SEQ ID NO: 10) connects the scFv to the constant region of the heavy chain of the anti-CEA antibody. Alternatively, the scFv can be connected to the constant region of the light chain of hMN-14. Appropriate linker sequences necessary for the in-frame connection of the heavy chain Fd to the scFv are introduced into the $V_L$ and $V_K$ domains through PCR reactions. The DNA fragment encoding the scFv is then ligated into a staging vector containing a DNA sequence encoding the $C_H1$ domain. The resulting scFv-$C_H1$ construct is excised and ligated into a vector containing a DNA sequence encoding the $V_H$ region of an anti-CEA antibody. The resulting vector can be used to transfect mammalian cells for the expression of the bi-specific fusion protein.

Large quantities of bscAb and fusion proteins can be produced using *Escherichia coli* expression systems. See, e.g., Zhenping et al., *Biotechnology*, 14: 192-196, 1996. A functional bscAb can be produced by the coexpression in *E. coli* of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the *E. coli* alkaline phosphatase promoter which is inducible by phosphate starvation. Alternatively, single-chain fusion constructs have successfully been expressed in *E. coli* using the lac promoter and a medium consisting of 2% glycine and 1% Triton X-100. See, e.g., Yang et al., *Appl. Environ. Microbiol.*, 64: 2869-2874, 1998. An *E. coli*, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., *Staphylococcal* protein A chromatography.

Functional bscAb and fusion proteins also can be produced in the milk of transgenic livestock. See, e.g., Colman, A., *Biochem. Soc. Symp.,* 63: 141-147, 1998; U.S. Pat. No. 5,827,690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, manmmalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.,* 13: 1090-1093, 1995; Fiedler et al., *Immunotechnology,* 3: 205-216, 1997. Such production offers several advantages including low cost, large scale output, and stable, long term storage. The bscAb fragment, obtained as described above, is cloned into an expression vector containing a promoter sequence and encoding a signal peptide sequence, to direct the protein to the endoplasmic recticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods,* 212: 149-160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.,* 42: 177 (1988); Bei et al., *J. Immunol. Methods,* 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods,* 212: 149-160 (1998). The bscAb fragment, obtained as described above, is cloned into an expression vector containing the *Drosphila* metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

Preferred bi-specific antibodies of the instant invention are those which incorporate the Fv of MAb Mu-9 and the Fv of MAb 679 or the Fv of MAb MN-14 and the Fv of MAb 679, and their human, chimerized or humanized counterparts. The MN-14, as well as its chimerized and humanized counterparts, are disclosed in U.S. Pat. No. 5,874,540. Also preferred are bi-specific antibodies which incorporate one or more of the CDRs of Mu-9 or 679. The antibody can also be a fusion protein or a bi-specific antibody that incorporates a Class-III anti-CEA antibody and the Fv of 679. Class-III antibodies, including Class-III anti-CEA are discussed in detail in U.S. Pat. No. 4,818,709.

VII. Other Applications

The present invention encompasses the use of the bsAb and a therapeutic or diagnostic agent associated with the targetable construct discussed above in intraoperative, intravascular, and endoscopic tumor and lesion detection, biopsy and therapy as described in U.S. Pat. No. 6,096,289.

The antibodies and antibody fragments of the present invention can be employed not only for therapeutic or imaging purposes, but also as aids in performing research in vitro. For example, the bsAbs of the present invention can be used in vitro to ascertain if a targetable construct can form a stable complex with one or more bsAbs. Such an assay would aid the skilled artisan in identifying targetable constructs which form stable complexes with bsAbs. This would, in turn, allow the skilled artisan to identify targetable constructs which are likely to be superior as therapeutic and/or imaging agents.

The assay is advantageously performed by combining the targetable construct in question with at least two molar equivalents of a bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96-well plate. To each well, is added solutions of targetable construct(s). Following incubation and analysis, one can readily determine which construct(s) bind(s) best to which bsAb(s).

It should be understood that the order of addition of the bsAb to the targetable construct is not crucial; that is, the bsAb may be added to the construct and vice versa. Likewise, neither the bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, high-field NMR or other appropriate method in conjunction with, or in place of, size-exclusion HPLC.

The present invention is further illustrated by, though in no way limited to, the following examples.

EXAMPLES

Example 1

Synthesis of Ac-Lys(HSG)-D-Tyr-Lys(HSG)-Lys (Tscg-Cys-)-NH$_2$ (IMP 243)

The peptide was synthesized as described by Karacay et. al. *Bioconjugate Chem.* 11:842-854 (2000) except D-tyrosine was used in place of the L-tyrosine and the N-trityl-HSG-OH was used in place of the DTPA. The final coupling of the N-trityl-HSG-OH was carried out using a ten fold excess of N-trityl-HSG-OH relative to the peptide on the resin. The N-trityl-HSG-OH (0.28 M in NMP) was activated using one equivalent (relative to HSG) of N-hydroxybenzotriazole, one equivalent of benzotrazole-1-yl-oxy-tris-(dimethylamino) phosphonium hexafluorophosphate (BOP) and two equivalents of diisopropylethylamine. The activated substrate was mixed with the resin for 15 hr at room temperature.

Example 2

Tc-99m Kit Formulation Comprising IMP 243

A formulation buffer was prepared which contained 22.093 g hydroxypropyl-β-cyclodextrin, 0.45 g 2,4-dihydroxybenzoic acid, 0.257 g acetic acid sodium salt, and 10.889 g α-D-glucoheptonic acid sodium salt dissolved in 170 mL nitrogen degassed water. The solution was adjusted to pH 5.3 with a few drops of 1 M NaOH then further diluted to a total volume of 220 mL. A stannous buffer solution was prepared by diluting 0.2 mL of SnCl$_2$ (200 mg/mL) with 3.8 mL of the formulation buffer. The peptide Ac-Lys(HSG)-D-Tyr-Lys(HSG)-Lys(Tscg-Cys)-NH$_2$ (SEQ ID NO: 4) (0.0026 g), was dissolved in 78 mL of the buffer solution and mixed with 0.52 mL of the stannous buffer. The peptide solution was then filtered through a 0.22 μm Millex GV filter in 1.5 mL aliquots into 3 mL lyophilization vials. The filled vials were frozen immediately, lyophilized and crimp sealed under vacuum.

Pertechnetate solution (27 mCi) in 1.5 mL of saline was added to the kit. The kit was incubated at room temperature for 10 min and heated in a boiling water bath for 25 min. The kit was cooled to room temperature before use.

Example 3

Peptides for Carrying Therapeutic/Imaging Radioisotopes to Tumors Via Bi-Specific Antibody Tumor Pretargeting DOTA-Phe-Lys(HSG)-Tyr-Lys(HSG)-NH$_2$ (SEQ ID NO: 2) (IMP 237) was synthesized to deliver therapeutic radioisotopes such as $^{90}$Y or $^{177}$Lu to tumors via bi-specific antibody tumor pretargeting. The bi-specific antibody is composed of one portion which binds to an antigen on the tumor and another portion which binds to the HSG peptide. The antibody which binds the HSG peptide is 679. This system can also be used to deliver imaging isotopes such as $^{111}$In-111.

Synthesis of IMP 237

IMP 237 was synthesized on Sieber Amide resin (NovaBiochem) using standard Fmoc based solid phase peptide synthesis to assemble the peptide backbone with the following protected amino acids, in order: Fmoc-Lys(Aloc)-OH, Fmoc-Tyr(But)-OH, Fmoc-Lys(Aloc)-OH, Fmoc-Phe-OH, (Reagents from Advanced Chemtech) tri-t-butyl DOTA (Macrocyclics). The side lysine side chains were then deprotected with Pd[P(Ph)$_3$]$_4$ by the method of Dangles et. al. *J. Org. Chem.* 52:4984-4993 (1987). The HSG ligands were then added as Trityl HSG (synthesis described below) using the BOP/HBTU double coupling procedure used to attach the amino acids. The peptide was cleaved from the resin and the protecting groups were removed by treatment with TFA. The peptide was purified by HPLC to afford 0.6079 g of peptide from 1.823 g of Fmoc-Lys(Aloc)-Tyr(But)-Lys(Aloc)-NH-Sieber amide resin.

Synthesis of N-Trityl-HSG-OH

Glycine t-butyl ester hydrochloride (15.263 g, 9.1×10$^{-2}$ mol) and 19.760 g Na$_2$CO$_3$ were mixed, then suspended in 50 mL H$_2$O and cooled in an ice bath. Succinic anhydride (9.142 g, 9.14×10$^{-2}$ mol) was then added to the reaction solution which was allowed to warm slowly to room temperature and stir for 18 hr. Citric acid (39.911 g) was dissolved in 50 mL H$_2$O and slowly added to the reaction solution and then extracted with 2×150 mL EtOAc. The organic extracts were dried over Na$_2$SO$_4$, filtered and concentrated to afford 25.709 g of a white solid.

The crude product (25.709 g) was dissolved in 125 mL dioxane, cooled in a room temperature water bath and mixed with 11.244 g of N-hydroxysuccinimide. Diisopropylcarbodiimide 15.0 mL was added to the reaction solution which was allowed to stir for one hour. Histamine dihydrochloride (18.402 g, 1.00×10$^{-1}$ mol) was then dissolved in 100 mL DMF and 35 mL diisopropylethylamine. The histamine mixture was added to the reaction solution which was stirred at room temperature for 21 hr. The reaction was quenched with 100 mL water and filtered to remove a precipitate. The solvents were removed under hi-vacuum on the rotary evaporator. The crude product was dissolved in 300 mL dichloromethane and extracted with 100 mL saturated NaHCO$_3$. The organic layer was dried over Na$_2$SO$_4$ and concentrated to afford 34.19 g of crude product as a yellow oil.

The crude product (34.19 g) was dissolved in 50 mL chloroform and mixed with 31 mL diisopropylethylamine. Triphenylmethyl chloride (25.415 g) was dissolved in 50 ml chloroform and added dropwise to the stirred reaction solution which was cooled in an ice bath. The reaction was stirred for 45 min and then quenched with 100 mL H$_2$O. The layers were separated and the organic solution was dried over Na$_2$SO$_4$ and concentrated to form a green gum. The gum was triturated with 100 mL Et$_2$O to form a yellow precipitate which was washed with 3×50 mL portions of Et$_2$O. The solid was vacuum dried to afford 30.641 g (59.5% overall yield) of N-trityl-HSG-t-butyl ester.

N-trityl-HSG-t-butyl ester (20.620 g, 3.64×10$^{-2}$ mol) was dissolved in a solution of 30 mL chloroform and 35 mL glacial acetic acid. The reaction was cooled in an ice bath and 15 mL of BF$_3$.Et$_2$O was slowly added to the reaction solution. The reaction was allowed to warm slowly to room temperature and mix for 5 hr. The reaction was quenched by pouring into 200 mL 1M NaOH and the product was extracted with 200 mL chloroform. The organic layer was dried over Na$_2$SO$_4$ and concentrated to afford a crude gum which was triturated with 100 mL Et$_2$O to form a precipitate. The crude precipitate was poured into 400 mL 0.5 M pH 7.5 phosphate buffer and extracted with 2×200 mL EtOAc. The aqueous layer was acidified to pH 3.5 with 1 M HCl and extracted with 2×200 mL chloroform. A precipitate formed and was collected by filtration (8.58 g). The precipitate was the desired product by HPLC comparison to a previous sample (ESMS MH+511).

Radiolabeling $^{90}$Y Kit Preparation

DOTA-Phe-Lys(HSG)-Tyr-Lys(HSG)-NH$_2$ (SEQ ID NO: 2) was dissolved in 0.25 M NH$_4$OAc/10% HPCD buffer at concentrations of 9, 18, 35, 70 and 140 μg/mL. The solutions were sterile filtered through a 0.22 μm Millex GV filter in one mL aliquots into acid washed lyophilization vials. The filled vials were frozen immediately on filling and lyophilized. When the lyophilization cycle was complete the vials were sealed under vacuum and crimp sealed upon removal from the lyophilizer.

The 90Y (~400 μCi/kit) was diluted to 1 mL in deionized water and added to the lyophilized kits. The kits were heated in a boiling water bath for 15 min, the vials were cooled to room temperature and the labeled peptides were evaluated by reverse phase HPLC (HPLC conditions: Waters Nova-Pak C-18, 8×100 mm RCM column eluted at 3 mL/min with a linear gradient from 100% (0.1% TFA in H$_2$O) to 100% (90% CH$_3$CN, 0.1% TFA, 10% H$_2$O)). The HPLC analysis revealed that the minimum concentration of peptide needed for complete labeling, with this formulation, was 35 μg/mL. The reverse phase HPLC trace showed a sharp $^{90}$Y labeled peptide peak. The labeled peptide was completely bound when mixed with excess 679 IgG by size exclusion HPLC.

Labeling with $^{111}$In

The $^{111}$In (~300 μCi/kit) was diluted to 0.5 mL in deionized water and added to the lyophilized kits. The kits were heated in a boiling water bath for 15 min, the vials were cooled and 0.5 mL of 2.56×10$^{-5}$ M In in 0.5 M acetate buffer was added and the kits were again heated in the boiling water bath for 15 min. The labeled peptide vials were cooled to room temperature and evaluated by reverse phase HPLC (HPLC conditions: Waters Nova-Pak C-18, 8×100 mm RCM column eluted at 3 mL/min with a linear gradient from 100% (0.1% TFA in H$_2$O) to 100% (90% CH$_3$CN, 0.1% TFA, 10% H$_2$O)). The HPLC analysis revealed that the minimum concentration of peptide needed for labeling (4.7% loose $^{111}$In), with this formulation, was 35 μg/mL. The reverse phase HPLC trace showed a sharp $^{111}$In labeled peptide peak. The labeled peptide was completely bound when mixed with excess 679 IgG by size exclusion HPLC.

In-Vivo Studies

Nude mice bearing GW-39 human colonic xenograft tumors (100-500 mg) were injected with the bi-specific antibody hMN-14×m679 (1.5×10$^{-10}$ mol). The antibody was allowed to clear for 24 hr before the $^{111}$In labeled peptide (8.8 μCi, 1.5×10$^{-11}$ mol) was injected. The animals were sacrificed at 3, 24, 48 hr post injection.

The results of the biodistribution studies of the peptide in the mice pretargeted with hMN-14×m679 are shown in Table 1. The tumor to non-tumor ratios of the peptides in the pretargeting study are show in Table 2.

TABLE 1

Pretargeting With $^{111}$In Labeled Peptide 24 hr After Injection of hMN-14 × m679 % Injected/g Tissue

| Tissue | 3 hr After $^{111}$In IMP 237 | 24 hr After $^{111}$In IMP 237 | 48 hr After $^{111}$In IMP 237 |
|---|---|---|---|
| GW-39 | 7.25 ± 2.79 | 8.38 ± 1.70 | 5.39 ± 1.46 |
| Liver | 0.58 ± 0.13 | 0.62 ± 0.09 | 0.61 ± 0.16 |
| Spleen | 0.50 ± 0.14 | 0.71 ± 0.16 | 0.57 ± 0.15 |
| Kidney | 3.59 ± 0.75 | 2.24 ± 0.40 | 1.27 ± 0.33 |
| Lungs | 1.19 ± 0.26 | 0.44 ± 0.10 | 0.22 ± 0.06 |
| Blood | 2.42 ± 0.61 | 0.73 ± 0.17 | 0.17 ± 0.06 |
| Stomach | 0.18 ± 0.03 | 0.09 ± 0.02 | 0.07 ± 0.02 |
| Sm. Int. | 0.65 ± 0.74 | 0.18 ± 0.03 | 0.11 ± 0.02 |
| Lg. Int. | 0.30 ± 0.07 | 0.17 ± 0.03 | 0.13 ± 0.03 |

TABLE 2

Pretargeting With $^{111}$In Labeled Peptides 24 hr After Injection of hMN-14 × m679 Tumor/Non-Tumor Tissue Ratios

| Tissue | 3 hr After $^{111}$In IMP 237 | 24 hr After $^{111}$In IMP 237 | 48 hr After $^{111}$In IMP 237 |
|---|---|---|---|
| Liver | 12.6 ± 4.44 | 13.6 ± 2.83 | 8.88 ± 1.78 |
| Spleen | 15.1 ± 6.32 | 12.1 ± 2.86 | 9.50 ± 1.62 |
| Kidney | 2.04 ± 0.74 | 3.84 ± 1.04 | 4.25 ± 0.19 |
| Lungs | 6.11 ± 1.96 | 19.6 ± 5.91 | 25.4 ± 6.00 |
| Blood | 3.04 ± 1.13 | 11.9 ± 3.20 | 31.9 ± 4.79 |
| Stomach | 40.5 ± 16.5 | 104. ± 39.6 | 83.3 ± 16.5 |
| Sm. Int. | 18.9 ± 12.6 | 47.5 ± 10.3 | 49.5 ± 7.83 |
| Lg. Int. | 25.2 ± 10.6 | 50.1 ± 16.7 | 43.7 ± 9.35 |

Serum Stability of DOTA-Phe-Lys(HSG)-Tyr-Lys(HSG)-NH$_2$ (SEQ ID NO: 2) (IMP 237) and DOTA-Phe-Lys(HSG)-D-Tyr-Lys(HSG)-NH$_2$ (SEQ ID NO: 3) (IMP 241)

Peptide Labeling and HPLC Analysis

The peptides, IMP 237 and IMP 241, were labeled according to the procedure described by Karacay et. al. *Bioconjugate Chem.* 11:842-854 (2000). The peptide, IMP 241 (0.0019 g), was dissolved in 587 μl 0.5 M NH$_4$Cl, pH 5.5. A 1.7 μL aliquot of the peptide solution was diluted with 165 μl 0.5 M NH$_4$Cl, pH 5.5. The $^{111}$In (1.8 mCi) in 10 μL was added to the peptide solution and the mixture was heated in a boiling water bath for 30 min.

The labeled peptide was analyzed by HPLC using a Waters 8×100 mm radial-pak, nova-pak C-18 RCM cartridge column. The column was eluted at 3 mL/min with a linear gradient which started with 100% of 0.1% TFA in water and went to 100% of 0.1% TFA in 90% acetonitrile and 10% water over 10 min. There was about 6% loose $^{111}$In in this labeling which came out at the void volume of the column (1.6 min). There were also some $^{111}$In labeled peaks at 5 min and 6.6 to 8 min. The $^{111}$In labeled peptide was eluted at 8.8 min as a single peak. The HPLC profile of $^{111}$In IMP 237 was nearly identical to $^{111}$In IMP 241.

Serum Stability

An aliquot (30 μL) of $^{111}$In IMP 241 was placed in 300 μL of fresh mouse serum and placed in a 37° C. incubator. The peptide was monitored as described above by HPLC.

An aliquot (24 μL) of $^{111}$In IMP 237 was placed in 230 μL of fresh mouse serum and placed in a 37° C. incubator. The peptide was monitored as described above by HPLC.

The analysis showed that the $^{111}$In IMP 241 may have decomposed slightly (~5%) after heating 22 hr in mouse serum at 37° C. The $^{111}$In IMP 237 was about 70% converted to the shorter retention time peak after incubation for 22 hr at 37° C.

Conclusion

The D-tyrosine in the IMP 241 peptide slows the decomposition of the peptide in mouse serum compared to IMP 237.

In Vivo Stability of IMP 237 and IMP 241 Compared

The in vivo stabilities of $^{111}$In IMP 237 and $^{111}$In IMP 241 were compared by examining (by HPLC) urine samples from mice at 30 and 60 min. The peptides, IMP 241 and IMP 237, were $^{111}$In-111 labeled as described above.

The labeled peptides were injected into Balb/c mice which were sacrificed at 30 min and 60 min post injection of the peptides using one mouse per time point. The attached HPLC traces indicate that $^{111}$In IMP 241 was excreted intact while $^{111}$In IMP 237 was almost completely metabolized to a new $^{111}$In labeled peptide.

Conclusion

The replacement of Tyr with D-Tyr in the peptide backbone minimized metabolism of the peptide in-vivo.

Additional in Vivo Studies

Nude mice bearing GW-39 human colonic xenograft tumors (100-500 mg) were injected with the bi-specific antibody mMu-9×m679 ($1.5 \times 10^{-10}$ mol). The antibody was allowed to clear for 48 hr before the $^{111}$In labeled peptides (8.8 µCi, $1.5 \times 10^{-11}$ mol) were injected. The animals were sacrificed at 3, 24, 48 hr post injection.

The results of the biodistribution studies of the peptides in the mice pretargeted with mMU-9×m679 are shown in Table 3. The tumor to non-tumor ratios of the peptides in the pretargeting study are show in Table 4. The data in Table 5 shows the biodistribution of the peptides in mice that were not pretreated with the bi-specific antibody.

TABLE 3

Pretargeting With $^{111}$In Labeled Peptides 48 hr After Injection of mMU-9 × m679
% Injected/g Tissue

| Tissue | 3 hr After $^{111}$In Peptide | | 24 hr After $^{111}$In Peptide | | 48 hr After $^{111}$In Peptide | |
|---|---|---|---|---|---|---|
| | IMP 237 | IMP 241 | IMP 237 | IMP 241 | IMP 237 | IMP 241 |
| GW-39 | 18.3 ± 7.17 | 26.7 ± 14.1 | 16.7 ± 8.22 | 14.8 ± 4.56 | 12.9 ± 1.10 | 12.3 ± 2.11 |
| Liver | 0.41 ± 0.10 | 0.66 ± 0.34 | 0.32 ± 0.08 | 0.32 ± 0.09 | 0.28 ± 0.09 | 0.32 ± 0.21 |
| Spleen | 0.34 ± 0.12 | 0.63 ± 0.38 | 0.34 ± 0.12 | 0.25 ± 0.07 | 0.28 ± 0.07 | 0.31 ± 0.22 |
| Kidney | 3.62 ± 0.71 | 4.28 ± 0.77 | 2.51 ± 0.54 | 2.34 ± 0.70 | 1.78 ± 0.38 | 1.17 ± 0.43 |
| Lungs | 0.61 ± 0.15 | 1.03 ± 0.65 | 0.22 ± 0.07 | 0.21 ± 0.07 | 0.12 ± 0.04 | 0.14 ± 0.08 |
| Blood | 1.16 ± 0.48 | 1.78 ± 1.49 | 0.21 ± 0.13 | 0.15 ± 0.05 | 0.08 ± 0.03 | 0.10 ± 0.09 |
| Stomach | 0.12 ± 0.04 | 0.21 ± 0.09 | 0.05 ± 0.01 | 0.05 ± 0.02 | 0.04 ± 0.01 | 0.03 ± 0.02 |
| Sm. Int. | 0.23 ± 0.04 | 0.50 ± 0.27 | 0.12 ± 0.02 | 0.09 ± 0.06 | 0.11 ± 0.08 | 0.07 ± 0.06 |
| Lg. Int. | 0.34 ± 0.16 | 0.38 ± 0.15 | 0.15 ± 0.07 | 0.10 ± 0.02 | 0.12 ± 0.07 | 0.09 ± 0.05 |

TABLE 4

Pretargeting With $^{111}$In Labeled Peptides 48 hr After Injection of mMU-9 × m679
Tumor/Non-Tumor Tissue Ratios

| Tissue | 3 hr After $^{111}$In Peptide | | 24 hr After $^{111}$In Peptide | | 48 hr After $^{111}$In Peptide | |
|---|---|---|---|---|---|---|
| | IMP 237 | IMP 241 | IMP 237 | IMP 241 | IMP 237 | IMP 241 |
| Liver | 45.6 ± 17.8 | 41.8 ± 19.6 | 49.8 ± 16.6 | 47.1 ± 8.68 | 49.1 ± 13.6 | 45.1 ± 13.9 |
| Spleen | 56.8 ± 23.8 | 43.5 ± 9.77 | 47.4 ± 14.7 | 59.6 ± 13.0 | 47.5 ± 10.6 | 50.2 ± 19.0 |
| Kidney | 5.13 ± 2.18 | 6.05 ± 2.41 | 6.43 ± 2.24 | 6.58 ± 2.42 | 7.43 ± 1.02 | 11.2 ± 2.61 |
| Lungs | 30.5 ± 10.6 | 28.4 ± 12.8 | 76.4 ± 34.1 | 72.7 ± 21.9 | 115. ± 36.6 | 102. ± 37.1 |
| Blood | 18.6 ± 12.0 | 19.0 ± 11.8 | 86.9 ± 36.2 | 108. ± 41.0 | 187. ± 76.3 | 181. ± 86.6 |
| Stomach | 156. ± 86.1 | 126. ± 49.6 | 303. ± 95.9 | 328. ± 96.7 | 344. ± 101. | 456. ± 193. |
| Sm. Int. | 80.7 ± 29.0 | 59.0 ± 31.0 | 143. ± 60.7 | 193. ± 83.7 | 153. ± 67.7 | 217. ± 73.5 |
| Lg. Int. | 56.3 ± 19.7 | 78.6 ± 54.4 | 116. ± 36.9 | 155. ± 42.4 | 133. ± 47.6 | 153. ± 43.1 |

TABLE 5

Biodistribution of $^{111}$In Labeled Peptides Alone

| Tissue | 30 min After In-111 Peptide | | 3 hr After In-111 Peptide | | 24 hr After In-111 Peptide | |
|---|---|---|---|---|---|---|
| | IMP 237 | IMP 241 | IMP 237 | IMP 241 | IMP 237 | IMP 241 |
| GW-39 | 2.99 ± 1.11 | 2.73 ± 0.37 | 0.17 ± 0.05 | 0.31 ± 0.12 | 0.11 ± 0.02 | 0.11 ± 0.08 |
| Liver | 0.48 ± 0.06 | 0.50 ± 0.09 | 0.15 ± 0.02 | 1.07 ± 1.61 | 0.15 ± 0.01 | 0.09 ± 0.04 |
| Spleen | 0.42 ± 0.08 | 0.43 ± 0.22 | 0.09 ± 0.04 | 0.13 ± 0.05 | 0.13 ± 0.02 | 0.08 ± 0.03 |
| Kidney | 5.85 ± 0.37 | 7.31 ± 0.53 | 3.55 ± 0.44 | 3.21 ± 0.45 | 2.18 ± 0.24 | 2.61 ± 0.51 |
| Lungs | 1.26 ± 0.24 | 1.12 ± 0.26 | 0.13 ± 0.02 | 0.15 ± 0.06 | 0.06 ± 0.00 | 0.07 ± 0.06 |
| Blood | 1.62 ± 0.34 | 1.59 ± 0.29 | 0.12 ± 0.02 | 0.02 ± 0.01 | 0.03 ± 0.01 | 0.00 ± 0.00 |
| Stomach | 0.59 ± 0.32 | 0.52 ± 0.16 | 0.04 ± 0.01 | 0.07 ± 0.03 | 0.03 ± 0.01 | 0.04 ± 0.04 |

TABLE 5-continued

Biodistribution of $^{111}$In Labeled Peptides Alone

| Tissue | 30 min After In-111 Peptide | | 3 hr After In-111 Peptide | | 24 hr After In-111 Peptide | |
|---|---|---|---|---|---|---|
| | IMP 237 | IMP 241 | IMP 237 | IMP 241 | IMP 237 | IMP 241 |
| Sm. Int. | 0.55 ± 0.13 | 2.52 ± 3.73 | 0.09 ± 0.01 | 0.17 ± 0.08 | 0.08 ± 0.01 | 0.04 ± 0.01 |
| Lg. Int. | 0.33 ± 0.05 | 0.30 ± 0.07 | 0.33 ± 0.15 | 0.32 ± 0.14 | 0.05 ± 0.01 | 0.07 ± 0.03 |

Example 4

Synthesis of a Peptide Antigen

The peptide, Ac-Phe-Lys(Ac)-Tyr-Lys(Ac)-OH (SEQ ID NO: 2), is assembled using a resin for solid-phase synthesis and attaching the first residue (lysine) to the resin as the differentially protected derivative alpha-Fmoc-Lys(Aloc)-OH. The alpha-Fmoc protecting group is selectively removed and the Fmoc-Tyr(OBut), alpha-Fmoc-Lys(Aloc)-OH, and Fmoc-Phe-OH added with alternate cycles of coupling and alpha-amino group deprotection. The Aloc- and OBut-side-chain protecting groups are then removed by reaction with TFA and the free alpha- and epsilon-amino groups are capped by reaction with acetic anhydride to give Ac-Phe-Lys(Ac)-Tyr-Lys(Ac)-OH (SEQ ID NO: 2).

Example 5

Coupling of Ac-Phe-Lys(Ac)-Tyr-Lys(Ac)-OH (SEQ ID NO: 2) to KLH

The peptide, Ac-Phe-Lys(Ac)-Tyr-Lys(Ac)-OH (SEQ ID NO: 2), dissolved in water and pH-adjusted to 4.0 with 1N HCl, is treated with a molar equivalent of 1-ethyl-3(3-dimethylaminopropyl)carbodiimide and allowed to react for 1 h at 4° C. Keyhold limpet hemocyanin (KLH) buffered at pH 8.5 is treated with a 100-fold molar excess of the activated peptide and the conjugation reaction is allowed to proceed for 1 h at 4° C. The peptide-KLH conjugate is purified from unreacted peptide by size-exclusion chromatography and used for antibody production.

Example 6

Generation of an Anti-Peptide Ab

Immunocompetent mice are injected with a mixture of the peptide antigen in complete Freund's adjuvant. Two booster shots of the peptide mixed with incomplete Freund's adjuvant are administered over the next several weeks. Spleen cells are harvested from the animals and fused with Sp2/0-Ag14 myeloma cells. Culture supernatants of the resulting clones are analyzed for anti-peptide reactivity by ELISA, using plates coated with the original peptide immunogen. Enzyme-deficient hybridomas are isolated to enable selection of fused cell lines, and selected clones grown in culture media to produce the anti-peptide Abs.

Example 7

Purification of Anti-Peptide Ab

Anti-peptide Ab is purified chromatographically using a protein A column to isolate the IgG fraction, followed by ion-exchange columns to clean the desired product. The Ab of interest is finally purified by using an affinity column comprised of the peptide of interest bound to a solid support, prepared by chemically coupling said peptide to activated beads or resin.

Example 8

Digestion of Anti-Peptide Ab to F(ab')$_2$

The anti-peptide Ab is incubated with 200 μg/μL of pepsin at pH 4 for one hour and purified by a tandem column of protein A, to remove undigested IgG, followed by G-50-Sephadex, to remove low molecular weight contaminants.

Example 9

Reduction of Anti-Peptide-Ab to Fab'-SH

The anti-peptide-F(ab')$_2$ is reduced to a Fab' fragment by reaction with a freshly prepared cysteine solution in 0.1M PBS, containing 10 mM EDTA. The progress of the reaction is followed by HPLC, and when complete, in about 1 h, the Fab'-SH is purified by spin-column chromatography and stored in deoxygenated buffer at pH<5 containing 10 mM EDTA.

Example 10

Oxidative Coupling of Anti-CEA-IgG to a Maleimide Moiety

Anti-CEA Ab IgG is oxidized by reaction with 10 mM sodium periodate for 90 minutes at 4° C., in the dark. The oxidized Ab is purified by spin-column chromatography and mixed with an excess of the cross-linker 4-(4-maleimidophenyl)butyric acid hydrazide (MPBH). The reaction is allowed to proceed for 2 h and the IgG-hydrazone-meleimide purified by spin-column chromatography. The hydrazone bond is reduced by reaction with 10 mM sodium cyanoborohydride and repurified.

Example 11

Preparation of anti-CEA-IgGx anti-Peptide-Fab' Bi-Specific Ab

The IgG-hydrazide-maleimide from Example 10 is treated with an equimolar amount of anti-peptide Fab'-SH, prepared in Example 6, at pH 6.0, for 30 minutes at room temperature. Remaining free thiol groups are blocked by a 30-minute reaction with. iodoacetamide. The bi-specific Ab anti-CEA-IgGxanti-peptide-Fab' is purified by size-exclusion chromatography to remove unreacted Fab', followed by affinity chromatography using solid-phase-bound peptide to separate IgG×Fab' from unreacted IgG.

Example 12

Synthesis of Ac-Phe-Lys(Bz-DTPA)-Tyr-Lys(Bz-DTPA)-NH$_2$ (SEQ ID NO: 2)

The peptide, Ac-Phe-Lys(Bz-DTPA)-Tyr-Lys(Bz-DTPA)-NH$_2$ (SEQ ID NO: 2), is assembled using a resin for solid-phase synthesis and attaching the first residue (lysine to said resin as the differentially protected derivative alpha-Fmoc-Lys(Aloc)-OH. The alpha-Fmoc protecting group is selectively removed and the Fmoc-Tyr(OBut), alpha-Fmoc-Lys(Aloc)-OH, and Fmoc-Phe-OH added with alternate cycles of coupling and alpha-amino group deprotection. The Aloc-side-chain is removed by reaction with palladium (0) catalyst. Alternatively, Boc-group protecting groups may be used which may be removed by reaction with TFA and the free amino groups reacted with excess of the ITC-Bz-DTPA. After removing excess Bz-DTPA, the alpha-amino group is capped by reaction with acetic anhydride, and the entire peptide removed from the resin with TFA (with concomitant deprotection of the tyrosyl residue) to give Ac-Phe-Lys(Bz-DTPA)-Tyr-Lys(Bz-DTPA)-NH$_2$.

Example 13

Radiolabeling of Ac-Phe-Lys(Bz-DTPA)-Tyr-Lys(Bz-DTPA)-NH$_2$ (SEQ ID NO: 2) with Y-90

The title peptide in 100-fold molar excess is mixed with yttrium-90 radionuclide in acetate buffer at pH 5.5. The radiolabeling is complete and quantitative after 30 minutes.

Example 14

Conjugation of a Carboxylesterase to di-DTPA-Peptide

Carboxylesterase (5 mg) in 0.2 M phosphate buffer, pH 8.0, is treated with a five-fold molar excess of the cross-linking agent sulfo-succinimidyl-[4-maleimidomethyl]-cyclohexane-1-carboxylate (sulfo-SMCC). After stirring two hours at room temperature, the activated enzyme is separated from low molecular weight contaminants using a spin-column of G-25 Sephadex and equilibrated in 0.1 M phosphate buffer, pH 7, containing 1 mM EDTA. The tetrapeptide N-acetyl-Cys-Lys(DTPA)-Tyr-Lys(DTPA)-NH$_2$ (SEQ ID NO: 11) (ten-fold molar excess) is added to the activated enzyme and dissolved in the same buffer as used in the spin-column. After stirring for one hour at room temperature, the Cys-Lys(DTPA)-Tyr-Lys(DTPA)-NH$_2$ (SEQ ID NO: 11) peptide carboxylesterase conjugate is purified from unreacted peptide by spin-column chromatography on G-25 Sephadex in 0.25 M acetate buffer, pH 6.0. Successful conjugation is demonstrated by indium-111 labeling of an aliquot of the conjugate, and analysis by size-exclusion HPLC.

Example 15

Use of Anti-CEA-IgG×Anti-Peptide-Fab' Bi-Specific Ab for RAIT

A patient with a CEA-expressing tumor burden is given anti-CEA-IgG×anti-peptide-Fab' bi-specific Ab. Seven days later, the patient is given Y-90-di-Bz-DTPA-peptide (from Example 13). The Y-90-labeled peptide clears rapidly from non-target tissue but localizes avidly to sites pre-targeted with the anti-CEA-IgG×anti-peptide-Fab' bi-specific Ab, effecting destruction of tumors.

Example 16

Preparation of a Galactose-WI2-Fab' Clearing Agent

The anti-idiotypic Ab to MN-14, termed WI2 is digested to a F(ab')$_2$ fragment using pepsin, as outlined in Example 8. The F(ab')$_2$ is reduced to a Fab' fragment using a low molecular weight thiol, as outlined in Example 9. At the end of the reduction, the Fab'-SH is purified by spin-column chromatography and reacted with excess iodoacetamide to block hinge-region thiol groups and prevent reassociation. After repurification from excess iodoacetamide the Fab' is reacted with a 400-fold molar excess of the galactosylation agent, the thio-imidate of cyanomethyl-2,3,4,6-tetra-O-acetyl-1-thio-beta-D-galactopyranoside (see Karacay et al.). The galactosylated protein is purified by two spin-columns and the galactose:Fab' radio determined by MALDI-MS.

Example 17

Use of Anti-CEA-IgG×Anti-Peptide Fab' Bi-Specific Ab for RAIT, with a bsAb Clearing Step A patient with a CEA-expressing tumor burden is given anti-CEA-IgG (MN-14)×anti-peptide-Fab' bi-specific Ab. Three days later, the patient is given a clearing dose of galactose-WI2-Fab'. Twenty-four hours after the clearing dose of a galactose-WI2-Fab', the patient is given Y-90-di-Bz-DTPA-peptide. The Y-90-labeled peptide clears rapidly from non-target tissue but localizes avidly to sites pretargeted with the anti-CEA-IgG×anti-peptide-Fab' bi-specific Ab, effecting destruction of tumors.

Example 18

Synthesis of Ac-Lys(DTPA)-Tyr-Lys(DTPA)-Lys(Tscg-Cys)-NH$_2$ (SEQ ID NO: 7) (IMP 192)

The first amino acid, Aloc-Lys(Fmoc)-OH was attached to 0.2 1 mmol Rink amide resin on the peptide synthesizer followed by the addition of the Tc-99m ligand binding residues Fmoc-Cys(Trt)-OH and TscG to the side chain of the lysine using standard Fmoc automated synthesis protocols to form the following peptide: Aloc-Lys(TscG-Cys(Trt)-rink resin. The Aloc group was then removed by treatment of the resin with 8 mL of a solution containing 100 mg Pd[P(Ph)$_3$]$_4$ dissolved in 10 mL CH$_2$Cl$_2$, 0.75 mL glacial acetic acid and 2.5 ml diisopropylethyl amine. The resin mixture was then treated with 0.8 ml tributyltin hydride and vortex mixed for 60 min. The peptide synthesis was then continued on the synthesizer to make the following peptide: Lys(Aloc)-Tyr-Lys(Aloc)-Lys(Tscg-Cys)-rink resin (SEQ ID NO: 7). The N-terminus was acetylated by vortex mixing the resin for 60 mm with 8 mL of a solution containing 10 mL DMF, 3 mL acetic anhydride, and 6 mL diisopropylethylamine. The side chain Aloc protecting groups were then removed as described above and the resin treated with piperidine using the standard Fmoc deprotection protocol to remove any acetic acid which may have remained on the resin.

Activated DTPA and DTPA Addition

The DTPA, 5 g was dissolved in 40 mL 1.0 M tetrabutylammonium hydroxide in methanol. The methanol was removed under hi-vacuum to obtain a viscous oil. The oil was dissolved in 50 mL DMF and the volatile solvents were removed under hi-vacuum on the rotary evaporator. The DMF treatment was repeated two more times. The viscous oil was then dissolved in 50 ml DMF and mixed with 5 g HBTU. An 8 ml aliquot of the activated DTPA solution was then added to the resin which was vortex mixed for 14 hr. The DTPA treatment was repeated until the resin gave a negative test for amines using the Kaiser test. Alternatively, DTPA Tetra-t-butyl ester could be used with conventional coupling agents such as DIC and HBTU. (See Arano Y, Uezono T, Akizawa H, Ono M, Wakisaka K, Nakayama M, Sakahara H, Konishi J, Yokoyama A., "Reassessment of diethylenetriaminepentaacetic acid (DTPA) as a chelating agent for indium-111 labeling of polypeptides using a newly synthesized monoreactive DTPA derivative," J Med Chem. Aug. 30, 1996;39(18): 3451-60).

Cleavage and Purification

The peptide was then cleaved from the resin by treatment with 8 ml of a solution made from 30 ml TFA, 1 ml triisopropylsilane, and 1 ml ethanedithiol for 60 mm. The crude cleaved peptide was precipitated by pouring into 30 ml ether and was collected by centrifugation. The peptide was then purified by reverse phase HPLC using a 4×30 cm Waters preparative C-18 Delta-Pak column (15 μm, 100 Å). The HPLC fractions were collected and lyophilized to obtain a fraction which contained the desired product by ESMS (MH±1590).

Kit Formulation

The peptide was formulated into lyophilized kits which contained 78 μg of the peptide, 0.92 mg non-radioactive $InCl_3$, 100 μg stannous chloride, 3 mg gentisic acid, and HPCD (10% on reconstitution).

Example 19

Tc-99m Labeling and Stability

An IMP 192 kit was labeled by reconstituting the contents of the vial with 1.5 mL of saline which contained 25 mCi $Na^{99m}TcO_4$. The kit was incubated at room temperature for 10 mm and then heated in a boiling water bath for 15 mm. The labeled peptide solution was then cooled to room temperature. Aliquots were removed for stability studies. The aliquots were diluted 1:10 in saline, 1 mM cysteine in 0.05M phosphate pH 7.5, and fresh human serum. The original kit solution, the saline dilution, and the cysteine challenge were incubated at room temperature while the serum sample was incubated at 37° C. The samples were monitored by HPLC and ITLC. The labeled peptide was stable in the in vitro tests. The retention time of the labeled peptide in serum was shifted from 6.3 mm to 7.3 min. The shift may be due to ion pairing of some serum component with the peptide.

TABLE 6

| Sample | Initial Label | First Time Point | Second Time Point | ITLC 24 hr Saturated NaCl |
|---|---|---|---|---|
| Kit Room Temp. | 1% Void Vol 99% Peptide (6.4 mm) | 3 hr 1% Void Vol 99% Peptide | 21 hr 5% Void Vol 95% Peptide | 5% Solvent Front 94% Origin |
| Saline Dilution Room Temp. | | 1.5 hr 1% Void Vol 99% Peptide | 19 hr 4% Void Vol 96% Peptide | 2.3% Solvent Front 97% Origin |
| Cys Challenge 1 mM in 0.05 M phosphate pH 7.5 Room Temp. | | 1 hr 2% Void Vol 98% Peptide | 19.5 hr 11% Void Vol 89% Peptide | 7.4% Solvent Front 91.3% Origin |
| Human Serum 37° C. | | 2 hr 1% Void Vol 7% 6 min 92% 7.2 min | 20 hr 3% Void Vol 15% 6 min 82% 7.3 min | 1.7% Solvent Front 96% Origin |

Example 20

Preparation of hMN-14×734 (Fab×Fab)

This bsAb was prepared by crosslinking the hMN-14 Fab'$_{SH}$ (a humanized monoclonal anti-CEA antibody) and 734 Fab'$_{mal}$ (a murine anti-diDTPA) fragments, analogously to Example 8. The Fab'$_{SH}$ fragments of hMN-14 and 734 were prepared by reduction of the F(ab')$_2$ fragments with 10 mM 2-mercaptoethylamine in the presence of 10 mM EDTA at pH 7.3 for 60 min at 37° C. Fab'$_{SH}$ was collected after spin column (Penefsky) purification (Sephadex G-50-80, 50 mM NaOAc, 0.5 mM EDTA, pH 5.3) Maleimide group(s) were introduced onto 734 Fab'$_{SH}$ fragment using 4 mM N,N'-o-phenylenedimaleimide at RT for 60 min. Spin column purification was used to isolate the Fab'$_{mal}$. Crosslinking of 734 Fab'$_{mal}$ and hMN-14 Fab'$_{SH}$ was allowed to proceed 16 h at 4° C. at 1:1 molar ratio. To break the disulfide bonds which might have formed during this time, the reaction mixture was treated with 10 mM 2-mercaptoethylamine for 1 h at pH 5.3 at 23° C. The SH groups were blocked with N-ethylmaleimide at pH 6.4. The reaction mixture was applied to a spin column to remove excess small molecular weight compounds. The bsAb was then isolated after purification on an analytical size exclusion HPLC column, Bio-Sil SEC-250. The HPLC retention time of the purified bsAb was 10.23 min.

Example 21

HPLC Binding Studies

The bsAb was radioiodinated using chloramine T (Greenwood and Hunter). Binding of the radioiodinated bsAbs to CEA, WI2 (rat anti-MN-14 idiotypic antibody) and radiolabeled peptidyl DTPA chelate was examined on analytical size exclusion HPLC. Approximately 90% of the radioiodinated bsAb bound to CEA upon treatment with 10-20× molar excess of CEA. The bsAb complexed with radiolabeled indium-DTPA chelates (IMP-156 or IMP-192).

IMP 156 Ac-Phe-Lys(DTPA)-Tyr-Lys(DTPA)-NH$_2$ (SEQ ID NO: 2)

Example 22

Serum Stability

Radioiodinated bsAb was tested for stability in fresh human serum at 37° C. under a humidified 5% $CO_2$ atmosphere. Aliquots were examined on SE-HPLC. In order to detect radioiodine associated with serum proteins, the aliquots were mixed with WI2 to shift-the bsAb peak to earlier retention times. The bsAbs showed 3-5% loss of binding capacity to WI2 after 48 h incubation in serum. Slight aggregate formation (4-7%) was observed upon incubation of the bsAbs in serum for 72 h.

Example 23

99m-Tc-IMP-192

In vitro stability of the Tc-99m complex of this peptidyl chelate was established by incubations in saline, fresh human serum and 10 mM cysteine for up to 20 h. In vivo stability was examined by analysis of urine collected from a mouse injected with 99m-Tc-IMP-192 in a pretargeting experiment. The activity excreted in the urine appears to be the intact peptide because the activity still binds to the antibody as shown by SE-HPLC. Biodistribution studies of 99m-Tc-IMP-192 in normal BALB/c mice showed rapid blood clearance, Table 7. The in vitro and in vivo studies clearly demonstrate stability of 99m-Tc-IMP-192.

TABLE 7

Clearance of 99m-Tc-IMP-192 in BALB/c mice.

| Tissue | % ID/g | | | |
|---|---|---|---|---|
| | 1 h | 2 h | 4 h | 24 h |
| Liver | 0.27 ± 0.18 | 0.22 ± 0.16 | 0.09 ± 0.02 | 0.04 ± 0.0 |
| Spleen | 0.08 ± 0.01 | 0.09 ± 0.3 | 0.05 ± 0.02 | 0.03 ± 0.01 |
| Kidney | 4.16 ± 0.75 | 4.05 ± 0.60 | 3.21 ± 0.99 | 1.21 ± 0.08 |
| Lungs | 0.50 ± 0.23 | 0.29 ± 0.08 | 0.19 ± 0.04 | 0.05 ± 0.00 |
| Blood | 0.30 ± 0.09 | 0.21 ± 0.03 | 0.14 ± 0.04 | 0.05 ± 0.01 |
| Stomach | 0.39 ± 0.18 | 0.42 ± 0.18 | 0.27 ± 0.33 | 0.02 ± 0.01 |
| Small int | 1.37 ± 0.75 | 0.60 ± 0.06 | 0.21 ± 0.09 | 0.03 ± 0.01 |
| Lg.Int. | 0.41 ± 0.54 | 1.53 ± 0.45 | 1.58 ± 0.70 | 0.15 ± 0.14 |
| Muscle | 0.10 ± 0.06 | 0.05 ± 0.00 | 0.03 ± 0.01 | 0.00 ± 0.0 |
| Urine | 169 ± 95 | 57 ± 15 | 6.30 ± 4.53 | 0.20 ± 0.02 |

Example 24

Construction and Expression of hMN-14Fab-734scFv

Recombinant methods were used to produce a monovalent bi-specific fusion protein comprising a Fab fragment derived from a humanized monoclonal anti-CEA antibody and a scFv derived from a murine anti-diDTPA. See FIG. 3. The structure of single chain 734 (734 scFv) was designed as GGGS (SEQ ID NO: 10)-$V_L$-(GGGGS)$_3$ (SEQ ID NO: 9)-$V_H$, in which the proximal GGGS (SEQ ID NO: 10) provides a flexible linkage for the scFv to be connected to the constant region of the heavy chain of hMN-14 (FIG. 1). Alternatively, the scFv can be connected to the constant region of the light chain of hMN-14. Appropriate linker sequences necessary for the in-frame connection of the hMN-14 heavy chain Fd to 734scFv were introduced into the $V_L$ and $V_K$ domains of 734 by PCR reactions using specific primer sets.

PCR-amplification of $734V_L$ was performed using the primer set $734V_L$scFv5'(Cys) and $734V_L$scFv3' (polypeptide and polynucleutide sequences for such primers are shown and described in U.S. patent application Ser. No. 09/337,756, filed on Jun. 22, 1999, the contents of which are incorporated herein by reference in their entirety). The primer $734V_L$scFv5'(Cys) represents the sense-strand sequence encoding the first four residues (PKSC) (SEQ ID NO: 12) of the human IgG1 hinge, linked in-frame to the first six residues (QLVVTQ) of $734V_L$ (SEQ ID NO: 13), via a short flexible linker, GGGS (SEQ ID NO: 10). One cysteine of the human hinge was included because it is required for the interchain disulfide linkage between the hMN-14 heavy chain Fd-734scFv fusion and the hMN-14 light chain. A Pst1 site was incorporated to facilitate ligation at the intronic sequence connecting the $C_H$1 domain and the hinge. The primer 734 $V_L$scFv3' represents the anti-sense sequence encoding the last six residues (TKLKIL) of the $734V_L$ domain (SEQ ID NO: 14) and a portion of the flexible linker sequence (GGGGSGGGG) (SEQ ID NO: 15), which is fused in-frame downstream of the $V_L$ domain.

Following PCR amplification, the amplified product (~400 bp) first was treated with T4 DNA polymerase to remove the extra "A" residue added to the termini during PCR-amplification and subsequently was digested with Pst1. The resultant product was a double-stranded DNA fragment with a Pst1 overhang and a blunt end. PCR amplification of $734V_H$ was performed using the primer set $734V_H$scFv5' and $734V_H$scFV3'(Sac1). Primer $734V_H$scFv5' (see patent Ser. No. 09/337,756) represents the sense-strand sequence encoding the remaining part of the flexible linker sequence (SGGGGS) (SEQ ID NO: 16) connecting the $V_L$ and $V_H$ sequences, and the first six residues (EVKLQE) of the $734 V_H$ domain (SEQ ID NO: 17). Primer $734V_H$scFv3'(Sac1) (see patent Ser. No. 09/337,756) represents the anti-sense sequence encoding the last six residues (TVTVSS) of $734 V_H$ (SEQ ID NO: 18). Also included is a translation stop codon. The restriction sites Eag1 and Sac1 were incorporated downstream of the stop codon to facilitate subcloning. Similarly, the PCR-amplified $V_H$ product of ~400 bp was first treated with T4 DNA polymerase to remove the extra "A" residues at the PCR product termini, and then digested with Sac1, resulting in a $V_H$ DNA fragment with a blunt end-sticky end configuration.

A pBlueScript (Stratagene, La Jolla) based staging vector (HC1kbpSK) containing a SacII fragment of the human IgG1 genomic sequence was constructed. The genomic SacII fragment contains a partial 5' intron, the human IgG1 $C_H$1 domain, the intronic sequence connecting the $C_H$1 to the hinge, the hinge sequence, the intronic sequence connecting the hinge to the $C_H$2 domain, and part of the $C_H^2$ domain. The segment containing the hinge and part of the $C_H^2$ domain in HC1kbpSK was removed by Pst1/Sac1 digestion, and the cloning site generated was used to co-ligate the $V_L$ (Pst1/blunt) and $V_H$ (blunt/Sac1) PCR products prepared above.

The $C_H$1 domain in the resultant construct ($C_H$1-734pSK) is connected to the 734scFv gene sequence via an intron (FIG. 4). Since the genomic SacII fragment for IgG1 only included part of the 5' intron sequence flanking the $C_H$1 domain, the full intronic sequence was restored by inserting the remaining intronic sequence as a BamH1/SacII segment, into the corresponding sites of the $C_H$1-734pSK. The BamH1/Eag1 fragment containing the full 5' intron, $C_H$1 domain, connecting intron, 5 hinge-residues, short GGGS linker (SEQ ID NO: 10), and a 734scFv sequences was then isolated, and used to replace the HindIII/Eag1 segment containing the human genomic IgG1 constant sequence in the hMN-14pdHL2 vector. A HNB linker (see patent Ser. No. 09/337,756) with a BamH1 overhang on one end and a HindIII overhang on the other was used to facilitate the BamH1/Eag1 fragment ligation into the HindIII/Eag1 site in the hMN-14pdHL2 vector. The resultant vector was designated hMN-14-734pdHL2 and can be used to transfect mammalian cells for the expression of the bi-specific protein.

The hMN-14pdHL2 vector was derived from the vector, pdHL2, which has previously been described. See Losman et al., *Cancer Supplement*, 80:2660, 1997. Construction of hMN-14pdHL2 was performed by replacing the $V_H$ and $V_K$ domains of hLL2pdHL2 with that of hMN-14 using standard molecular biology techniques (FIG. 5). The hMN-14-734pdHL2 vector was transfected into SP2/0 cells by electroporation and the cell clones secreting bsAb were identified. The bsAb purified from cell culture supernatant (clone 341.1G6) on a protein L column (Pierce, Rockford, Ill.) is a 75 kD protein (based on amino acid sequence calculation) that co-migrated with the 66 kD marker in non-reducing SDS-PAGE probably due to secondary structure (FIG. 2, lane 2). Under reducing conditions, bands corresponding to a heavy (50 kD) and a light (25 kD) chain were observed (FIG. 2, lane 4). Kappa chain monomers (25 kD) and dimers (50 kD) secreted by the transfectoma also were co-purified (FIG. 2, lane 2) since protein L binds to kappa light chains of human, mouse and rat. Further separation of bsAb from kappa mono- and dimers is accomplished with ion-exchange chromatography. Purified hMN-14Fab-734scFv shows specific binding to both CEA and In-DTPA-BSA in a dose dependent manner.

Example 25

Transgenic Production of bscAb in Milk

A bscAb fragment is cloned into an expression vector containing a 5' casein promoter sequence and 3' untranslated genomic sequences that flank the insertion site. The expression cassette is then injected into the pronuclei of fertilized, mouse eggs, using procedures standard in the art. The eggs are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk by complementary binding to an immobilized antigen, column chromatography or other methods known in the art.

Example 26

Transgenic Production of bscAb in Plants

A bscAb fragment is cloned into an expression vector containing a shortened legumin B4 promoter plus 54 base pairs of LeB4 untranslated RNA leader from *Vicia faba* and encoding a LeB4 signal peptide, to direct the protein to the endoplasmic recticulum. The expression cassette is transformed into tobacco leaf discs according to the methods described by Zambryski et al., using *Agrobacterium*-mediated gene transfer. Transformation is verified by Southern analysis. Transgenic plants are analyzed for the presence and functionality of the bscAb using standard immunological methods known in the art. The bscAb can be purified from the plant tissues using standard methods known in the art.

Example 27

Pretargeting Experiments

Female nude mice (Taconic NCRNU, 3-4 weeks old) with GW 39 tumor xenografts were used for the pretargeting experiments. Tumors were 0.3-0.8 g.

TABLE 8

Biodistribution of 125-I-hMN-14 × 734 bsAb and 111-In-indium-IMP-156 peptide in nude mice bearing GW-39 tumor xenografts: hMN-14 × 734 was allowed 48 h for localization prior to 111-In-indium-IMP-156 injection. Biodistribution was performed 3 h post 111-In-indium-IMP-156. bsAb:peptide ratio administered, 1:0.03. Five animals per time point.

| Tissue | 125-I-hMN-14 × 734 | | 111-In-indium-IMP-156 | |
| --- | --- | --- | --- | --- |
| | % ID/g | T/NT | % ID/g | T/NT |
| tumor | 2.9 ± 1.1 | 1 | 5.2 ± 1.9 | 1 |
| Liver | 0.1 ± 0.06 | 19 ± 6 | 0.5 ± 0.09 | 10.6 ± 3.5 |
| Spleen | 0.5 ± 0.03 | 6.3 ± 1.2 | 0.5 ± 0.1 | 12 ± 6 |
| Kidney | 0.3 ± 0.08 | 9.3 ± 1.8 | 1.9 ± 0.5 | 2.6 ± 0.5 |
| Lungs | 0.3 ± 0.1 | 12 ± 3 | 0.4 ± 0.1 | 12 ± 2 |
| Blood | 0.3 ± 0.1 | 11 ± 2 | 0.7 ± 0.2 | 7.6 ± 1.5 |

TABLE 9

Control group showing the clearance of 111-In-indium-IMP-156 at 3 h after injection.

| | % ID/g | T/NT |
| --- | --- | --- |
| Tumor | 0.14 ± 0.02 | 1 |
| Liver | 0.42 ± 0.1 | 0.3 ± 0.1 |
| Spleen | 0.28 ± 0.09 | 0.5 ± 0.1 |
| Kidney | 0.93 ± 0.13 | 0.2 ± 0.03 |
| Lungs | 0.04 ± 0.01 | 3.5 ± 0.7 |
| Blood | 0.05 ± 0.01 | 3.1 ± 0.7 |

TABLE 10

Nude mice bearing GW 39 tumor xenografts were administered 125-I-labeled bsAb (5 µCi, 15 µg, 1.5 × 10$^{-10}$ mol). hMN-14 × 734 was allowed 24 h for localization and clearance before administering 99m-Tc-IMP-192 (10 µCi, 1.6 × 10$^{-11}$ mol of peptide). Biodistribution studies were performed at 30 min, 1, 3 and 24 h post 99m-Tc-IMP-192 injection, five animals per time point. BsAb:peptide, 1:0.1.

| | % ID/g | | | |
| --- | --- | --- | --- | --- |
| Tissue | 30 min | 1 h | 3 h | 24 h |
| | 125-I-hMN-14 × 734 | | | |
| Tumor | 4.9 ± 1.1 | 6.0 ± 2.3 | 5.5 ± 1.1 | 3.3 ± 0.7 |
| Liver | 0.6 ± 0.1 | 0.5 ± 0.2 | 0.5 ± 0.1 | 0.1 ± 0.02 |
| Spleen | 0.8 ± 0.3 | 0.7 ± 0.3 | 0.7 ± 0.2 | 0.2 ± 0.03 |
| Kidney | 0.5 ± 0.1 | 0.5 ± 0.1 | 0.5 ± 0.1 | 0.1 ± 0.02 |
| Lungs | 0.9 ± 0.3 | 0.8 ± 0.2 | 0.8 ± 0.3 | 0.3 ± 0.1 |
| Blood | 0.9 ± 0.3 | 1.2 ± 0.4 | 1.1 ± 0.3 | 0.2 ± 0.07 |
| | 99m-Tc-IMP-192 | | | |
| Tumor | 11.4 ± 4.8 | 14.3 ± 3.6 | 12.6 ± 5.2 | 8.7 ± 3.3 |
| Liver | 1.4 ± 0.3 | 0.9 ± 0.2 | 0.6 ± 0.1 | 0.4 ± 0.08 |
| Spleen | 1.2 ± 0.4 | 0.8 ± 0.2 | 0.5 ± 0.1 | 0.4 ± 0.2 |
| Kidney | 9.9 ± 6.1 | 4.6 ± 0.7 | 2.4 ± 0.5 | 1.2 ± 0.3 |
| Lungs | 4.2 ± 3.4 | 3.6 ± 1.9 | 1.0 ± 0.3 | 0.3 ± 0.1 |
| Blood | 4.3 ± 1.2 | 3.5 ± 0.9 | 1.7 ± 0.4 | 0.6 ± 0.2 |

TABLE 11

Nude mice bearing GW 39 tumor xenografts were administered 125-I-labeled bsAb (5 µCi, 15 µg, $1.5 \times 10^{-10}$ mol). hMN-14 × 734 was allowed 24 h for localization and clearance before administering 99m-Tc-IMP-192 (10 µCi, $1.6 \times 10^{-11}$ mol of peptide). Biodistribution studies were performed at 30 min, 1, 3 and 24 h post 99m-Tc-IMP-192 injection, five animals per time point. BsAb:peptide, 1:0.1.

| | Tumor/non-tumor ratio | | | |
|---|---|---|---|---|
| Tissue | 30 min | 1 h | 3 h | 24 h |
| | 125-I-hMN-14 x | | | |
| Liver | 8.8 ± 1.5 | 12.1 ± 5.5 | 10.3 ± 2.5 | 23.8 ± 3.5 |
| Spleen | 6.4 ± 1.6 | 9.3 ± 4.0 | 7.9 ± 1.7 | 18.2 ± 4.0 |
| Kidney | 10.0 ± 2.6 | 12.5 ± 4.5 | 11.1 ± 3.0 | 27.3 ± 4.6 |
| Lungs | 6.2 ± 2.3 | 8.4 ± 4.6 | 7.2 ± 2.3 | 12.4 ± 6.6 |
| Blood | 5.7 ± 2.1 | 4.9 ± 1.2 | 5.1 ± 1.3 | 14.5 ± 3.6 |
| | 99m-Tc-IMP-192 | | | |
| Liver | 7.9 ± 1.7 | 15.7 ± 5.4 | 20.7 ± 7.6 | 22.3 ± 7.4 |
| Spleen | 9.4 ± 1.0 | 19.5 ± 8.6 | 22.9 ± 7.5 | 23.8 ± 3.5 |
| Kidney | 1.2 ± 0.2 | 3.1 ± 0.6 | 5.2 ± 1.5 | 7.3 ± 1.9 |
| Lungs | 3.7 ± 1.7 | 5.5 ± 3.6 | 13.5 ± 7.1 | 30.8 ± 14.4 |
| Blood | 2.7 ± 0.7 | 4.2 ± 1.3 | 7.3 ± 2.3 | 16.1 ± 6.4 |

TABLE 12

Control group of nude mice bearing GW-39 tumors received 99m-Tc-IMP-192 (10 µCi, $1.6 \times 10^{-11}$ mol of peptide) and were sacrificed 3 h later.

| | 99m-Tc-IMP-192 |
|---|---|
| Tissue | % ID/g |
| Tumor | 0.2 ± 0.05 |
| Liver | 0.3 ± 0.07 |
| Spleen | 0.1 ± 0.05 |
| Kidney | 2.6 ± 0.9 |
| Lungs | 0.2 ± 0.07 |
| Blood | 0.2 ± 0.09 |

The percentage of the available DTPA binding sites on the tumor bound bsAb filled with 99m-Tc-IMP-192 was calculated from the above data assuming one peptide bound to one bsAb molecule. However, it is possible that one peptide molecule can crosslink two molecules of bsAb.

TABLE 13

Percentage of the available DTPA binding sites on the tumor bound bsAb filled with 99m-Tc-IMP-192

| time | % saturation on hMN-14 × 734 |
|---|---|
| 30 min | 25.4 |
| 1 h | 25.8 |
| 3 h | 25 |
| 24 h | 28 |

The foregoing experimental data show that: the humanized x murine bsAb retained its binding capability to CEA and indium-DTPA; the hMN-14×734 (Fab×Fab) effectively targets a tumor; the dual functional peptidyl Tc-99m chelator was stable; 99m-Tc-IMP-192 complexed to tumor-localized hMN-14×734 and was retained for at least 24 h; and imaging of tumors is possible at early time points (1-3 h) post 99m-Tc-IMP-192 injection.

Example 28

Use of Anti-CEA Fab×Anti-Peptide scFv Fusion Protein for RAIT, with a bsAb Clearing Step A 69-year-old man with colon cancer that had undergone resection for cure, after a year is found to have a CEA blood serum level of 50 ng/mL. The patient undergoes a CT scan, and 5 tumor lesions ranging from 1 cm to 3 cm are present in the left lobe of the liver. The patient is given 100 mg of hMN14-Fab/734-scFv fusion protein. Three days later, the patient is given a clearing dose of galactose-WI2-Fab'. Twenty-four hours after the clearing dose of agalactose-WI2-Fab', the fusion protein in the blood is reduced 20-fold the concentration of the protein just prior to injection of the clearing agent. The patient is then infused with the IMP 245 Y-90-di-Bz-DTPA-peptide, containing 50 mCi of Y-90. A CT scan performed three months later demonstrates three of the lesions have disappeared, and the remaining two have not increased in size. The CEA blood serum level is decreased to 10 ng/mL at this time. No increase is seen in the CEA blood serum level for the following 6 months, and CT scans demonstrate no growth of the two tumor lesions. The therapy is repeated a year after the first therapy, when an increase in CEA is observed, and the two tumor lesions are observed to decrease in size at 3 months and six months after the second therapy. The blood serum CEA level after six months is less than 5 ng/mL.

Example 29

Preparation of a Carboxylesterase-DTPA Conjugate

Two vials of rabbit liver carboxylesterase (SIGMA; protein content ~17 mg) are reconstituted in 2.2 ml of 0.1 M sodium phosphate buffer, pH 7.7 and mixed with a 25-fold molar excess of CA-DTPA using a freshly prepared stock solution (~25 mg/ml) of the latter in DMSO. The final concentration of DMSO in the conjugation mixture is 3% (v/v). After 1 hour of incubation, the mixture is pre-purified on two 5-mL spin-columns (Sephadex G50/80 in 0.1 M sodium phosphate pH 7.3) to remove excess reagent and DMSO. The eluate is purified on a TSK 3000G Supelco column using 0.2 M sodium phosphate pH 6.8 at 4 ml/min. The fraction containing conjugate is concentrated on a Centricon-10™ concentrator, and buffer-exchanged with 0.1 M sodium acetate pH 6.5. Recovery: 0.9 ml, 4.11 mg/ml (3.7 mg). Analytical HPLC analysis using standard conditions, with in-line UV detection, revealed a major peak with a retention time of 9.3 min and a minor peak at 10.8 min in 95-to-5 ratio. Enzymatic analysis showed 115 enzyme units/mg protein, comparable to unmodified carboxylesterase. Mass spectral analyses (MALDI mode) of both unmodified and DTPA-modified CE shows an average DTPA substitution ratio near 1.5. A metal-binding assay using a known excess of indium spiked with radioactive indium confirmed the DTPA:enzyme ratio to be 1.24 and 1.41 in duplicate experiments. Carboxylesterase-DTPA is labeled with In-111 acetate at a specific activity of 12.0 mCi/mg, then treated with excess of non-radioactive indium acetate, and finally treated with 10 mM EDTA to scavenge off excess non-radioactive indium. Incorporation by HPLC and ITLC analyses is 97.7%. A HPLC sample is completely complexed with a 20-fold molar excess of bispecific antibody hMN-14 Fab'×734 Fab', and the resultant product further complexes with WI2 (anti-ID to hMN-14), with the latter in 80-fold molar excess with respect to bi-specific antibody.

Example 30

Synthesis of IMP 224

An amount of 0.0596 g of the phenyl hydrazine containing peptide IMP 221 ($H_2N$—NH—$C_6H_4$-CO-Lys(DTPA)-Tyr-Lys(DTPA)-$NH_2$ $MH^+$ 1322, made by Fmoc SPPS) was mixed with 0.0245 g of Doxorubicin hydrochloride in 3 mL of DMF. The reaction solution was allowed to react at room temperature in the dark. After 4 hours an additional 0.0263 g of IMP 221 was added and the reaction continued overnight. The entire reaction mixture was then purified by HPLC on a Waters Nova-Pak (3-40×100 mm segments, 6 μm, 60 Å) prep column eluting with a gradient of 80:20 to 60:40 Buffer A:B over 40 min (Buffer A=0.3% $NH_4OAc$, Buffer B=0.3% $NH_4OAc$ in 90% $CH_3CN$). The fractions containing product were combined and lyophilized to afford 0.0453 g of the desired product, which was confirmed by ESMS $MH^+$ 1847.

Example 31

IMP 224 Kit Formulation

The peptide of Example 31 was formulated into kits for In-111 labeling. A solution was prepared which contained 5.014 g 2-hydroxypropyl-β-cyclodextrin, and 0.598 g citric acid in 85 mL. The solution was adjusted to pH 4.20 by the addition of 1 M NaOH and diluted with water to 100 mL. An amount of 0.0010 g of the peptide IMP 224 was dissolved in 100 mL of the buffer, and 1 mL aliquots were sterile filtered through a 0.22 μm Millex GV filter into 2 mL lyophilization vials which were immediately frozen and lyophilized.

Example 32

In-111 Labeling of IMP 224 Kits

The In-111 was dissolved in 0.5 mL water and injected into the lyophilized kit. The kit solution was incubated at room temperature for 10 min then 0.5 mL of a pH 7.2 buffer which contained 0.5 M NaOAc and $2.56 \times 10^{-5}$ M cold indium was added.

Example 33

In-Vitro Stability of IMP 224 Kits

An IMP 224 kit was labeled as described with 2.52 mCi of In-111. Aliquots (0.15 mL, 370 μCi) were withdrawn and mixed with 0.9 mL 0.5 M citrate buffer pH 4.0, 0.9 mL 0.5 M citrate buffer pH 5.0, and 0.9 mL 0.5 M phosphate buffer pH 7.5. The stability of the labeled peptide was followed by reverse phase HPLC. HPLC Conditions: Waters Radial-Pak C-18 Nova-Pak 8×100 mm, Flow Rate 3 mL/min, Gradient: 100 % A=0.3% $NH_4OAc$ to 100% B=90% $CH_3CN$, 0.3% $NH_4OAc$ over 10 min.

TABLE 14

In-Vitro Stability of In/In-111 IMP 224

| Kit | | pH 4.0 | | pH 5.0 | | pH 7.5 | |
|---|---|---|---|---|---|---|---|
| Time | Intact Peptide | Time | Intact Peptide | Time | Intact Peptide | Time | Intact Peptide |
| 0 0 | 00 | 4 min | 00 | 0 min | 00 | .5 hr | 00 |
| | | hr | 00* | hr | 00* | .5 hr | 4 |
| 1 hr | 9 | 9 hr | 5 | 0 hr | 1 | 0 hr | 0 |

Some peptide decomposed but was not included in the calculation of the areas of the peaks Example 34

In-Vivo Biodistribution of IMP 221 in BALB/c Mice

Kits were reconstituted with 400 μCi In-111 in 0.5 mL water. The In-111 kit solution was incubated at room temperature for 10 min and then diluted with 1.5 mL of the cold indium containing pH 7.2, 0.5 M acetate buffer. The labeled peptide was analyzed by ITLC in saturated NaCl. The loose In-111 was at the top 20% of the ITLC strip.

Each mouse was injected with 100 μL (20 μCi) of the In-111 labeled peptide. The animals were anesthetized and sacrificed at 30 minutes, 1 hours, 2 hours, 4 hours, and 24 hours using three mice per time point. Blood, muscle, liver, lungs, kidneys, spleen, large intestine, small intestine, stomach, urine, and tail were collected and counted. The results of the biodistribution study are shown in the following table.

TABLE 15

Biodistribution in BALB/c mice % ID/g of IMP 224
(Dox = N—NH—$C_6H_4$—CO-Lys(DTPA)-Tyr-Lys(DTPA)-$NH_2$ $MH^+$ 1847 radiolabeled with In-111 and saturated with cold In

| Tissue | 30 min | 1 hr | 2 hr | 4 hr | 24 hr |
|---|---|---|---|---|---|
| Liver | 0.57 ± 0.04 | 0.31 ± 0.03 | 0.17 ± 0.03 | 0.17 ± 0.01 | 0.13 ± 0.02 |
| Spleen | 0.57 ± 0.18 | 0.27 ± 0.06 | 0.12 ± 0.01 | 0.11 ± 0.01 | 0.07 ± 0.00 |
| Kidney | 8.45 ± 1.79 | 5.36 ± 1.01 | 3.75 ± 0.52 | 4.03 ± 0.45 | 2.12 ± 0.17 |
| Lungs | 1.61 ± 0.34 | 0.99 ± 0.26 | 0.25 ± 0.02 | 0.17 ± 0.02 | 0.09 ± 0.02 |
| Blood | 1.44 ± 0.28 | 0.54 ± 0.12 | 0.12 ± 0.01 | 0.10 ± 0.01 | 0.02 ± 0.00 |
| Stomach | 0.61 ± 0.07 | 0.15 ± 0.07 | 0.05 ± 0.01 | 0.06 ± 0.02 | 0.04 ± 0.02 |
| Small Int. | 0.72 ± 0.08 | 0.37 ± 0.19 | 0.09 ± 0.01 | 0.09 ± 0.03 | 0.05 ± 0.01 |
| Large Int. | 0.59 ± 0.43 | 0.18 ± 0.04 | 0.38 ± 0.15 | 0.30 ± 0.06 | 0.08 ± 0.03 |
| Muscle | 0.51 ± 0.19 | 0.21 ± 0.08 | 0.03 ± 0.02 | 0.02 ± 0.00 | 0.01 ± 0.00 |

TABLE 15-continued

Biodistribution in BALB/c mice % ID/g of IMP 224
(Dox = N—NH—$C_6H_4$—CO-Lys(DTPA)-
Tyr-Lys(DTPA)-$NH_2$ $MH^+$ 1847 radiolabeled
with In-111 and saturated with cold In

| Tissue | 30 min | 1 hr | 2 hr | 4 hr | 24 hr |
|---|---|---|---|---|---|
| Urine | 1553 | 1400 ± 421 | 19.1 | 1.72 ± 0.67 | 0.42 ± 0.18 |
| Tail | 3.66 ± 0.43 | 1.90 ± 0.09 | 0.46 ± 0.09 | 0.24 ± 0.03 | 0.58 ± 0.22 |

Example 35

In-Vivo Stability and Clearance of IMP 224

Kits were reconstituted with 4 mCi In-111 in 0.5 mL water. The In-111 kit was incubated at room temperature for 10 min and then diluted with 0.5 mL of the cold indium containing 0.5 M pH 7.2 acetate buffer. The labeled peptide was analyzed by ITLC in saturated NaCl. The loose In-111 was at the top 20% of the ITLC strip.

Each mouse was injected with 100 μL (400 μCi) of the In-111 labeled peptide. The animals were anesthetized and sacrificed at 30 min and 1 hr using two animals per time point. The serum and urine samples were collected, stored on ice, and sent on ice as soon as possible for HPLC analysis. The HPLC (by size exclusion chromatography) of the urine samples showed that the In-111 labeled peptide could still bind to the antibody. The reverse phase HPLC analysis showed that the radiolabeled peptide was excreted intact in the urine. The amount of activity remaining in the serum was too low to be analyzed by reverse phase HPLC due to the poor sensitivity of the detector. Doxorubicin has ~95% hepatobiliary clearance. Thus, by attaching the bis DTPA peptide in a hydrolyzeable manner, the biodistribution of the drug is altered to give ~100% renal excretion. This renders the drug far less toxic because all of the nontargeted drug is rapidly excreted intact.

TABLE 16

Activity Recovered in The Urine and Serum

| | 30 min | | 1 hr | |
|---|---|---|---|---|
| Tissue | Animal #1 | Animal #2 | Animal #1 | Animal #2 |
| Urine | 220 μCi | 133 μCi | 41.1 μCi | 273 μCi |
| Serum | 1.92 μCi | 3.64 μCi | 1.21 μCi | 1.27 μCi |

Example 36

Pretargeting Experiments with IMP 224 and IMP 225

A lyophilized kit of IMP 224 containing 10 micrograms of peptide was used. The kit was lyophilized in 2 mL vials and reconstituted with 1 mL sterile water. A 0.5 mL aliquot was removed and mixed with 1.0 mCi In-111. The In-111 kit solution was incubated at room temperature for 10 minutes then 0.1 mL was removed and diluted with 1.9 mL of the cold indium containing acetate buffer BM 8-12 in a sterile vial. The labeled peptide was analyzed by ITLC in saturated NaCl. The loose In-111 was at the top 20% of the ITLC strip.

Female nude mice (Taconic NCRNU, 3-4 weeks old) with GW 39 tumor xenografts were used for the pretargeting experiments. Tumors were 0.3-0.8 g. Each animal was injected with 100 microliters (5 μCi, 15 μg, $1.5 \times 10^{-10}$ mol) of the I-125 labeled antibody F6×734-F(ab')$_2$.

Seventy two hours later, each mouse was injected with 100 μL (10 μCi) of the In-111 labeled peptide. The animals were anesthetized and sacrificed at 1 hour, 4 hours and 24 hours using five mice per time point. Tumor, blood, muscle, liver, lungs, kidneys, spleen, large intestine, small intestine, stomach, urine and tail were collected and counted.

The experiment was repeated with a lyophilized kit of IMP 225 Ac-Cys(Dox-COCH$_2$)-Lys(DTPA)-Tyr-Lys(DTPA)-NH$_2$ (SEQ ID NO: 11) $MNa^+$ 1938), containing 11 micrograms of peptide.

TABLE 17

Biodistribution of In-111-IMP-224 in nude mice bearing GW-39 tumor xenografts, previously given F6 × 734-F(ab')$_2$ 72 h earlier. Data in % ID/g tissue. n = 5.

| | 1 h | | 4 h | | 24 h | |
|---|---|---|---|---|---|---|
| Tissue | I-125 | In-111 | I-125 | In-111 | I-125 | In-111 |
| GW-39 | 10.0 ± 1.5 | 10.3 ± 1.7 | 9.8 ± 2.6 | 11.0 ± 2.0 | 8.8 ± 1.2 | 9.7 ± 1.1 |
| Liver | 0.1 ± 0.0 | 0.4 ± 0.1 | 0.1 ± 0.0 | 0.3 ± 0.0 | 0.1 ± 0.0 | 0.3 ± 0.0 |
| Spleen | 0.1 ± 0.0 | 0.4 ± 0.1 | 0.1 ± 0.0 | 0.2 ± 0.0 | 0.1 ± 0.0 | 0.2 ± 0.0 |
| Kidney | 0.3 ± 0.1 | 3.5 ± 0.6 | 0.2 ± 0.0 | 2.8 ± 0.3 | 0.2 ± 0.0 | 1.9 ± 0.2 |
| Lungs | 0.2 ± 0.0 | 0.8 ± 0.2 | 0.2 ± 0.0 | 0.4 ± 0.0 | 0.2 ± 0.0 | 0.1 ± 0.0 |
| Blood | 0.4 ± 0.1 | 1.8 ± 0.6 | 0.4 ± 0.1 | 0.9 ± 0.2 | 0.4 ± 0.0 | 0.2 ± 0.0 |
| Stomach | 0.5 ± 0.2 | 0.8 ± 1.3 | 0.5 ± 0.2 | 0.1 ± 0.0 | 0.7 ± 0.2 | 0.1 ± 0.0 |

TABLE 17-continued

Biodistribution of In-111-IMP-224 in nude mice bearing GW-39 tumor xenografts, previously given F6 × 734-F(ab')₂ 72 h earlier. Data in % ID/g tissue. n = 5.

| Tissue | 1 h | | 4 h | | 24 h | |
|---|---|---|---|---|---|---|
| | I-125 | In-111 | I-125 | In-111 | I-125 | In-111 |
| Small Int. | 0.1 ± 0.0 | 0.5 ± 0.4 | 0.1 ± 0.0 | 0.2 ± 0.0 | 0.1 ± 0.0 | 0.1 ± 0.0 |
| Large Int. | 0.1 ± 0.0 | 0.1 ± 0.0 | 0.1 ± 0.0 | 0.3 ± 0.1 | 0.1 ± 0.1 | 0.1 ± 0.1 |
| Muscle | 0.0 ± 0.0 | 0.3 ± 0.2 | 0.0 ± 0.0 | 0.0 ± 0.0 | 0.0 ± 0.0 | 0.0 ± 0.0 |
| Urine | 1.1 ± 2.0 | 168 ± 106 | 1.8 ± 0.6 | 31.8 ± 31 | 0.9 ± 0.2 | 1.2 ± 0.2 |
| Tail | 0.1 ± 0.0 | 1.1 ± 0.2 | 0.1 ± 0.0 | 0.4 ± 0.1 | 0.2 ± 0.0 | 0.2 ± 0.0 |

TABLE 18

Biodistribution of In-111-IMP-224 in nude mice bearing GW-39 tumor xenografts, previously given F6 × 734-F(ab')₂ 72 h earlier. Data in tumor-to-normal organ ratios. n = 5.

| Tissue | 1 h | | 4 h | | 24 h | |
|---|---|---|---|---|---|---|
| | I-125 | In-111 | I-125 | In-111 | I-125 | In-111 |
| GW-39 | 1 | 1 | 1 | 1 | 1 | 1 |
| Liver | 85.4 ± 25 | 24.0 ± 5.9 | 81.8 ± 25 | 35.4 ± 6.9 | 61.1 ± 8.5 | 31.6 ± 5.8 |
| Spleen | 81.0 ± 34 | 28.7 ± 8.7 | 74.5 ± 25 | 44.7 ± 10 | 60.8 ± 8.6 | 47.0 ± 2.2 |
| Kidney | 39.7 ± 9.4 | 3.0 ± 0.5 | 57.1 ± 14 | 3.9 ± 0.5 | 39.6 ± 4.8 | 5.0 ± 0.5 |
| Lungs | 51.2 ± 10 | 13.4 ± 2.7 | 50.7 ± 10 | 30.1 ± 4.9 | 50.3 ± 10 | 69.0 ± 9.4 |
| Blood | 25.2 ± 8.3 | 6.1 ± 2.5 | 22.9 ± 7 | 12.8 ± 2.0 | 21.8 ± 4.2 | 41.8 ± 6.3 |
| Stomach | 21.0 ± 6.7 | 48.7 ± 37 | 22.1 ± 7 | 128 ± 46 | 14.9 ± 6.0 | 147 ± 39 |
| Small Int. | 137 ± 41 | 31.9 ± 18 | 128 ± 37 | 51.6 ± 14 | 102 ± 3.7 | 110 ± 13 |
| Large Int. | 136 ± 32 | 87.1 ± 35 | 130 ± 39 | 45.6 ± 19 | 113 ± 12 | 92.4 ± 38 |
| Muscle | 209 ± 86 | 38.6 ± 13 | 1396± | 727 ± 797 | 233 ± 42 | 283 ± 46 |
| Urine | 11.0 ± 23 | 0.3 ± 0.5 | 6.3 ± 4.2 | 0.71 ± 0.6 | 9.8 ± 1.9 | 8.3 ± 1.3 |
| Tail | 72.7 ± 20 | 9.4 ± 2.8 | 73.6 ± 20 | 26.4 ± 5.2 | 53.9 ± 10 | 55.9 ± 5.7 |

TABLE 19

Biodistribution of In-111-IMP-225 in nude mice bearing GW-39 tumor xenografts, previously given F6 × 734-F(ab')₂ 72 h earlier. Data in % ID/g tissue. n = 5.

| Tissue | 1 h | | 4 h | | 24 h | |
|---|---|---|---|---|---|---|
| | I-125 | In-111 | I-125 | In-111 | I-125 | In-111 |
| GW-39 | 6.2 ± 5.9 | 14.6 ± 14 | 10.5 ± 3.8 | 16.5 ± 4.8 | 8.3 ± 3.0 | 10.1 ± 2.3 |
| Liver | 0.1 ± 0.1 | 0.4 ± 0.2 | 0.2 ± 0.0 | 0.4 ± 0.1 | 0.1 ± 0.0 | 0.3 ± 0.1 |
| Spleen | 0.5 ± 0.7 | 1.6 ± 2.4 | 0.2 ± 0.1 | 0.4 ± 0.1 | 0.1 ± 0.0 | 0.4 ± 0.1 |
| Kidney | 0.3 ± 0.1 | 3.8 ± 0.9 | 0.3 ± 0.1 | 3.8 ± 0.4 | 0.2 ± 0.1 | 1.7 ± 0.3 |
| Lungs | 0.3 ± 0.1 | 0.8 ± 0.4 | 0.3 ± 0.0 | 0.6 ± 0.1 | 0.2 ± 0.1 | 0.2 ± 0.1 |
| Blood | 0.5 ± 0.1 | 2.0 ± 0.4 | 0.8 ± 0.4 | 1.3 ± 0.2 | 0.3 ± 0.1 | 0.4 ± 0.2 |
| Stomach | 0.1 ± 0.2 | 1.1 ± 0.9 | 0.8 ± 0.4 | 0.4 ± 0.2 | 0.3 ± 0.0 | 0.1 ± 0.0 |
| Small Int. | 0.1 ± 0.0 | 0.4 ± 0.1 | 0.1 ± 0.0 | 0.3 ± 0.2 | 0.1 ± 0.0 | 0.1 ± 0.0 |
| Large Int. | 0.1 ± 0.0 | 0.2 ± 0.0 | 0.1 ± 0.0 | 0.3 ± 0.1 | 0.1 ± 0.0 | 0.1 ± 0.0 |
| Muscle | 0.0 ± 0.0 | 0.3 ± 0.2 | 0.1 ± 0.0 | 0.2 ± 0.0 | 0.0 ± 0.0 | 0.1 ± 0.0 |
| Urine | 2.8 ± 3.4 | 110 ± 40 | 2.0 ± 1.0 | 13.5 ± 6.4 | 0.3 ± 0.3 | 0.7 ± 0.4 |
| Tail | 0.4 ± 0.2 | 1.2 ± 0.1 | 0.2 ± 0.0 | 0.8 ± 0.2 | 0.1 ± 0.1 | 0.5 ± 0.7 |

Combinations of the bi-specific constructs described in the present invention or others of similar specificities are suitable for pretargeted RAIT, where IMP-192 peptide and its analogues are labeled with therapeutic radioisotopes such as 188-Re, 213-Bi, 67-Cu and the like. It will be recognized that therapeutic chelates can be conjugated to peptides that have other than chelate epitopes for recognition by bsAbs, as described above.

It will be appreciated as well that detectable radiolabels can be directed to a site of interest, e.g. a tumor, which is to be excised or otherwise detected and/or treated in intra-operative, endoscopic, intravascular or other similar procedures, using the pretargeting methods of the present invention, in combination with various linkers. The pretargeting is effected with non-radioactive bsAbs and the eventual administration and localization of the low molecular weight radiolabeled linker, and clearance of unbound linker, are both comparatively rapid, compatible with surgical procedures that should avoid needless delay and which can use radioisotopes with short half-lives. Additionally, the disclosed therapies can be used for post-surgical radioimmunotherapy protocols to ensure the eradication of residual tumor cells.

Example 37

Synthesis of DOTA-Phe-Lys(HSG)-D-Tyr-Lys (HSG)-Lys(Tscg-Cys)-NH$_2$ (SEQ ID NO: 1) (IMP 245)

The peptide was synthesized by the usual double coupling procedure as described for the synthesis of IMP 192. The tri-t-butyl DOTA was added to the C-terminus of the peptide with a single benzotriazole-1-yl-oxy-tris-(dimethylamino)-phosphonium hexafluorophosphate (BOP) coupling using 5 eq of protected DOTA for 16 hr. The resin was then capped with acetic anhydride. The Aloc groups on the side chains were removed using the palladium catalyst and the N-trityl-HSG groups were added as described for the synthesis of IMP 243. The product was cleaved from the resin and purified by HPLC to afford 0.2385 g of product, from four fractions, after lyophilization. ESMS MH$^+$ 1832

Example 38

Tc-99m Kit Formulation

A formulation buffer was prepared which contained 22.093 g hydroxypropyl-β-cyclodextrin, 0.45 g 2,4-dihydroxybenzoic acid, 0.257 g acetic acid sodium salt, and 10.889 g α-D-glucoheptonic acid sodium salt dissolved in 170 mL nitrogen degassed water. The solution was adjusted to pH 5.3 with a few drops of 1 M NaOH then further diluted to a total volume of 220 mL. A stannous buffer solution was prepared by diluting 0.2 mL of SnCl$_2$ (200 mg/mL) with 3.8 mL of the formulation buffer. The peptide, IMP 245 (0.0029 g), was dissolved in 1 mL 1.6×10$^{-3}$ M InCl$_3$ in 0.1 M HCl. The peptide solution was mixed with 2 mL 0.5 M NH$_4$OAc and allowed to incubate at room temperature for 15 min. The formulation buffer, 75 mL, and 0.52 mL of the stannous buffer were then added to the peptide solution. The peptide solution was then filtered through a 0.22 m Millex GV filter in 1.5 mL aliquots into 3 mL lyophilization vials. The filled vials were frozen immediately, lyophilized and crimp sealed under vacuum.

Example 39

Tc-99m Labeling of IMP 245

High Temperature (Boiling Water Bath)

The pertechnetate solution (29 mCi) in 1.5 mL of saline was added to the kit. The kit was incubated at room temperature for 10 min and heated in a boiling water bath for 15 min. The kit was cooled to room temperature before use.

Low Temperature (37° C.)

The pertechnetate solution (25 mCi) in 1.5 mL of saline was added to the kit. The kit was incubated at room temperature for 14 min and heated in a 37° C. water bath for 18 min. The kit was cooled to room temperature before use. The HPLC retention time for this label is slightly different because a different injector was used.

Example 40

Peptide Analysis (HPLC) of IMP 245

The peptide was analyzed by reverse phase HPLC and size exclusion HPLC (shown below). The size exclusion HPLC traces indicated that the peptide binds to two mMU-9×m679 and two hMN-14×m679 bi-specific antibodies (see "A Universal Pre-Targeting System for Cancer Detection and Therapy Using Bi-specific Antibody," Sharkey, R. M., McBride, W. J., Karacay, H., Chang, K., Griffiths, G. L., Hansen, H. J., and Goldenberg, D. M., the entire contents of which are incorporated by reference herein). The reverse phase HPLC analysis shows several small peaks before the main peak and heat did not seem to significantly alter the ratio of the small peaks to the large peak.

Recovery from SEC:
Tc-99m IMP 245 Alone 54%,
Tc-99m IMP 245+hMN-14×m679 66%,
Tc-99m IMP 245+mMU-9×m679 66%.

Example 41

Serum Stability of IMP 245

An aliquot of the Tc-99m IMP 245, 50 L, was diluted with 470 L of fresh mouse serum and incubated at 37° C. Aliquots were removed and analyzed by reverse phase HPLC at 2.5 hr and 19 hr. The peptide appeared to be relatively stable.

Example 42

Synthesis of Cold Rhenium Oxo Complex of IMP 245

The Rhenium oxo complex was made by mixing 0.0504 g of IMP 245 with 0.0045 g of ReOBr$_4$ N(bu)$_4$ (synthesized by the method of Cotton et. al.) and 50 L DIEA in 1 mL DMF for five days at room temperature. The entire reaction mixture was purified by HPLC to afford 0.0118 g of the desired product. ESMS MH+ 2031

Example 43

Tc-99m Kit Formulation (Gentisic Acid Version)

The peptide, IMP 245 (0.0029 g, 1.58×10$^{-6}$ mol) was dissolved in 2.0 mL of 0.5 M NH$_4$OAc pH 5.5 buffer, which contained 0.0020 g of InCl$_3$. The peptide solution was heated at 50° C. for 17 min. A formulation buffer was prepared from 22.093 g hydroxypropyl-β-cyclodextrin (HPCD), 0.450 g 2,4-dihydroxybenzoic acid (gentisic acid), 0.257 g Acetic acid sodium salt, 10.889 g α-D-glucoheptonic acid and dissolved in 170 mL nitrogen purged DI water. The solution was adjusted to pH 5.30 with a few drops of 1M NaOH and diluted to a final volume of 220 mL with DI water. The formulation buffer was then sterile filtered through a 0.22 μm filter. A stannous buffer was prepared by diluting 0.2 mL (200 mg/mL SnCl$_2$ in 6 M HCl) with 3.8 mL of the formulation buffer in an argon purged sterile vial. The peptide solution was then mixed with 76 mL of the formulation buffer and 0.56 mL of the stannous buffer. The solution was then dispensed in 1.5 mL aliquots through a Millex GV 0.22 mm filter into 3 mL lyophilization vials. The filled vials were immediately frozen on dry ice and lyophilized. The kits were sealed under vacuum at the end of the lyophilization cycle. Each kit contained 55 μg of the peptide and was formulated for a 1.5 mL reconstitution volume of $^{99m}$TcO$_4^-$ in saline.

Example 44

Tc-99m Kit Formulation (Ascorbic Acid Formulation)

The Tc-99m kits formulated with ascorbic acid were prepared in the same manner as the gentisic acid kits except 0.222 g of L-ascorbic acid was used instead of gentisic acid.

Example 45

Tc-99m Kit Labeling

The kit was reconstituted with 1.5 mL of $^{99m}$TcO$_4^-$ in saline (0.5 to 70 mCi) and incubated at room temperature for 10 min. The kit was then heated in a boiling water bath for 15 min and allowed to cool to room temperature before use.

Example 46

Labeling & Stability of Tc-99m/In IMP 245

Early labeling attempts demonstrated that it was preferable to fill the DOTA with cold indium to afford a high yield of Tc-99m/In IMP 245 from the kits. The gentisic acid formulation gave a cleaner initial labeling of the peptide when labeled at 30 mCi Tc-99m in 1.5 mL but the ascorbic acid formulation afforded a kit with much greater stability when the peptide was stored overnight at room temperature. Early stability studies at 37° C. in fresh mouse serum showed that the Tc-99m labeled peptide was as stable in serum as in the kit. HPLC analysis on an expanded gradient revealed that the labeled peptide had two peaks. The two peaks were probably due to the formation of syn and anti Tc oxo species. The ratio of the peaks can change depending on the peptide sequence, formulation and labeling conditions.

Example 47

Y-90 and In-111 Labeling of IMP 245

The peptide was dissolved in 0.5 M NH$_4$OAc, pH 3.08 at 2.2×10$^{-3}$M (peptide). An aliquot, 3.5 μL of the peptide solution was then mixed with 165 μL of 0.5 M NH$_4$OAc pH 3.93 and 6 μL of the Y-90 solution. The mixture was then heated for 20 min at 85-95° C. Reverse phase HPLC showed that the peptide labeled well.

An analogous labeling process was attempted using In-111 under a number of conditions none of which led to a clean, labeled product. Subsequent-HPLC analysis of the cold peptide showed that it had formed several new peaks. The peptide was probably forming disulfides on storage. The Tc/Re ligand was then pre-filled with cold rhenium to stabilize the peptide for Y-90, Lu-177, and In-111 labeling.

Example 48

In-111 Labeling of ReO IMP 245

The peptide, 0.0025 g ReO IMP 245 (MH+ 2031) was dissolved in 560 μL 0.5 M NH$_4$OAc pH 3.98 buffer (2.2×10$^{-3}$ M peptide). An aliquot, 2.7 μL of the ReO IMP 245 was mixed with 2 μL of In-111 (573 μCi) and 150 μL of the 0.5 M NH$_4$OAc pH 3.98 buffer. The solution was then heated in a boiling water bath for 20 min. HPLC analysis showed a clean, labeled peak with a comparable retention time to Tc-99m/In IMP 245.

Example 49

Generation of Peptides Suitable for Radiolabeling with $^{90}$Y, $^{111}$In, and $^{177}$Lu Preparation of bsMAbs The bi-specific F(ab')$_2$ antibody composed of Fab' fragments of humanized MN-14 anti-CEA or murine Mu-9 anti-CSAp and murine 679 were prepared using PDM as the crosslinker. The F(ab')$_2$ of each parental antibody was first prepared. For hMN-14 or Mu-9, the F(ab')$_2$ was reduced with 1 mM DTT to Fab'-SH, which was diafiltered into a pH 5.3 acetate buffer containing 0.5 mM EDTA (acetate/EDTA buffer) to remove DTT, concentrated to 5-10 mg/mL, and stored at 2-8° C. until needed. For 679, the F(ab')$_2$ was reduced with 1 mM DTT to Fab'-SH , which was then diluted with 5 volumes of the acetate/EDTA buffer, followed by a rapid addition of 20 mM PDM (prepared in 90% DMF) to a final concentration of 4 mM. After stirring at room temperature for 30 minutes, the resulting solution (containing 679 Fab'-PDM) was diafiltered into the acetate/EDTA buffer until free PDM is minimum, and concentrated to 5-10 mg/mL. A solution of hMN-14 Fab'-SH or Mu-9 Fab'-SH was then mixed with a solution of 679 Fab'-PDM at a 1:1 ratio based on the amount of Fab'. Adding cysteine to a final concentration of 2 mM quenched the conjugation reaction and the desirable bi-specific conjugate (~100 kDa) was obtained following purification on a Superdex 200-packed column (Amersham, Pharmacia Bio, Piscataway, N.J.). The bi-specific conjugates were analyzed by SE-HPLC, SDS-PAGE, and IEF. For hMN-14×m679 F(ab')$_2$, the bi-specificity was demonstrated by BIAcore as well as by SE-HPLC. In addition, the affinity of hMN-14×679 for HSG was determined by BlAcore analysis using a CM-5 chip derived with a peptide containing a single HSG substituent and a thiol by the method recommended by the manufacturer (Biacore, Inc., Piscataway, N.J. 08854).

For biodistribution studies, the hMN-14×m679 F(ab')$_2$ was radioiodinated with $^{125}$INa (Perkin Elmer Life Science, Inc. Boston, Mass.) by the chloramine-T method (20), and purified using centrifuged size-exclusion columns. Quality assurance testing found <5% unbound radioiodine by ITLC, >90% of the product migrating as a single peak by SE-HPLC (Bio-Sil SE 250, Bio Rad, Hercules, Calif.), and >90% of the radiolabeled product shifting to a higher molecular weight with the addition of an excess of CEA (Scripps Laboratories, San Diego, Calif.). $^{125}$I-mMu-9×m679 bsMAb was tested in a similar manner, using a partially purified extract from GW-39 human colon xenografts as a source of CSAp, which shifted the elution profile of the mMu-9-x679 bsMAb to the void fraction of the SE-HPLC column.

Humanized MN-14 (hMN-14) Fab'-SH was prepared in a similar manner as described previously. $^{99m}$Tc-pertechnetate (30 mCi) was added directly to the lyophilized hMN-14-Fab'-SH (1.0 mg) and injected in animals within 30 minutes. This product had 3.0% unbound $^{99m}$Tc by ITLC and an immunoreactive fraction of 92%.

Radiolabeling of Peptides

The divalent HSG-peptide, IMP 241 used for $^{90}$Y-, $^{77}$Lu- and $^{111}$In-radiolabeling contains a DOTA ligand to facilitate the binding of these radiometals. IMP 241 was dissolved in 0.5 M ammonium acetate (pH 4.0) to a concentration of $2.2 \times 10^{-3}$ M. $^{90}$YCl$_3$ was obtained from Perkin Elmer Life Sciences, Inc. (Boston, Mass.), $^{111}$InCl$_3$ from IsoTex Diagnostics (Friendswood, Tex.), and $^{177}$Lu from the Research Reactor Facility, University of Missouri-Columbia, (Columbia, Mo.).

$^{111}$n-IMP 241 was prepared by mixing 3 mCi of $^{111}$InCl$_3$ in a plastic conical vial with 0.5 M ammonium acetate, pH 4.0 (3× volume of $^{111}$InCl$_3$) and 2.3 µL of IMP 241 ($2.2 \times 10^{-3}$ M in 0.5 M ammonium acetate, pH 4.0). After centrifugation, the mixture was heated in a boiling water bath for 30 min and cooled. The mixture was centrifuged and DTPA was added to a final concentration of 3 mM. After 15 min at room temperature, the final volume was raised to 1.0 mL with 0.1 M sodium acetate, pH 6.5. The amount of unbound isotope was determined by reverse phase HPLC and ITLC developed in saturated sodium chloride solution. Reverse phase HPLC analyses were performed on a Waters 8×100 mm radial Pak cartridge filled with a C-18 Nova-Pak 4 µm stationary phase. The column was eluted at 1.5 mL/min with a linear gradient of 100% A (0.075% TFA in water) to 55% A and 45% B where B was 0.075 % of TFA in 75% acetonitrile and 25% water over 15 min. At 15 min, solvent was switched to 100% B and maintained there for 5 min before re-equilibration to initial conditions. Reverse HPLC analyses showed a single peak at 11.8 min. Analysis of $^{111}$In-IMP 241 mixed with excess m679 IgG on a Bio-Sil SE 250 HPLC gel filtration column showed a peak at the retention time of the antibody indicating binding to the antibody.

IMP-241 was radiolabeled with $^{90}$Y by adding to 15 mCi of $^{90}$YCl$_3$, 3-times the volume of 0.5 M ammonium acetate, pH 4.0 and 83.2 µL of IMP 241 ($1.1 \times 10^{-4}$ M in 0.5 M ammonium acetate, pH 4.0), and ascorbic acid to a final concentration of 6.75 mg/mL. The mixture was heated in a boiling water bath for 30 min, and after cooling to room temperature, DTPA was added to a final concentration of 5 mM. Fifteen minutes later, the final volume was increased to 1.0 mL with 0.1 M sodium acetate, pH 6.5. ITLC strips developed in saturated sodium chloride solution showed <0.2% unbound isotope. Analysis of $^{90}$Y-IMP 241 mixed with an excess of m679 IgG by SE-HPLC showed a peak at the retention time of the antibody indicating binding to the antibody.

The stability of the radiolabeled peptides was tested in mouse serum by diluting each of the radiolabeled peptides 10-fold in mouse serum and incubating the solution at 37° C. Samples were removed at 1, 3, and 24 h and analyzed by reverse-phase HPLC.

In Vivo Pretargeting Studies

GW-39, a CEA-producing human colon cancer cell line (See, Goldenberg, D. M. and Hansen, H. J, Carcinoembryonic antigen present in human colonic neoplasms serially propagated in hamsters, *Science,* 175:1117-18 (1972)) was serially propagated in nude mice by mincing 1-2 grams of tumor in sterile saline, passing the minced mixture through a 50-mesh wire screen, and adjusting the saline volume to a final ration of 10 ml saline per gram tumor. Female NCr nude mice (Charles River Laboratories, Inc., Fredrick Md. or Taconic, Germantown, N.Y.) approximately 6 weeks of age were implanted subcutaneously with 0.2 ml of this suspension. Two to three weeks after implantation of tumors, animals were injected with the radiolabeled peptide alone, or for pretargeting, with the bsMAb followed 1 to 2 days later with the radiolabeled peptide. For pretargeting, $1.5 \times 10^{-10}$ moles (15 µg; 6 µCi $^{125}$I) of the bsMAb was injected intravenously (0.1 to 0.2 mL) followed with an intravenous injection (0.1 to 0.2 mL) of $^{111}$In-IMP-241 ($1.5 \times 10^{-11}$ moles, 8-10 µCi), $^{177}$Lu-IMP-241 ($1.5 \times 10^{-11}$ moles, 5 µCi), or $^{99m}$Tc-IMP-243 ($1.5 \times 10^{-11}$, 25-30 µCi). At the designated times after the peptide injection, animals were anesthetized, bled by cardiac puncture, and then euthanized prior to necropsy. Tissues were removed, weighed and counted by ganima scintillation using appropriate windows for each radionuclide along with standards prepared from the injected materials. When dual isotope counting was used, appropriate backscatter correction was made. GI tissues (stomach, small intestine and large intestine were weighed and counted with their contents. Data are expressed as the percent injected dose per gram tissue (% ID/g) and the ratio of the percentages in the tumor to the normal tissues (T/NT). All values presented in the tables and figures represent the mean and standard deviation of the calculated values with the number of animals used for each study provided therein.

Results

TABLE 20

Biodistribution of $^{111}$In-IMP-241. Nude mice were injected i.v. with the peptide and necropsied at the times indicated. Values are the means ± SD (n = 4).

| Tissue | 30 minutes % ID/g | 3 hour % ID/g | 24 hour % ID/g |
| --- | --- | --- | --- |
| Tumor | 1.42 ± 0.36 | 0.10 ± 0.03 | 0.03 ± 0.02 |
| (weight, g) | (0.242 ± 0.245) | (0.179 ± 0.053) | (0.239 ± 0.046) |
| Liver | 0.20 ± 0.03 | 0.07 ± 0.01 | 0.06 ± 0.01 |
| Spleen | 0.16 ± 0.03 | 0.04 ± 0.01 | 0.04 ± 0.01 |
| Kidney | 4.07 ± 0.89 | 2.13 ± 0.21 | 1.72 ± 0.69 |
| Lungs | 0.47 ± 0.07 | 0.06 ± 0.02 | 0.02 ± 0.006 |
| Blood | 0.39 ± 0.10 | <0.01[a] | <0.01[a] |
| Stomach | 0.17 ± 0.15 | 0.19 ± 0.25 | 0.01 ± 0.005 |
| Sm Int | 0.40 ± 0.20 | 0.54 ± 0.72 | 0.02 ± 0.006 |
| Lg Int | 0.09 ± 0.01 | 0.11 ± 0.03 | 0.03 ± 0.004 |

[a]Radioactivity concentration below threshold of detection.

TABLE 21

Biodistribution of $^{177}$Lu-IMP-241. Nude mice were injected i.v. with the peptide and necropsied at the times indicated. Values are the means ± SD (n = 5).

| Tissue | 1 hour % ID/g | 3 hour % ID/g | 24 hour % ID/g |
|---|---|---|---|
| Tumor | 0.81 ± 0.20 | 0.14 ± 0.08 | 0.03 ± 0.01 |
| (weight, g) | (0.517 ± 0.069) | (0.665 ± 0.261) | (0.538 ± 0.302) |
| Liver | 0.11 ± 0.01 | 0.08 ± 0.01 | 0.08 ± 0.01 |
| Spleen | 0.11 ± 0.06 | 0.02 ± 0.01 | 0.05 ± 0.01 |
| Kidney | 3.68 ± 0.57 | 2.52 ± 0.42 | 1.76 ± 0.53 |
| Lung | 0.20 ± 0.06 | 0.05 ± 0.01 | 0.03 ± 0.01 |
| Blood | 0.15 ± 0.04 | <0.01[a] | <0.01[a] |
| Stomach | 0.09 ± 0.08 | 0.08 ± 0.12 | 0.03 ± 0.01 |
| Sm. Int | 0.29 ± 0.23 | 0.21 ± 0.32 | 0.03 ± 0.01 |
| Lg Int | 0.05 ± 0.02 | 0.36 ± 0.45 | 0.06 ± 0.04 |

[a]Radioactivity concentration below threshold of detection.

TABLE 22

Biodistribution of $^{99m}$Tc-IMP-243 and $^{99m}$Tc-IMP-245. Nude mice were injected i.v. with the peptide and necropsied at the times indicated. Values are the means ± SD (n = 5).

| | $^{99m}$Tc-IMP-243 | | | $^{99m}$Tc-IMP-245 | |
|---|---|---|---|---|---|
| Tissue | 1 hour % ID/g | 3 hour % ID/g | 24 hour % ID/g | 30 min % ID/g | 3 hour % ID/g |
| Tumor | 1.23 ± 0.38 | 0.44 ± 0.13 | 0.10 ± 0.02 | 2.11 ± 0.36 | 0.29 ± 0.11 |
| (weight, g) | (0.450 ± 0.179) | (0.379 ± 0.168) | (0.439 ± 0.230) | (0.273 ± 0.032) | (0.275 ± 0.085) |
| Liver | 3.29 ± 1.46 | 1.29 ± 0.95 | 0.15 ± 0.04 | 0.63 ± 0.10 | 0.24 ± 0.02 |
| Spleen | 0.45 ± 0.09 | 0.22 ± 0.03 | 0.10 ± 0.04 | 0.46 ± 0.10 | 0.10 ± 0.01 |
| Kidney | 6.57 ± 1.13 | 4.12 ± 0.86 | 1.82 ± 0.33 | 8.63 ± 2.42 | 2.38 ± 0.21 |
| Lung | 1.09 ± 0.16 | 0.39 ± 0.04 | 0.10 ± 0.02 | 1.40 ± 0.32 | 0.17 ± 0.02 |
| Blood | 0.99 ± 0.12 | 0.43 ± 0.11 | 0.07 ± 0.01 | 1.56 ± 0.43 | 0.19 ± 0.02 |
| Stomach | 1.84 ± 0.55 | 0.68 ± 0.31 | 0.14 ± 0.06 | 0.82 ± 0.82 | 0.35 ± 0.15 |
| Sm. Int | 24.3 ± 4.75 | 2.53 ± 0.95 | 0.08 ± 0.02 | 1.19 ± 0.70 | 0.53 ± 0.33 |
| Lg Int | 0.63 ± 0.71 | 40.0 ± 10.4 | 0.17 ± 0.06 | 0.25 ± 0.05 | 1.13 ± 0.20 |

TABLE 23

Pretargeting of $^{99m}$Tc-IMP-243 using hMN-14 x m679 F(ab')$_2$ bsMAb

| | 3 hour after Peptide Injection (n = 5) | | | 24 hour after Peptide Injection (n = 4) | | |
|---|---|---|---|---|---|---|
| | $^{125}$I-bsMAb | $^{99m}$Tc-IMP-243 | | $^{125}$I-bsMAb | $^{99m}$Tc-IMP-243 | |
| Tissue | % ID/g | % ID/g | T/NT | % ID/g | % ID/g | T/NT |
| Tumor | 4.78 ± 1.11 | 12.25 ± 3.32 | — | 2.24 ± 0.53 | 7.36 ± 3.19 | — |
| weight, g) | (0.547 ± 0.265) | | | (0.390 ± 0.265) | | |
| Liver | 1.17 ± 0.19 | 2.00 ± 0.35 | 6.2 ± 1.5 | 0.27 ± 0.08 | 0.51 ± 0.13 | 14.4 ± 4.4 |
| Spleen | 2.24 ± 0.57 | 1.55 ± 0.43 | 8.4 ± 2.9 | 0.60 ± 0.23 | 0.48 ± 0.15 | 15.9 ± 6.3 |
| Kidney | 0.81 ± 0.21 | 4.52 ± 0.79 | 2.7 ± 0.5 | 0.20 ± 0.05 | 2.08 ± 0.38 | 3.5 ± 1.3 |
| Lungs | 1.02 ± 0.29 | 2.41 ± 0.60 | 5.3 ± 1.7 | 0.24 ± 0.04 | 0.53 ± 0.12 | 14.1 ± 4.9 |
| Blood | 1.48 ± 0.35 | 5.31 ± 1.32 | 2.4 ± 0.6 | 0.41 ± 0.08 | 1.08 ± 0.29 | 6.9 ± 2.3 |
| Stomach | 7.61 ± 3.33 | 1.51 ± 0.64 | 9.5 ± 4.6 | 0.57 ± 0.26 | 0.27 ± 0.14 | 27.8 ± 1.5 |
| Sm Int. | 0.51 ± 0.15 | 5.44 ± 2.42 | 2.4 ± 0.7 | 0.10 ± 0.03 | 0.37 ± 0.21 | 22.2 ± 8.0 |
| Lg Int. | 1.22 ± 0.10 | 24.79 ± 2.82 | 0.5 ± 0.2 | 0.09 ± 0.04 | 0.80 ± 0.48 | 10.4 ± 3.3 |

TABLE 24

Pretargeting of $^{99m}$Tc-IMP-245 using hMN-14 x m679 F(ab')$_2$ bsMAb (24 h clearance of the bsMAb)

| | 1 hour after Peptide Injection (n = 5) | | | 3 hour after Peptide Injection (n = 5) | | | 24 hour after Peptide Injection (n = 5) | | |
|---|---|---|---|---|---|---|---|---|---|
| | $^{125}$I-bsMAb | $^{99m}$Tc-IMP-245 | | $^{125}$I-bsMAb | $^{99m}$Tc-IMP-245 | | $^{125}$I-bsMAb | $^{99m}$Tc-IMP-245 | |
| Tissue | % ID/g | % ID/g | T/NT | % ID/g | % ID/g | T/NT | % ID/g | % ID/g | T/NT |
| Tumor | 3.41 ± 1.19 | 10.1 ± 4.6 | — | 3.31 ± 0.81 | 14.2 ± 5.27 | — | 1.5 ± 0.7 | 5.0 ± 2.6 | — |
| weight, g) | (0.304 ± 0.089) | | | (0.383 ± 0.052) | | | (0.335 ± 0.129) | | |
| Liver | 0.35 ± 0.14 | 1.10 ± 0.22 | 10.1 ± 0.5 | 0.44 ± 0.11 | 0.71 ± 0.13 | 19.7 ± 6.0 | 0.12 ± 0.04 | 0.20 ± 0.03 | 23.4 ± 10.1 |

TABLE 24-continued

Pretargeting of $^{99m}$Tc-IMP-245 using hMN-14 x m679 F(ab')$_2$ bsMAb
(24 h clearance of the bsMAb)

| | 1 hour after Peptide Injection (n = 5) | | | 3 hour after Peptide Injection (n = 5) | | | 24 hour after Peptide Injection (n = 5) | | |
|---|---|---|---|---|---|---|---|---|---|
| | $^{125}$I-bsMAb | $^{99m}$Tc-IMP-245 | | $^{125}$I-bsMAb | $^{99m}$Tc-IMP-245 | | $^{125}$I-bsMAb | $^{99m}$Tc-IMP-245 | |
| Tissue | % ID/g | % ID/g | T/NT | % ID/g | % ID/g | T/NT | % ID/g | % ID/g | T/NT |
| Spleen | 0.62 ± 0.15 | 0.66 ± 0.13 | 16.4 ± 9.7 | 0.75 ± 0.17 | 0.41 ± 0.06 | 33.7 ± 9.6 | 0.15 ± 0.03 | 0.13 ± 0.03 | 43.4 ± 26.5 |
| Kidney | 0.33 ± 0.05 | 4.80 ± 0.98 | 2.3 ± 1.4 | 0.28 ± 0.07 | 2.68 ± 0.50 | 5.2 ± 1.6 | 0.08 ± 0.02 | 0.89 ± 0.13 | 5.5 ± 2.8 |
| Lungs | 0.28 ± 0.06 | 1.57 ± 0.40 | 7.3 ± 5.1 | 0.26 ± 0.05 | 0.88 ± 0.14 | 16.0 ± 5.2 | 0.10 ± 0.01 | 0.14 ± 0.02 | 36.1 ± 21.8 |
| Blood | 0.47 ± 0.07 | 4.16 ± 0.98 | 2.4 ± 0.6 | 0.44 ± 0.09 | 2.23 ± 0.39 | 6.3 ± 1.7 | 0.14 ± 0.02 | 0.19 ± 0.02 | 26.3 ± 13.3 |
| Stomach | 0.92 ± 0.35 | 0.43 ± 0.06 | 23.5 ± 11.2 | 1.19 ± 0.83 | 0.41 ± 0.45 | 57.1 ± 29.1 | 0.21 ± 0.05 | 0.06 ± 0.02 | 96.9 ± 68.7 |
| Sm Int. | 0.12 ± 0.03 | 0.96 ± 0.11 | 10.5 ± 4.8 | 0.12 ± 0.05 | 0.76 ± 0.23 | 18.7 ± 4.3 | 0.04 ± 0.01 | 0.10 ± 0.04 | 58.7 ± 36.8 |
| Lg Int. | 0.18 ± 0.06 | 0.26 ± 0.14 | 47.8 ± 32.6 | 0.19 ± 0.08 | 0.97 ± 0.46 | 16.1 ± 7.4 | 0.04 ± 0.01 | 0.17 ± 0.08 | 30.2 ± 9.3 |

TABLE 25

Tumor/nontumor ratios $^{99m}$Tc-hMN-14 Fab' in GW-39 tumor-bearing nude mice 3 h after injection. (n = 5)

| Tissue | $^{99m}$Tc-hMN-14 Fab' |
|---|---|
| Liver | 0.2 ± 0.02 |
| Spleen | 0.9 ± 0.4 |
| Kidney | 0.02 ± 0.001 |
| Lungs | 0.7 ± 0.1 |
| Blood | 1.0 ± 0.01 |

TABLE 26

Pretargeting of $^{111}$In-IMP-241 using hMN-14 x m679 F(ab')$_2$ bsMAb
(24 h bsMAb clearance)

| | $^{125}$I-bsMAb | $^{111}$In-241 | |
|---|---|---|---|
| Tissue | % ID/g | % ID/g | T/NT |
| *3 hours after $^{111}$In-IMP-241 Injection (n = 5)* | | | |
| Tumor (0.254 ± 147 g) | 2.92 ± 0.41 | 11.3 ± 2.2 | — |
| Liver | 0.44 ± 0.24 | 0.53 ± 0.14 | 22.2 ± 6.3 |
| Spleen | 0.94 ± 0.41 | 0.42 ± 0.12 | 27.8 ± 5.9 |
| Kidney | 0.44 ± 0.17 | 4.61 ± 0.71 | 2.5 ± 0.5 |
| Lungs | 0.49 ± 0.24 | 0.83 ± 0.23 | 14.1 ± 2.8 |
| Blood | 0.79 ± 0.24 | 1.44 ± 0.33 | 8.1 ± 2.1 |
| Stomach | 3.18 ± 2.27 | 0.11 ± 0.02 | 102.9 ± 15.2 |
| Sm. Intestine | 0.27 ± 0.15 | 0.23 ± 0.08 | 53.4 ± 14.4 |
| Lg. Intestine | 0.35 ± 0.18 | 0.31 ± 0.07 | 37.4 ± 9.2 |
| *24 hours after $^{111}$In-IMP-241 Injection (n = 4)* | | | |
| Tumor (0.203 ± 0.09 g) | 1.80 ± 0.34 | 6.87 ± 0.84 | — |
| Liver | 0.10 ± 0.03 | 0.31 ± 0.05 | 22.3 ± 2.5 |
| Spleen | 0.35 ± 0.20 | 0.40 ± 0.13 | 18.5 ± 5.6 |
| Kidney | 0.11 ± 0.02 | 2.60 ± 0.43 | 2.7 ± 0.5 |
| Lungs | 0.13 ± 0.02 | 0.29 ± 0.05 | 24.0 ± 5.7 |
| Blood | 0.23 ± 0.03 | 0.43 ± 0.10 | 16.4 ± 3.3 |
| Stomach | 0.21 ± 0.06 | 0.06 ± 0.01 | 116.9 ± 10.2 |
| Sm. Intestine | 0.05 ± 0.01 | 0.10 ± 0.02 | 67.3 ± 9.6 |
| Lg. Intestine | 0.04 ± 0.01 | 0.11 ± 0.03 | 66.0 ± 12.2 |
| *48 hours after $^{111}$In-IMP-241 Injection (n = 5)* | | | |
| Tumor (0.206 ± 0.073 g) | 1.32 ± 0.15 | 5.47 ± 1.03 | — |
| Liver | 0.06 ± 0.01 | 0.27 ± 0.05 | 20.4 ± 4.1 |
| Spleen | 0.24 ± 0.14 | 0.40 ± 0.05 | 13.6 ± 2.0 |
| Kidney | 0.07 ± 0.01 | 1.17 ± 0.21 | 4.7 ± 0.46 |
| Lungs | 0.07 ± 0.02 | 0.19 ± 0.04 | 28.9 ± 6.5 |
| Blood | 0.11 ± 0.02 | 0.17 ± 0.03 | 32.0 ± 7.2 |
| Stomach | 0.09 ± 0.03 | 0.04 ± 0.02 | 163.2 ± 53.9 |
| Sm. Intestine | 0.03 ± 0.01 | 0.07 ± 0.02 | 76.8 ± 16.2 |
| Lg. Intestine | 0.02 ± 0.01 | 0.07 ± 0.02 | 83.0 ± 16.8 |

TABLE 27

Pretargeting of $^{111}$In-IMP-241 using mMu-9 x m679 F(ab')$_2$ bsMAb
(48 h bsMAb clearance)

| | $^{125}$I-bsMAb | $^{111}$In-241 | |
|---|---|---|---|
| Tissue | % ID/g | % ID/g | T/NT |
| *3 hour After $^{111}$In-IMP-241 Injection* | | | |
| Tumor (0.164 ± 0.064 g) | 13.1 ± 4.36 | 17.8 ± 1.4 | — |
| Liver | 0.19 ± 0.03 | 0.56 ± 0.08 | 32.0 ± 3.0 |
| Spleen | 0.28 ± 0.12 | 0.46 ± 0.13 | 41.2 ± 10.6 |
| Kidney | 0.32 ± 0.04 | 3.63 ± 0.34 | 4.9 ± 0.5 |
| Lungs | 0.31 ± 0.05 | 0.92 ± 0.21 | 20.0 ± 2.9 |
| Blood | 0.55 ± 0.10 | 1.93 ± 0.63 | 9.7 ± 2.0 |
| Stomach | 0.75 ± 0.21 | 0.15 ± 0.07 | 130.2 ± 41.0 |
| Sm. Intestine | 0.11 ± 0.02 | 0.28 ± 0.12 | 70.5 ± 20.4 |
| Lg Intestine | 0.10 ± 0.02 | 0.20 ± 0.07 | 98.1 ± 27.9 |
| *24 hour After $^{111}$In-IMP-241 Injection* | | | |
| Tumor (0.214 ± 0.040 g) | 12.4 ± 4.2 | 17.5 ± 4.1 | — |
| Liver | 0.10 ± 0.02 | 0.44 ± 0.10 | 39.8 ± 6.5 |
| Spleen | 0.15 ± 0.05 | 0.35 ± 0.08 | 50.3 ± 7.1 |
| Kidney | 0.15 ± 0.03 | 2.28 ± 0.35 | 7.7 ± 1.9 |
| Lungs | 0.12 ± 0.02 | 0.31 ± 0.05 | 56.0 ± 6.0 |
| Blood | 0.22 ± 0.05 | 0.38 ± 0.12 | 47.6 ± 11.2 |
| Stomach | 0.17 ± 0.04 | 0.05 ± 0.01 | 377.6 ± 101.8 |
| Sm. Intestine | 0.05 ± 0.01 | 0.09 ± 0.02 | 195.7 ± 49.7 |
| Lg Intestine | 0.03 ± 0.01 | 0.08 ± 0.02 | 235.8 ± 58.4 |
| *48 hour After $^{111}$In-IMP-241 Injection* | | | |
| Tumor (0.213 ± 0.064 g) | 11.2 ± 5.5 | 12.7 ± 4.8 | — |
| Liver | 0.06 ± 0.01 | 0.29 ± 0.06 | 44.6 ± 16.2 |
| Spleen | 0.06 ± 0.01 | 0.25 ± 0.05 | 50.6 ± 14.1 |
| Kidney | 0.06 ± 0.01 | 0.99 ± 0.35 | 12.9 ± 2.6 |

TABLE 27-continued

Pretargeting of $^{111}$In-IMP-241 using mMu-9 × m679 F(ab')$_2$ bsMAb (48 h bsMAb clearance)

| Tissue | $^{125}$I-bsMAb % ID/g | $^{111}$In-241 % ID/g | T/NT |
|---|---|---|---|
| Lungs | 0.05 ± 0.01 | 0.14 ± 0.01 | 90.8 ± 32.3 |
| Blood | 0.07 ± 0.01 | 0.10 ± 0.02 | 127.8 ± 41.7 |
| Stomach | 0.10 ± 0.04 | 0.04 ± 0.01 | 338 ± 148.5 |
| Sm. Intestine | 0.02 ± 0.00 | 0.07 ± 0.01 | 189.9 ± 71.1 |
| Lg Intestine | 0.02 ± 0.01 | 0.07 ± 0.02 | 168.0 ± 40.9 |

TABLE 28

Comparison of $^{177}$Lu-IMP-241 and $^{111}$In-IMP-241 Pretargeting using the hMN-14 × m679 F(ab')$_2$ bsMAb (24 h bsMAb clearance)

| | Percent Injected Dose Per Gram | |
|---|---|---|
| Tissue | $^{177}$Lu-IMP-241 | $^{111}$In-IMP-241 |
| 3 hour After Radiolabeled Peptide Injection | | |
| Tumor | 9.71 ± 2.49 | 8.76 ± 2.31 |
| (weight, g) | (0.747 ± 0.243) | (0.536 ± 0.114) |
| Liver | 0.46 ± 0.08 | 0.57 ± 0.24 |
| Spleen | 0.36 ± 0.04 | 0.54 ± 0.30 |
| Kidney | 3.61 ± 0.43 | 3.00 ± 0.87 |
| Lungs | 0.64 ± 0.12 | 0.81 ± 0.33 |
| Blood | 1.48 ± 0.19 | 1.87 ± 0.97 |
| 24 hour After Radiolabeled Peptide Injection | | |
| Tumor | 2.59 ± 0.30 | 2.54 ± 1.04 |
| (weight, g) | (0.723 ± 0.138) | (0.405 ± 0.105) |
| Liver | 0.17 ± 0.04 | 0.19 ± 0.07 |
| Spleen | 0.29 ± 0.07 | 0.28 ± 0.10 |
| Kidney | 0.18 ± 0.03 | 0.25 ± 0.14 |
| Lungs | 0.17 ± 0.02 | 0.24 ± 0.07 |
| Blood | 0.36 ± 0.05 | 0.54 ± 0.20 |

TABLE 29

Dosimetry for $^{90}$Y- or $^{177}$Lu-labeled IMP-241 using the mMu-9 × m679 F(ab')$_2$ bsMAb

| | $^{90}$Y-IMP-241 | | $^{177}$Lu-IMP-241 | |
|---|---|---|---|---|
| Tissue | cGy/mCi | CGy (normalized)$^a$ | cGy/mCi | cGy (normalized)$^a$ |
| Tumor | 14,366 | 12,578 | 5580 | 13,721 |
| Blood | 416 | 364 | 124 | 305 |
| Liver | 551 | 482 | 161 | 394 |
| Lungs | 277 | 242 | 94 | 231 |
| Kidneys | 1713 | 1500 | 610 | 1500 |

$^a$Radiation absorbed doses are normalized to 1500 cGy to the kidneys

Radiolabeling of Peptides and Testing of BsMAbs

IMP-241's DOTA chelation group can be used with $^{111}$In, $^{90}$Y, and other radiometals, such as $^{177}$Lu. The peptide was radiolabeled with each of these radionuclides to specific activities of about 600, 1650, and 300 Ci/mmol, respectively. The lower specific activity for $^{177}$Lu was attributed to both the age of the product at the time it was used and the isotope production run that was not performed in a manner to optimize the specific activity of $^{177}$Lu. The specific activity of the $^{99m}$Tc-peptides was between 1500 and 1600 Ci/mmol. In each instance radiolabeling conditions were developed to ensure >98% incorporation of the radioactivity in the peptide so that no purification was required. Reverse phase HPLC indicated that when mixed with fresh mouse serum at 37° C., all of the peptides were stable over 24 h, retaining the original elution profile as seen after their preparation. HPLC analysis of the IMP-243 and 245 on an expanded gradient revealed that the labeled peptide had two peaks, likely due to the formation of syn and anti technetium oxo species.

FIG. 6 shows the binding of the hMN-14×m679 bsMAb to $^{111}$In-IMP-241 by SE-HPLC. Essentially all the radiolabeled peptide is shifted to the bsMAb elution time, and when CEA is first added to the bsMAb followed by the addition of the radiolabeled peptide, the entire amount of radioactivity shifts to the void fraction. Similar results were found with the mMu-9×m679 bsMAb when using the CSAp preparation (not shown). The kinetic binding of hMN-14×m679 F(ab')$_2$ bsMAb to the mono HSG peptide on the chip was evaluated by BIAcore and found to be KD=1.5×10$^{-9}$ M.

Peptide Biodistribution

For biodistribution purposes, IMP-241 was radiolabeled with the gamma-emitting radionuclides, $^{111}$In or $^{177}$Lu, to facilitate the peptide's detection in tissues, while IMP-243 and IMP-245 were radiolabeled with $^{99m}$Tc. In tumor-bearing nude mice, the $^{177}$Lu- and $^{111}$In-IMP-241 had similar distribution and clearance properties (Tables 20 and 21). In both instances, the peptide was cleared so rapidly from blood that within 3 hour after its injection, there was insufficient radioactivity in the blood to quantify accurately, but there was sufficient radioactivity in the major organs to permit quantitation. The radioactivity was eliminated from the body through renal excretion, with a small percentage of the injected activity lingering in the kidneys over the monitoring period. At an average kidney weight of 0.15 g, there was only about 0.6% of the total injected activity in the kidney at 0.5 to 1.0 h after injection. An additional group of animals given the $^{177}$Lu-IMP-241 was necropsied at 48 h, but since there was only enough radioactivity in the kidneys for accurate reporting, the data are not presented in the table. However, the $^{177}$Lu-IMP-241 in the kidneys had decreased to a level of 0.94±0.2% ID/g, which represented about a 45% decrease compared to the level seen at 24 h. The vast majority of the radioactivity was excreted in the urine, but there was also a very small fraction of the radioactivity that cleared through the GI tract. From 1.0 to 3.0 hours, about 0.6 to 0.7% of the total injected activity can be accounted for in all the GI tissues (i.e., stomach, small and large intestine). By 24 h, only 0.07% of the radioactivity was accounted for in all the GI tissues.

The tissue distribution of $^{99m}$Tc-IMP-243 was considerably different than the IMP-241 (Table 22). There was a slower clearance from the blood, a higher uptake in the liver, and a substantial fraction in the GI tract. For example, 1 hour after injection, the small intestine contained 24.3±4.75% ID/g of the $^{99m}$Tc-IMP-243, and by 3 h, the activity had shifted to the large intestine. By 24 h, the activity was fully cleared from the body. Thus, the radioactivity was not associated with the GI tissues per se, but was in the GI contents, as seen with the progression of the radioactivity through the small and large intestines. Another peptide, IMP-245, had a much smaller fraction of the radioactivity in the GI tissues. Liver and renal retention were also appreciable lower than that seen with $^{99m}$Tc-IMP-243.

Pretargeting Studies

The hMN-14×m679 F(ab')$_2$ bsMAb was used to test the pretargeting capabilities of the $^{99m}$Tc-IMP-243 and $^{99m}$Tc-IMP-245. The bsMAb was radiolabeled with $^{125}$I so that its distribution could be co-registered with either the $^{99m}$Tc- IMP-243 or IMP-245. The bsMAb was given to animals i.v., and after 24 h, the radiolabeled peptide was given and animals were necropsied 3 and 24 hours later. In the pretargeting setting, tumor uptake of the $^{99m}$Tc-IMP-243 was nearly 28 and 70 times higher than that seen with peptide alone at 3 and 24 h after its injection (Table 23). Tumor uptake was 12.25±3.32% ID/g at 3 h, reducing to 7.36±3.19 by 24 h. The reduction of $^{99m}$Tc-IMP-243 in the tumor over this time was not as high as the reduction of the bsMAb in the tumor, which dropped from 4.78±1.11% ID/g to 2.24±0.53% ID/g over this same period. Tumor/nontumor ratios for $^{99m}$Tc-IMP-243 were all greater than 2.0:1 within 3 hours, except for the large intestine where the peptide had not yet cleared, but this improved nearly 20-fold by 24 h. Tumor/blood ratios were 2.4±0.6 at 3 h after peptide injection. Tumor uptake for $^{99m}$Tc-IMP-245 was similar to that seen with $^{99m}$Tc-IMP-243 (Table 6), but tumor/nontumor ratios favored the $^{99m}$Tc-IMP-245, primarily because the bsMAb had cleared to a lower level in these animals than in the animals that had received the $^{99m}$Tc-IMP-243. However, $^{99m}$Tc-IMP-245 pretargeting also had lower GI uptake, even at 1 hour, and therefore this peptide has a distinct advantage over $^{99m}$Tc-IMP-243. Tumor/kidney ratios for $^{99m}$Tc-IMP-245 were higher than those obtained with $^{99m}$Tc-IMP-243. These biodistribution data suggest that pretargeting with $^{99m}$Tc-IMP-245 should provide better image contrast at an earlier time than that found with a directly radiolabeled Fab' fragment. It should also be emphasized that the tumor/kidney ratio using the $^{99m}$Tc-labeled peptides was substantially higher than an antibody fragment directly radiolabeled with $^{99m}$Tc-hMN-14 Fab' 3 h after its injection (Table 25).

Two different targeting systems were used in the evaluation of pretargeting the IMP-241 peptide, one system used a humanized anti-CEA antibody (hMN-14) while the other used a murine antibody to CSAp (mMu-9). Each bsMAb was prepared by chemically coupling its Fab' to the Fab' of the murine 679 MAb. For biodistribution studies, each bsMAb was radiolabeled with $^{125}$I so that its distribution could be assessed together with the IMP-241 which was radiolabeled with $^{111}$In. The amount of bsMAb and peptide injected in tumor-bearing nude mice was the same in each pretargeting system, but because the Mu-9 bsMAb took longer to clear from the blood than the hMN-14 bsMAb, the radiolabeled peptide was given at 48 h after the Mu-9 bsMAb compared to 24 h after the hMN-14 bsMAb. By using a 24-h delay for the hMN-14×m679 construct and a 48-h delay for the mMu-9×m679 construct, the blood levels of each bsMAb were similar, 0.79±0.24% ID/g and 0.55±0.10% ID/g, respectively. It was not unexpected to find a higher amount of the Mu-9 bsMAb in the tumor (13.1±4.36% ID/g) than the MN-14 bsMAb (2.92±0.41), since earlier studies comparing the targeting of the Mu-9 and anti-CEA antibodies had found Mu-9 to have a higher uptake and a longer retention in the GW-39 xenograft model than that seen with anti-CEA antibodies. With a higher amount of Mu-9 bsMAb in the tumor, a higher concentration of the peptide was achieved, reaching a level of 17.8±1.4% ID/g in just 3 hour after the peptide injection compared to 11.3±2.2% ID/g for the peptide in animals pretargeted with the hMN-14 bsMAb. Interestingly, the hMN-14 bsMAb was more efficient at binding the peptide, since the ratio of the % ID/g of the peptide compared to the bsMAb in the tumor was 3.9 for the hMN-14 bsMAb at 3 h compared to 1.4 for the Mu-9 bsMAb at this same time. However, $^{111}$In-IMP-241 was retained by the tumor in Mu-9 pretargeting system for a longer period of time, which corresponded to the extended time that the bsMAb was bound to the tumor. In each system, the peptide:bsMAb ratio observed at 3 h was maintained over the 48-h observation period, suggesting that the peptide was bound specifically by the bsMAb. Pretargeting increased tumor accretion of the $^{111}$In-IMP-241 nearly 100-fold compared to the peptide alone (refer Table 20). With pretargeting, tumor/nontumor ratios were also significantly improved for all tissues as compared to that seen with the $^{111}$In-241 peptide alone, regardless of which bsMAb pretargeting system was used. Overall, tumor/nontumor ratios for the $^{111}$In-IMP-241 were significantly higher in the Mu-9 bsMAb system, especially over time.

Regardless of whether IMP-241 was radiolabeled with $^{177}$Lu or $^{111}$In, the pretargeting results were the same. As seen in Table 27, using the hMN-14 bsMAb pretargeting system, the % ID/g of the $^{177}$Lu-IMP-241 was identical to that seen with $^{111}$In-IMP-241. Because $^{111}$In-IMP-241's distribution mimicked $^{177}$Lu-IMP-241, and since $^{111}$In has also been used as a surrogate for predicting $^{90}$Y-distribution, an extended biodistribution study was performed using the $^{111}$In-IMP-241 and the mMu-9×m679 F(ab')$_2$ bsMAb. As shown in FIG. 7, as a consequence of extended retention of the Mu-9 antibody in the tumor, there was also an excellent retention of the radiolabeled peptide in the tumor. Using these data, radiation dose estimates were modeled for $^{90}$Y and $^{177}$Lu. $^{90}$Y, because of its higher beta-radiation energy (2.27 MeV$_{max}$), delivers a higher radiation dose to the tumor than $^{177}$Lu (495 keV$_{max}$) on a per mCi basis. However, in order to make a better comparison, the radiation doses were normalized to reflect an identical radiation to a dose-limiting organ. In this case, 1500 cGy to the kidneys was selected as a dosage that should be tolerated, but could result in similar toxicities. When the absorbed doses to the tissues were normalized, the data suggest that $^{177}$Lu-IMP-241 would potentially deliver the same dose to the tumor as $^{90}$Y-IMP-241. If the kidneys were able to tolerate 1500 cGy, then the tumor would receive nearly 12,000 cGy, a radiation dose that should be lethal to most solid tumors.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

Additional references of interest include the following:

Arano Y, Uezono T, Akizawa H, Ono M, Wakisaka K, Nakayama M, Sakahara H, Konishi J, Yokoyama A., "Reassessment of diethylenetriaminepentaacetic acid (DTPA) as a chelating agent for indium-111 labeling of polypeptides using a newly synthesized monoreactive DTPA derivative," *J Med Chem*. Aug. 30, 1996; 39(18): 3451-60.

Bamias, A., and Epenetos, A. A. Two-step strategies for the diagnosis and treatment of cancer with bioconjugates. *Antibody, Immunoconjugates, Radiopharm.* 1992; 5: 385-395.

Barbet, J., Peltier, P., Bardet,. S., Vuillez, J P., Bachelot, I., Denet, S., Olivier, P., Lecia, F., Corcuff, B., Huglo, D., Proye, C., Rouvier, E., Meyer, P., Chatal, J. F. Radioimmunodetection of medullary thyroid carcinoma using indium-111 bivalent hapten and anti-CEA×anti-DTPA-indium bispecifc antibody. *J. Nucl. Med.* 1998; 39:1172-1178.

Bos, E S., Kuijpers, W H A., Meesters-Winters, M., Pham, D T., deHaan, A S., van Doormalen, Am., Kasperson, F. M., vanBoeckel, C A A and Gouegeon-Bertrand, F. In vitro evaluation of DNA-DNA hybridization as a two-step approach in radioimmunotherapy of cancer. *Cancer Res.* 1994; 54:3479-3486.

Carr et al., WO00/34317.

Gautherot, E., Bouhou, J., LeDoussal, J-M., Manetti, C., Martin, M., Rouvier, E., Barbet, J. Therapy for colon carcinoma xenografts with bi-specific antibody-targeted, iodine-131-labeled bivalent hapten. Cancer suppl. 1997; 80: 2618-2623.

Gautherot, E., Bouhou, J., Loucif, E., Manetti, C., Martin, M., LeDoussal, J. M., Rouvier, E., Barbet, J. Radioimmunotherapy of LS174T colon carcinoma in nude mice using an iodine-131-labeled bivalent hapten combined with an anti-CEA×anti-indium-DTPA bi-specific antibody. *J. Nucl. Med. Suppl.* 1997; 38: 7p.

Goodwin, D. A., Meares, C F., McCall, M J., McTigue, M., Chaovapong, W. Pre-targeted inmmunoscintigraphy of murine tumors with indium-111-labeled bifunctional haptens. *J. Nucl. Med.* 1988; 29:226-234.

Greenwood, F. C. and Hunter, W. M. The preparation of I-131 labeled human growth hormone of high specific radioactivity. *Biochem.* 1963; 89:114-123.

Hawkins, G. A., McCabe, R. P., Kim, C.-H., Subramanian, R., Bredehorst, R., McCullers, G. A., Vogel, C.-W., Hanna, M. G. Jr., and Pomata, N. Delivery of radionuclides to pretargeted monoclonal antibodies using dihydrofolate reductase and methotrexate in an affinity system. *Cancer Res.* 1993; 53: 2368-2373.

Kranenborg, M. h., Boerman, O. C., Oosterwijk-Wakka, j., weijert, M., Corstens, F., Oosterwijk, E. Development and characterization of anti-renal cell carcinoma×anti-chelate bi-specific monoclonal antibodies for two-phase targeting of renal cell carcinoma. *Cancer Res.* (suppl) 1995; 55: 5864s-5867s Losman M. J., Qu Z., Krishnan I. S., Wang J., Hansen H. J., Goldenberg D. M., Leung S. O. *Clin. Cancer Res.* 1999; 5(10 Suppl.):3101s-3105s.

Penefsky, H. S. A centrifuged column procedure for the measurement of ligand binding by beef heart F1. Part G. *Methods Enzymol.* 1979; 56:527-530.

Schuhmacher, J., Klivenyi, G., Matys, R., Stadler, M., Regiert, T., Hauser, H., Doll, J., Maier-Borst, W., Zoller, M. Multistep tumor targeting in nude mice using bi-specific antibodies and a gallium chelate suitable for inmmunoscintigraphy with positron emission tomography. *Cancer Res.* 1995; 55, 115-123.

Sharkey, R M., Karacay, Griffiths, G L., Behr, T M., Blumenthal, R D., Mattes, M J., Hansen, H J., Goldenberg. Development of a streptavidin-anti-carcinoembryonic antigen antibody, radiolabeled biotin pretargeting method for radioimmunotherapy of colorectal cancer. Studies in a human colon cancer xenograft model. *Bioconjugate Chem* 1997; 8:595-604.

Stickney, D R., Anderson, L D., Slater, J B., Ahlem, C N., Kirk, G A., Schweighardt, S A and Frincke, J M. Bifunctional antibody: a binary radiopharmaceutical delivery system for imaging colorectal carcinoma. *Cancer Res.* 1991;51: 6650-6655.

All references cited herein are hereby incorporated herein by reference in their entireties.

---

What is claimed is:

1. A method of treating or diagnosing a disease or a condition that may lead to a disease comprising:
   (A) administering to a subject a bi-specific antibody or fragment thereof having at least one arm that specifically binds a targeted tissue and at least one other arm that specifically binds a targetable construct;
   (B) optionally, administering to said subject a clearing composition to clear unbound bi-specific antibodies or fragments thereof from circulation; and
   (C) administering to said subject a targetable construct comprising a compound of the formula X-Phe-Lys (HSG)-D-Tyr-Lys(HSG)-Lys(Y)—NH$_2$ (SEQ ID NO: 1), wherein the compound includes a hard acid cation chelator at X or Y, and a soft acid cation chelator at the remaining X or Y, further comprising at least one therapeutic agent, diagnostic agent, or enzyme attached to the targetable construct.

2. The method of claim 1, wherein the therapeutic or diagnostic agent is a cation that is chelated to the hard acid cation chelator or soft acid cation chelator.

3. The method of claim 1, wherein the therapeutic agent or diagnostic agent is a radionuclide that emits particles and/or positrons having 20 to 10,000 keV.

4. The method of claim 3, wherein said radionuclide is a therapeutic agent selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb.

5. The method of claim of claim 1, wherein the therapeutic agent is a radionuclide, drug, prodrug or toxin.

6. The method of claim 3, wherein said radionuclide is a diagnostic agent selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb and $^{83}$Sr.

7. The method of claim 1, wherein said diagnostic agent is used to perform positron-emission tomography (PET).

8. The method of claim 1, wherein said diagnostic agent is used to perform SPECT maging.

9. The method of claim 1, wherein said diagnostic agent includes one or more image enhancing agents for use in magnetic resonance imaging (MRI).

10. The method of claim 9, wherein said enhancing agent is selected from the group consisting of Mn, Fe, La and Gd.

11. The method of claim 1, wherein said diagnostic agent comprises one or more radiopaque or contrast agents for X-ray or computed tomography.

12. The method of claim 11, wherein said radiopaque or contrast agents are selected from the group consisting of barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosernetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

13. The method of claim 1, wherein said diagnostic agent comprises one or more ultrasound contrast agents.

14. The method of claim 1, wherein said therapeutic agent, diagnostic agent or enzyme is chemically bound to said targetable construct.

15. The method of claim 1, wherein said diagnostic agent is selected from the group consisting of a fluorescent compound, a chemiluminescent compound, and a bioluminescent compound.

16. The method of claim 15, wherein said fluorescent compound is selected from the group consisting of fluorescein isothiocyanate, rhodamine, phycoerytherin, phycocyanin, allophycocyanin, o-phthaldehyde and fluorescamine.

17. The method of claim 15, wherein said chemiluminescent compound is selected from the group consisting of luminol, isoluminol, an aromatic acridinium ester, an imidazole, an acridinium salt and an oxalate ester.

18. The method of claim 15, wherein said bioluminescent compound is selected from the group consisting of luciferin, luciferase and aequorin.

19. The method of claim 1, wherein said targeted tissue is a tumor.

20. The method of claim 19, wherein said tumor produces at least one antigen selected from the group consisting of colon-specific antigen-p (GSAp), carcinoembryonic antigen (CEA), CD19, CD20, CD21, CD22, CD23, CD30, CD74, CD80, HLA-DR, Ia, MUC 1, MUC 2, MUC 3, MUC 4, EGFR, HER 2/neu, antigen bound by PAM-4, TAG-72, EGP-1, EGP-2, A3, KS-1, Le(y), S100, PSMA, PSA, tenascin, folate receptor, VEGFR, necrosis antigens, IL-2, T101 and MAGE.

21. The method of claim 1, wherein said at least one arm that specifically binds a targeted tissue is a monoclonal antibody (MAb) or a fragment of a monoclonal antibody.

22. The method of claim 1, wherein said at least one other arm that specifically binds a targetable construct is a monoclonal antibody or a fragment of a monoclonal antibody.

23. The method of claim 1, wherein said at least one arm that specifically binds a targeted tissue is a human, chimeric or humanized antibody or a fragment of a human, chimeric or humanized antibody.

24. The method of claim 1, wherein said at least one other arm that specifically binds a targetable construct is a human, chimeric or humanized antibody or a fragment of a human, chimeric or humanized antibody.

25. The method of claim 1, wherein said therapeutic agent or diagnostic agent is a hard acid cation chelated to the hard acid chelator or a soft acid cation chelated to the soft acid chelator.

26. The method of claim 25, wherein said hard acid cation is a Group Ia or Group IIIa metal cation.

27. The method of claim 1, wherein the bi-specific antibody comprises the Fv of MAb Mu-9 and the Fv of MAb 679.

28. The method of claim 27, wherein Mu-9 and/or 679 are chimerized or humanized.

29. The method of claim 25, wherein the soft acid cation is a transition metal, lanthanide, actinide, Bi, Tc or Re.

30. The method of claim 27, wherein the bi-specific antibody comprises the CDRs of Mu-9.

31. The method of claim 27, wherein the bi-specific antibody comprises the CDRs of 679.

32. The method of claim 27, wherein the bi-specific antibody is a fusion protein.

33. The method of claim 1, wherein the bi-specific antibody comprises the Fv of MAb MN-14 and the Fv of MAb 679.

34. The method of claim 33, wherein MN-14, and/or 679 are chinierized or humanized.

35. The method of claim 33, wherein the bi-specific antibody comprises the CDRs of MN-14.

36. The method of claim 33, wherein the bi-specific antibody comprises the GDRs of 679.

37. The method of claim 33, wherein the bi-specific antibody isa fusion protein.

38. The method of claim 37, vherein the fusion protein is trivalent, and incorporates the Fv of an antibody reactive with CSAp.

39. The method of claim 1, wherein the bi-specific antibody incorporates a Class-III anti-CEA antibody and the Fv of 679.

40. The method of claim 1, wherein said targetable construct comprises one or more radioactive isotopes useful for killing diseased tissue.

41. The method of claim 1, wherein said targetable construct comprises $^{10}B$ atoms, and said method further comprises the step of neutron irradiating said boron atoms localized at said diseased tissue, thereby effecting BNCT of said diseased tissue.

42. The method of claim 1, when said targetable construct comprises an enzyme and said method further comprises administering to said subject a drug which said enzyme is capable of converting to a toxic form, and, therefore, increasing the toxicity of said drug at the target site.

43. A method for detecting or treating target cells, tissues or pathogens in a mammal, comprising:
administering a bi-specific antibody or fragment thereof comprising at least one arm that specifically binds a target and at least one other arm that specifically binds a targetable construct; and
administering a targetable construct comprising the compound of the formula X-Phe-Lys (HSG)-D-Tyr-Lys (HSG)-Lys(Y)-NH$_2$ (SEQ ID NO:1), wherein the compound includes a hard acid cation chelator at X or Y, and a soft acid cation chelator at the remaining X or Y, further comprising at least one therapeutic agent, diagnostic agent, or enzyme attached to the taroetable construct;
wherein said target includes a target cell, tissue, pathogen or a molecule produced by or associated therewith and at least one arm that specifically binds said target is capable of binding to a complementary binding moiety on the target.

44. The method of claim 43, wherein said pathogen is a fungus, virus, parasite, bacterium, protozoan, or mycoplasm.

45. The method of claim 44, wherein said fungus is selected from the group consisting of *Microsporum, Trichophyton, Epidermophyton, Sporothrix schenckii, Cyrptococcus neoformans, Coccidioides immitis, Histoplasma capsulatum, Blastomyces dermatitidis* and *Candida albicans*.

46. The method of claim 44, wherein said virus is selected from the group consisting of human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus.

47. The method of claim 44, wherein said bacterium is selected from the group consisting of *Anthrax bacillus, Streptococcus agalactiae, Legionella pneumophilia, Streptococcus pyogenes, Escherichia coli, Neisseria gonorrhoeae, Neisseria meningitidis, Pneurnococcus, Hemophilis influenzae B, Treponema pallidum, Lyme disease spirochetes, Pseudomonas aeruginosa, Mycobacterium leprae, Brucella abortus* and *Mycobacterium tuberculosis*.

48. The method of claim 44, wherein said parasite is a helminth or a malarial parasite.

49. The method of claim 44, wherein said protozoan is selected from the group consisting of *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides coili*.

50. The method of claim 44, wherein said mycoplasma is selected from the group consisting of *Mycoplasma arthritidis, Mycoplasina hyorhinis, Mycoplasma orale, Mycoplasma arginini, Acholeplasma laidlawii, Mycoplasma sal ivarum,* and *Mycoplasma pneumoneiae*.

51. The method of claim 43, wherein said targetable construct comprises at least one radionuclide, therapeutic agent, detectable diagnostic agent or enzyme.

52. The method of claim 51, wherein the radionuclide is selected from the group consisting of $^{225}$Ac, $^{111}$Ag, $^{72}$As, $^{211}$At, $^{198}$Au, $^{199}$Au, $^{212}$Bi, $^{213}$Bi, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{143}$Pr, $^{223}$Ra, $^{82m}$Rb, $^{186}$Re, $^{188}$Re, $^{189}$Re, $^{105}$Re, $^{47}$Rh, $^{153}$Sm, $^{75}$Se, $^{83}$Sr, $^{89}$Sr, $^{161}$Tb, $^{94m}$Tc, $^{94}$Tc, $^{94m}$Tc, $^{86}$Y, $^{90}$Y and $^{89}$Zr; and, when the targetable construct includes more than one radionuclide, the radionuclides may be different radionuclides.

53. The method of claim 51, wherein the diagnostic agent includes an imaging agent of use to detect the target cells, tissues or pathogens in a mammal.

54. A method of treating or detecting diseased tissues in a subject, comprising:
administering to said subject a bi-specific antibody or fragment thereof having at least one arm that specifically binds a targeted diseased tissue and at least one other arm that specifically binds a targetable construct;
optionally, administering to said subject a clearing composition to clear unbound bi-specific antibodies or fragments thereof from circulation; and
administering to said subject a targetable construct comprising the compound of the formula X-Phe-Lys(HSG)-D-Tyr-Lys(HSG)-Lys(Y)-NH$_2$ (SEQ ID NO: I), wherein the compound includes a hard acid cation chelator at X or Y, and a soft acid cation chelator at the remaining X or Y, further comprising at least one therapeutic agent, diagnostic agent or enzyme attached to the targetable construct.

55. The method of claim 54, wherein said subject is mammalian.

56. The method of claim 55, wherein said mammalian subject is selected from the group consisting of humans, primates, equines, canines and felines.

57. The method of claim 54, wherein said targetable construct comprises at least one radionuclide, therapeutic agent, detectable diagnostic agent or enzyme.

58. The method of claim 57, wherein the radionuclide is selected from the group consisting of $^{225}$Ac, $^{111}$Ag, $^{72}$As, $^{211}$At, $^{198}$Au, $^{199}$Au, $^{212}$Bi, $^{213}$Bi, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{143}$Pr, $^{223}$Ra, $^{82m}$Rb, $^{186}$Re, $^{188}$Re, $^{189}$Re, $^{105}$Re, $^{47}$Rh, $^{153}$Sm, $^{75}$Se, $^{83}$Sr, $^{89}$Sr, $^{161}$Tb, $^{94m}$Tc, $^{94}$Tc, $^{94m}$Tc, $^{86}$Y, $^{90}$Y and $^{89}$Zr; and, when the targetable construct includes more than one radionuclide, the radionuclides may be different radionuclides.

59. The method of claim 57, wherein the diagnostic agent includes an imaging agent of use to detect the target cells, tissues or pathogens in a. mammal.

60. The method of claim 57, wherein the therapeutic agent includes drugs, toxins, cytokines, hormones, or growth factors.

61. A method for imaging normal tissue in a mammal comprising:
administering a bi-specific antibody or fragment thereof having at least one arm that specifically binds a targeted normal tissue and at least one other arm that specifically binds a targetable construct; and
administering to said mammal a targetable construct comprising a compound of the formula X-Phe-Lys(HSG)-D-Tyr-Lys(HSG)-Lys(Y)-NH$_2$ (SEQ ID NO:!), wherein the compound includes a hard acid cation chelator at X or Y, and a soft acid cation chelator at the remaining X or Y, the targetable construct attached to at least one imaging agent.

62. The method of claim 61, wherein said normal tissue is tissue from the ovary, thymus, parathyroid, endometriuni, bone marrow, or spleen.

63. The method of claim 61, wherein the imaging agent is a radionuclide selected from the group consisting $^{225}$Ac, $^{111}$Ag, $^{72}$As, $^{211}$At, $^{198}$Au, $^{199}$Au, $^{212}$Bi, $^{213}$Bi, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{143}$Pr, $^{223}$Ra, $^{82m}$Rb, $^{186}$Re, $^{188}$Re, $^{189}$Re, $^{105}$Re, $^{47}$Rh, $^{153}$Sm, $^{75}$Se, $^{83}$Sr, $^{89}$Sr, $^{161}$Tb, $^{94m}$Tc, $^{94}$Tc, $^{94m}$Tc, $^{86}$Y, $^{90}$Y and $^{89}$Zr; and, when the targetable construct includes more than one radionuclide, the radionuclides may be different radionuclides.

64. The method of claim 61, wherein the imaging agent includes a contrast agent.

65. The method of claim 61, wherein said imaging agent is an agent used for PET.

66. The method of claim 61, wherein the imaging agent is an agent used for SPECT.

67. A method of intraoperatively detecting diseased tissues, in a subject, comprising:
administering a bi-specific antibody or fragment thereof; and
administering a targetable construct comprising the compound of the formula X-Phe-Lys (HSG)-D-Tyr-Lys (HSG)-Lys(Y)-NH$_2$ (SEQ ID NO: 1), wherein the compound includes a hard acid cation chelator at X or Y, and a soft acid cation chelator at the remaining X or further comprising at least one detectable diagnostic agent attached to said targetable construct;
wherein the bi-specific antibody or fragment thereof comprises at least one arm that specifically binds a targeted diseased tissue and at least one other arm that specifically binds the targetable construct.

68. The method of claim 67, wherein the diagnostic agent is a radionuclide selected from the group consisting of $^{225}$Ac, $^{111}$Ag, $^{72}$As, $^{211}$At, $^{198}$Au, $^{199}$Au, $^{212}$Bi, $^{213}$Bi, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{143}$Pr, $^{223}$Ra, $^{82m}$Rb, $^{186}$Re, $^{188}$Re, $^{189}$Re, $^{105}$Re, $^{47}$Rh, $^{153}$Sm, $^{75}$Se, $^{83}$Sr, $^{89}$Sr, $^{161}$Tb, $^{94m}$Tc, $^{94}$Tc, $^{94m}$Tc, $^{86}$Y, $^{90}$Y and $^{89}$Zr; and, when the targetable construct includes more than one radionuclide, the radionuclides may be different radionuclides.

69. The method of claim 67, wherein the diagnostic agent includes a contrast agent to enhance detection of targetable construct that is bound to the bi-specific antibody or fragment thereof.

70. The method of claim 67, wherein the diagnostic agent includes an imaging agent to detect targetable construct that is bound to the bi-specific antibody or fragment thereof.

71. A method for the endoscopic detection of diseased tissues, in a subject, comprising:
   administering a bi-specific antibody or fragment thereof; and
   administering a targetable construct comprising a compound of the formula X-Phe-Lys (HSG)-D-Tyr-Lys (HSG)-Lys(Y)-NH$_2$ (SEQ ID NO: 1); wherein the compound includes a hard acid cation chelator at X or Y, and a soft acid cation chelator at the remaining X or Y, further comprising at least one detectable diagnostic agent attached to said targetable construct; wherein the bi-specific antibody or fragment thereof comprises at least one arm that specifically binds a targeted diseased tissue and at least one other arm that specifically binds the targetable construct.

72. The method of claim 7, wherein the diagnostic agent is a radionuclide selected from the group consisting of $^{225}$Ac, $^{111}$Ag, $^{72}$As, $^{211}$At, $^{198}$Au, $^{199}$Au, $^{212}$Bi, $^{213}$Bi, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{143}$Pr, $^{223}$Ra, $^{82m}$Rb, $^{186}$Re, $^{188}$Re, $^{189}$Re, $^{105}$Re, $^{47}$Rh, $^{153}$Sm, $^{75}$Se, $^{83}$Sr, $^{89}$Sr, $^{161}$Tb, $^{94m}$Tc, $^{94}$Tc, $^{94m}$Tc, $^{86}$Y, $^{90}$Y and $^{89}$Zr; and, when the targetable construct includes more than one radionuclide, the radionuclides may be different radionuclides.

73. The method of claim 71, wherein the diagnostic agent includes a contrast agent to enhance detection of targetable construct that is bound to the bi-specific antibody or fragment thereof.

74. The method of claim 71, wherein the diagnostic agent includes an imaging agent to detect targetable construct that is bound to the bi-specific antibody or fragment thereof.

75. A method for the intravascular detection of diseased tissues, in a subject, comprising:
   administering a bi-specific antibody or fragment thereof comprising at least one arm that specifically binds a targeted diseased tissue and at least one other arm that specifically binds a targetable construct; and
   administering a targetable construct comprising a compound of the formula X-Phe-Lys (HSG)-D-Tyr-Lys (HSG)-Lys(Y)-NH$_2$ (SEQ ID NO:1), wherein the compound includes a hard acid cation chelator at X or Y, and a soft acid cation chelator at the remaining X or Y, further comprising at least one detectable diagnostic agent attached to said targetable construct.

76. The method of claim 75, wherein the diagnostic agent is a radionuclide selected from the group consisting of $^{225}$Ac, $^{111}$Ag, $^{72}$As, $^{211}$At, $^{198}$Au, $^{199}$Au, $^{212}$Bi, $^{213}$Bi, $^{76}$Br, $^{11}$C, $^{55}$Co, $^{62}$Cu, $^{64}$Cu, $^{67}$Cu, $^{166}$Dy, $^{169}$Er, $^{18}$F, $^{52}$Fe, $^{59}$Fe, $^{67}$Ga, $^{68}$Ga, $^{154}$Gd, $^{155}$Gd, $^{156}$Gd, $^{157}$Gd, $^{158}$Gd, $^{166}$Ho, $^{120}$I, $^{123}$I, $^{124}$I, $^{125}$I, $^{131}$I, $^{110}$In, $^{111}$In, $^{194}$Ir, $^{177}$Lu, $^{51}$Mn, $^{99}$Mo, $^{13}$N, $^{15}$O, $^{32}$P, $^{33}$P, $^{211}$Pb, $^{212}$Pb, $^{109}$Pd, $^{149}$Pm, $^{143}$Pr, $^{223}$Ra, $^{82m}$Rb, $^{186}$Re, $^{188}$Re, $^{189}$Re, $^{105}$Re, $^{47}$Rh, $^{153}$Sm, $^{75}$Se, $^{83}$Sr, $^{89}$Sr, $^{161}$Tb, $^{94m}$Tc, $^{94}$Tc, $^{94m}$Tc, $^{86}$Y, $^{90}$Y and $^{89}$Zr; and, when the targetable construct includes more than one radionuclide, the radionuclides may be different radionuclides.

77. The method of claim 75, wherein the diagnostic agent includes a contrast agent to enhance detection of targetable construct that is bound to the bi-specific antibody or fragment thereof.

78. The method of claim 75, wherein the diagnostic agent includes an imaging agent to detect targetable contstruct that is bound to the bi-specific antibody or fragment thereof.

\* \* \* \* \*

UNITED STATES PATENT AND TRADEMARK OFFICE
CERTIFICATE OF CORRECTION

PATENT NO. : 7,560,110 B2
APPLICATION NO. : 11/198846
DATED : July 14, 2009
INVENTOR(S) : David M. Goldenberg et al.

It is certified that error appears in the above-identified patent and that said Letters Patent is hereby corrected as shown below:

In Claim 8, line 2 (Col. 88, line 10) "maging" should read: "imaging".

In Claim 20, line 3 (Col. 89, line 20) "(GSAp)" should read: "(CSAp)".

In Claim 34, line 2 (Col. 89, line 63) "chinierized" should read: "chimerized".

In Claim 36, line 2 (Col. 89, line 67) "GDRs" should read: "CDRs".

In Claim 38, line 1 (Col. 90, line 3) "vherein" should read: "wherein".

In Claim 43, line 13 (Col. 90, line 34) "taroetable" should read: "targetable".

In Claim 47, line 5 (Col. 90, line 62) "Pneurnococcus" should read: "Pneumococcus".

In Claim 49, line 7-8 (Col. 91, line 7-8) "Onchocerca volvulus" should be deleted.

In Claim 50, line 3 (Col. 91, line 13) "Mycoplasina" should read: "Mycoplasma".

In Claim 50, line 4 (Col. 91, line 14) "sal ivarum" should read: "salivarum".

In Claim 52, line 9 (Col. 91, line 27) ".sup.94mTc" should read: ".sup.99mTc".

In Claim 58, line 9 (Col. 91, line 66) ".sup.94mTc" should read: ".sup.99mTc".

In Claim 59, line 1 (Col. 92, line 3) "diagnostic,agent" should read: "diagnostic agent".

In Claim 59, line 3 (Col. 92, line 5) "a. mammal" should read: "a mammal".

In Claim 61, line 9 (Col. 92, line 17) "(SEQ ID NO:!)" should read: "SEQ ID NO:1".

In Claim 62, line 2 (Col. 92, line 23) "endometriuni" should read: "endometrium".

In Claim 63, line 9 (Col. 92, line 33) ".sup.94mTc" should read: ".sup.99mTc".

In Claim 67, line 9 (Col. 92, line 50) "X or further" should read: "X or Y, further".

UNITED STATES PATENT AND TRADEMARK OFFICE
CERTIFICATE OF CORRECTION

PATENT NO. : 7,560,110 B2
APPLICATION NO. : 11/198846
DATED : July 14, 2009
INVENTOR(S) : David M. Goldenberg et al.

It is certified that error appears in the above-identified patent and that said Letters Patent is hereby corrected as shown below:

In Claim 68, line 9 (Col. 92, line 65) ".sup.94mTc" should read: ".sup.99mTc".

In Claim 72, line 9 (Col. 93, line 31) ".sup.94mTc" should read: ".sup.99mTc".

In Claim 76, line 9 (Col. 94, line 25) ".sup.94mTc" should read: ".sup.99mTc".

Signed and Sealed this

Twenty-fifth Day of August, 2009

David J. Kappos
*Director of the United States Patent and Trademark Office*

SEQUENCE LISTING

<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys (HSG) Histamine-succinyl-glycyl
<220> FEATURE:
<221> NAME/KEY: MOD_RES
<222> LOCATION: (3)
<223> OTHER INFORMATION: D-Tyr
<220> FEATURE:
<221> NAME/KEY: MOD_RES
<222> LOCATION: (4)
<223> OTHER INFORMATION: Lys (HSG) Histamine-succinyl-glycyl

<400> SEQUENCE: 1

Phe Lys Tyr Lys Lys
 1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Phe Lys Tyr Lys
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys (HSG) Histamine-succinyl-glycyl
<220> FEATURE:
<221> NAME/KEY: MOD_RES
<222> LOCATION: (3)
<223> OTHER INFORMATION: D-Tyr
<220> FEATURE:
<221> NAME/KEY: MOD_RES
<222> LOCATION: (4)
<223> OTHER INFORMATION: Lys (HSG) Histamine-succinyl-glycyl

<400> SEQUENCE: 3

Phe Lys Tyr Lys
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Tyr

<400> SEQUENCE: 4

Lys Tyr Lys Lys
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Ala
<220> FEATURE:
<221> NAME/KEY: MOD_RES
<222> LOCATION: (2)
<223> OTHER INFORMATION: Lys (HSG) Histamine-succinyl-glycyl
<220> FEATURE:
<221> NAME/KEY: MOD_RES
<222> LOCATION: (4)
<223> OTHER INFORMATION: Lys (HSG) Histamine-succinyl-glycyl

<400> SEQUENCE: 5

Ala Lys Tyr Lys
  1

<210> SEQ ID NO 6
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Ala
<220> FEATURE:
<221> NAME/KEY: MOD_RES
<222> LOCATION: (2)
<223> OTHER INFORMATION: Lys (HSG) Histamine-succinyl-glycyl
<220> FEATURE:
<221> NAME/KEY: MOD_RES
<222> LOCATION: (3)
<223> OTHER INFORMATION: D-Tyr
<220> FEATURE:
<221> NAME/KEY: MOD_RES
<222> LOCATION: (4)
<223> OTHER INFORMATION: Lys (HSG) Histamine-succinyl-glycyl

<400> SEQUENCE: 6

Ala Lys Tyr Lys
 1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Tyr Lys Lys
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ala Glu Tyr
 1

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 9

Gly Gly Gly Gly Ser Gly Gly Gly Gly Ser Gly Gly Gly Gly Ser
 1               5                  10                  15

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 10

Gly Gly Gly Ser
```

-continued

```
<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Lys Tyr Lys
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Lys Ser Cys
 1

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Leu Val Val Thr Gln
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Lys Leu Lys Ile Leu
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 15

Gly Gly Gly Gly Ser Gly Gly Gly Gly
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                                   -continued peptide linker

<400> SEQUENCE: 16

Ser Gly Gly Gly Gly Ser
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Val Lys Leu Gln Glu
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Val Thr Val Ser Ser
 1               5
```